United States Patent [19]

Atwood et al.

[11] 4,052,161
[45] Oct. 4, 1977

[54] KINETIC ANALYZER

[75] Inventors: John G. Atwood, Redding; Hamilton W. Marshall, Jr., Ridgefield; Peter H. Heinz, Trumbull, all of Conn.

[73] Assignee: The Perkin-Elmer Corporation, Norwalk, Conn.

[21] Appl. No.: 594,951

[22] Filed: July 10, 1975

Related U.S. Application Data

[63] Continuation of Ser. No. 499,602, Aug. 22, 1974, abandoned.

[51] Int. Cl.² .................... G01N 33/16; G01N 21/24; G01N 21/26
[52] U.S. Cl. .............................. 23/230 R; 23/253 R; 356/246
[58] Field of Search .................... 23/253, 230 R, 259, 23/292

[56] References Cited

U.S. PATENT DOCUMENTS

| 3,565,582 | 2/1971 | Young | 23/253 X |
| 3,592,605 | 7/1971 | Noma et al. | 23/292 X |
| 3,664,744 | 5/1972 | Liston | 23/253 UX |
| 3,728,079 | 4/1973 | Moran | 23/253 R |
| 3,753,657 | 8/1973 | Downing et al. | 23/259 X |
| 3,790,346 | 2/1974 | Ritchie | 23/253 R |
| 3,883,305 | 5/1975 | Hoskins | 23/253 |
| 3,932,131 | 1/1976 | Rolfo-Fontana | 23/253 X |

Primary Examiner—R.E. Serwin

Attorney, Agent, or Firm—S. A. Giarratana; F. L. Masselle; E. T. Grimes

[57] ABSTRACT

A completely automated kinetic analyzer particularly suited for performing classical kinetic chemistries on an ultra-micro scale. The analyzer comprises a sample preparation unit and a photometric analytical unit. The preparation unit includes a rotationally indexed tray of sample containers presented in timed sequence to a diluter probe which effects dilution of the samples while transferring them sequentially to respective reaction cups, batches of which are contained in magazines and previously filled, by means of an automatic pipetter, with a first reagent. Conveyors move the magazines in stages through the preparation unit, the sample-reagent mixtures meanwhile undergoing preincubation. A second automatic pipetter thereafter adds a second reagent to each cup, in turn the contents of which are then mixed by an automatic stirrer. The magazines are advanced in stepwise fashion to the analytical unit which includes a photometer having a curvette mounted in a temperature-controlled environment as well as radiometric, computation, and print-out means. A transfer probe picks up the stirred mixture from the reaction cups, in series, and introduces each through a heat exchanger into the curvette where the absorptivity of the mixture is protometrically monitored for a predetermined period and the rate of change in absorbance automatically computed and printed out in standard units representative of the content of the samples of the particular constituent being determined.

49 Claims, 59 Drawing Figures

TABLE IV

PARAMETER, MEMORY

| SELECTION ON FRONT CONTROL PANEL | TEST NAME (PRINTER) | CHEMICAL REACTION ASSUMED (Fig. 18 Switches 309,312,313) | PHOTOMETRIC WAVELENGTH (Fig. 13 Mirror 277 Filter 281 | INCUBATION TIME (Fig. 9-SS1 or SS3) | EXTENSION COEFFICIENT (Fig 19 Switch 331) | THRESHOLDS FOR HIGH AND LOW ABSORBANCE |
|---|---|---|---|---|---|---|
| LDH | LDH | DOWN | 340mm | 24 sec | 63/640 | One for High One for Low |
| SGOT | SGOT | DOWN | 340mm | 24 sec | 63/640 | One for High One for Low |
| SGPT | SGPT | DOWN | 340mm | 24 sec | 63/640 | One for High One for Low |
| CPK | CPK | UP | 340mm | 120 sec | 63/640 | One for High One for Low |
| ALKP | ALKP | UP | 404mm | 24 sec | 21/640 | One for High One for Low |
| AUX | 16 Options set on Aux Panel | Set on Aux Panel | Set on Aux Panel | Set on Aux Panel | $\frac{N}{10,000}$ (N set on Aux Panel) | One for High One for Low (On Aux Panel) |

FIG. 12a

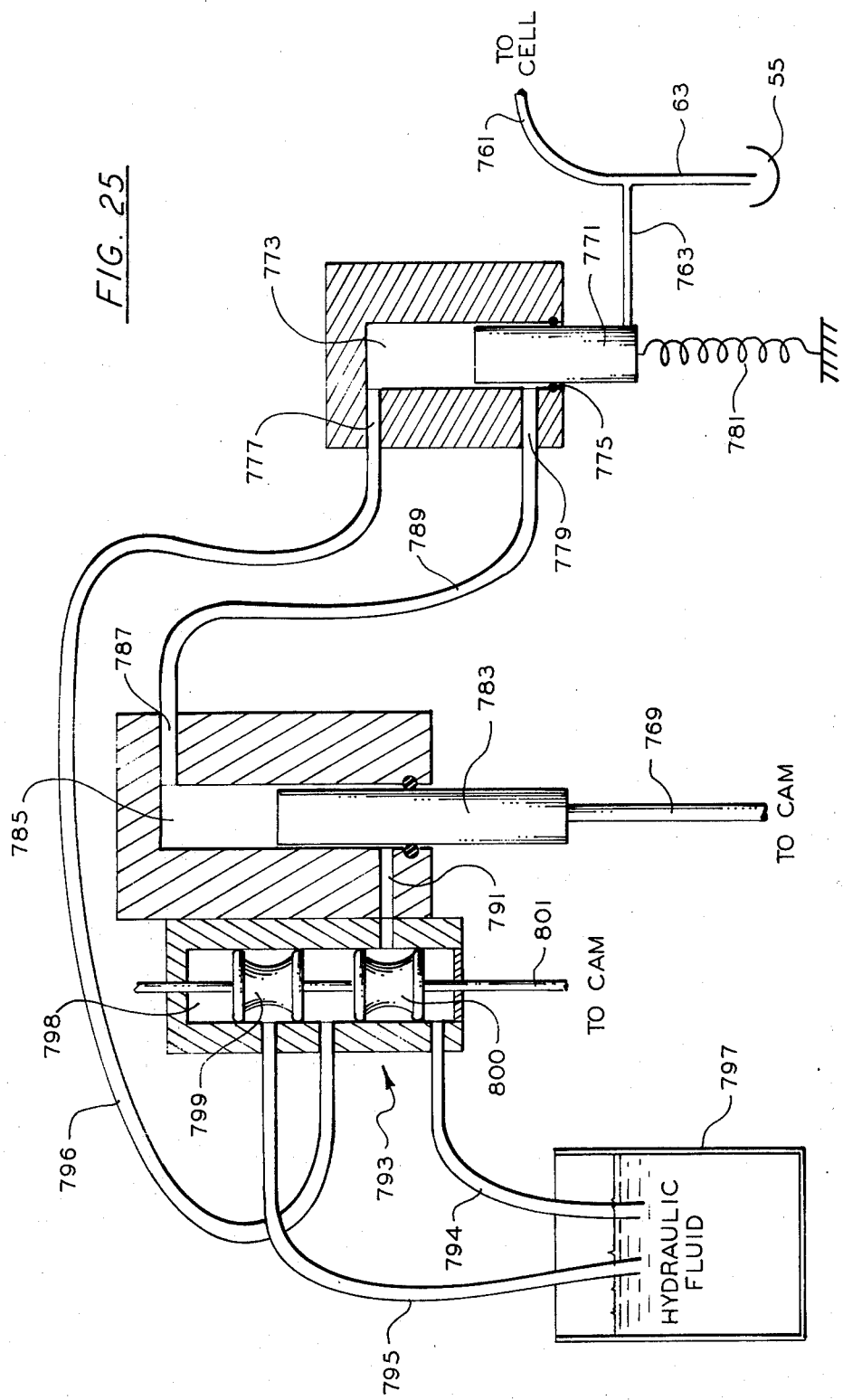

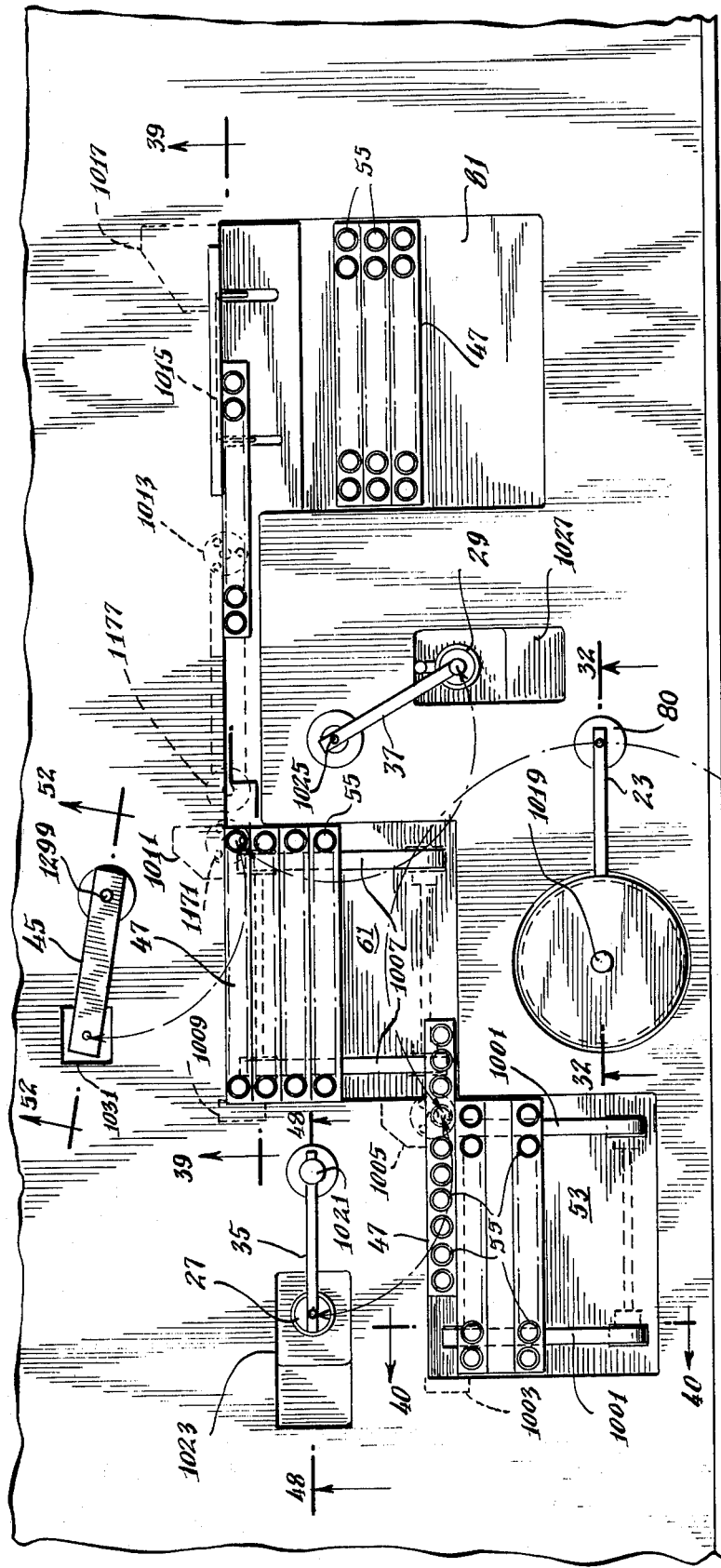
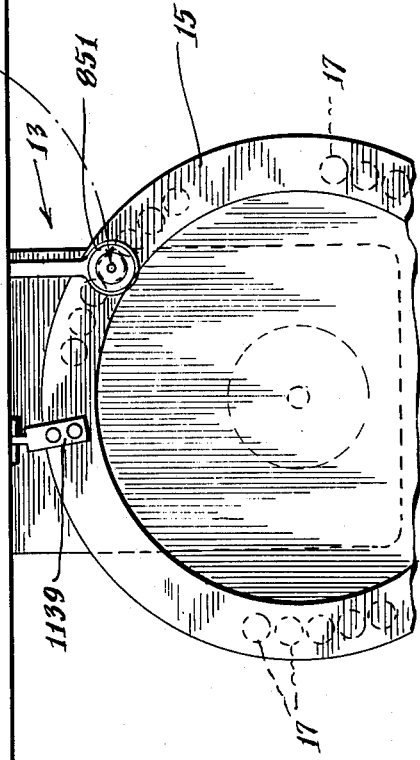
Fig. 31.

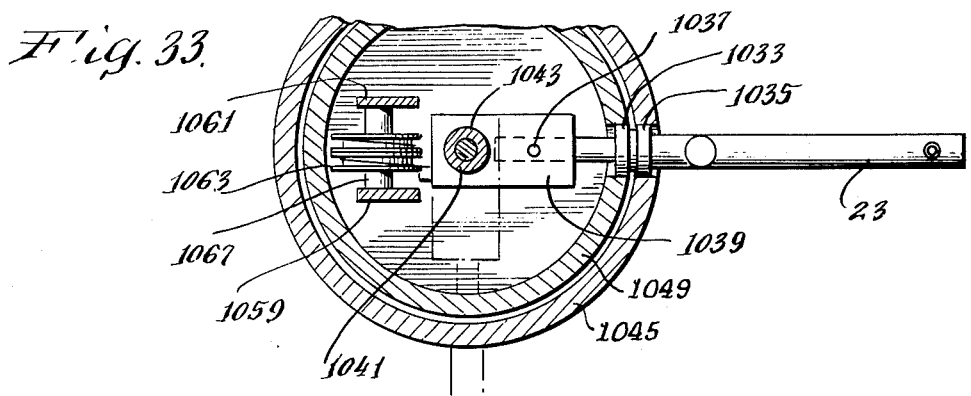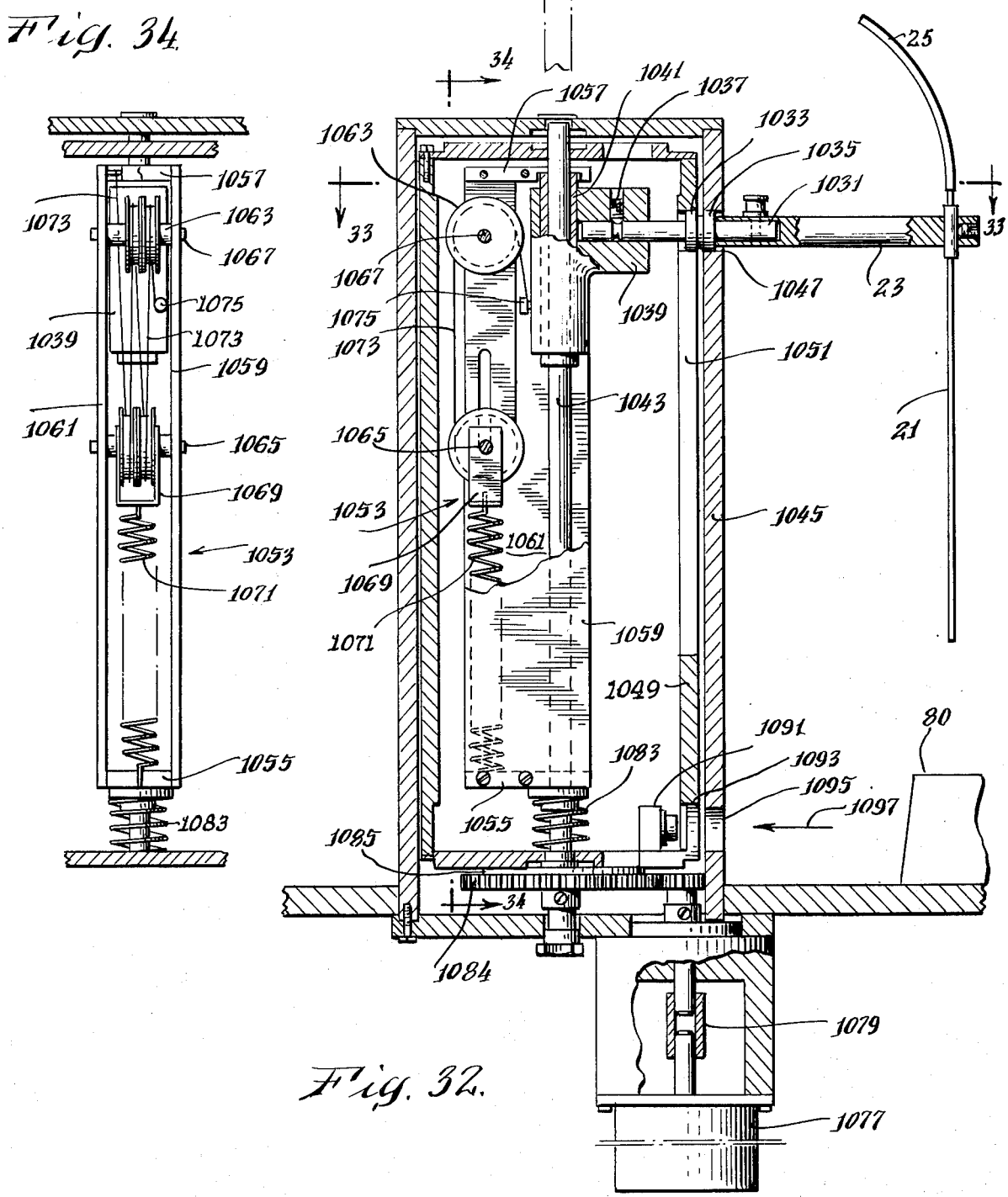

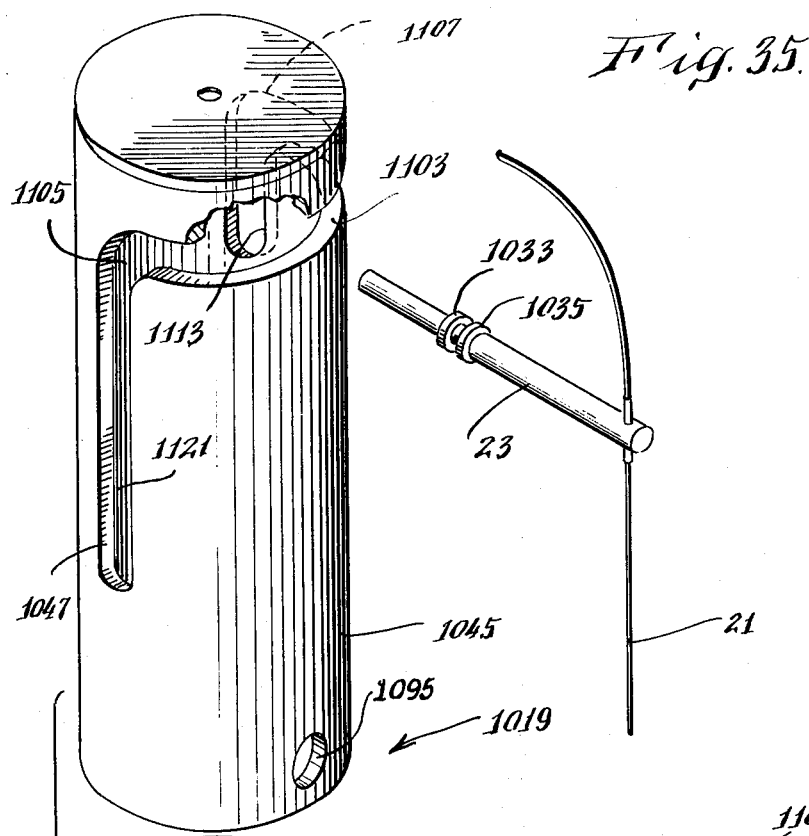
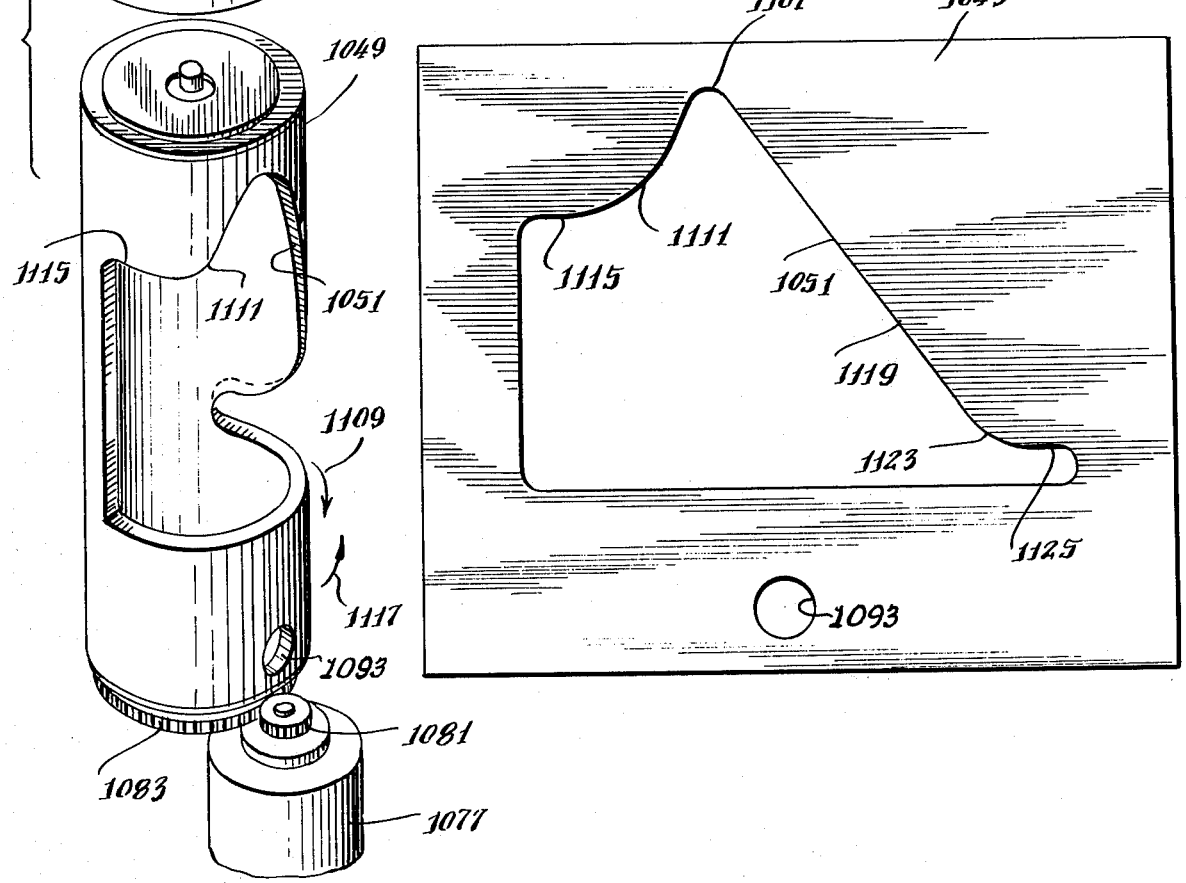
Fig. 35.
Fig. 36.

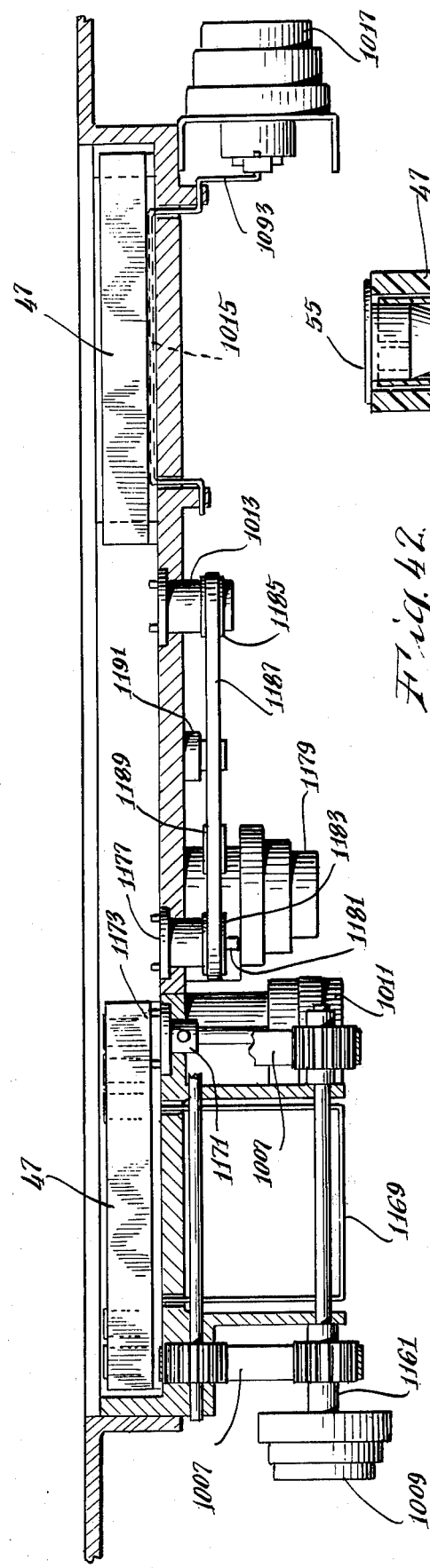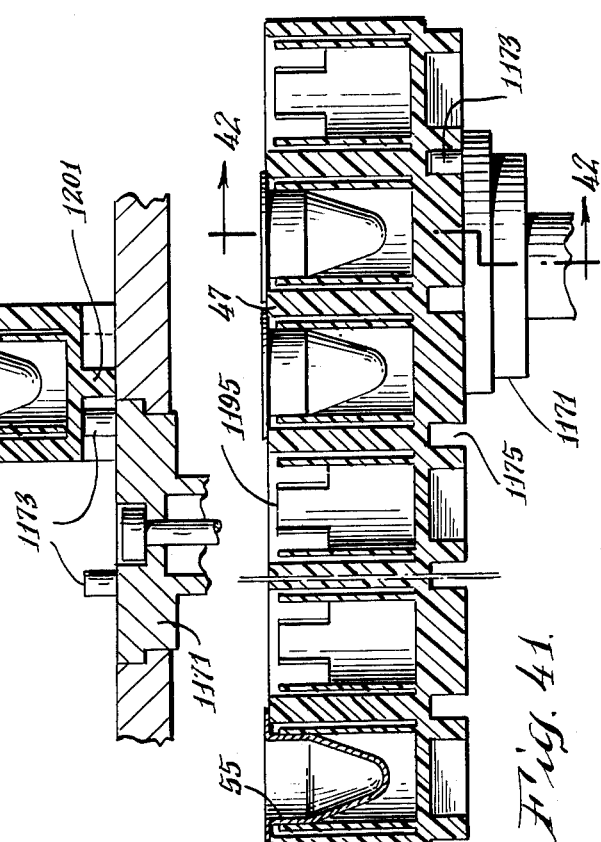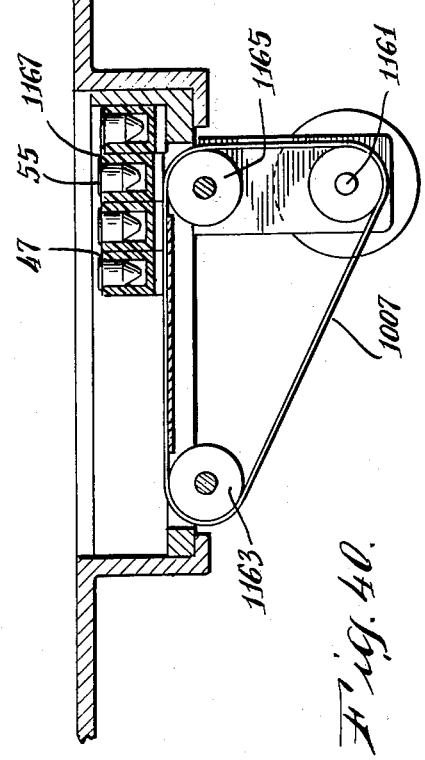

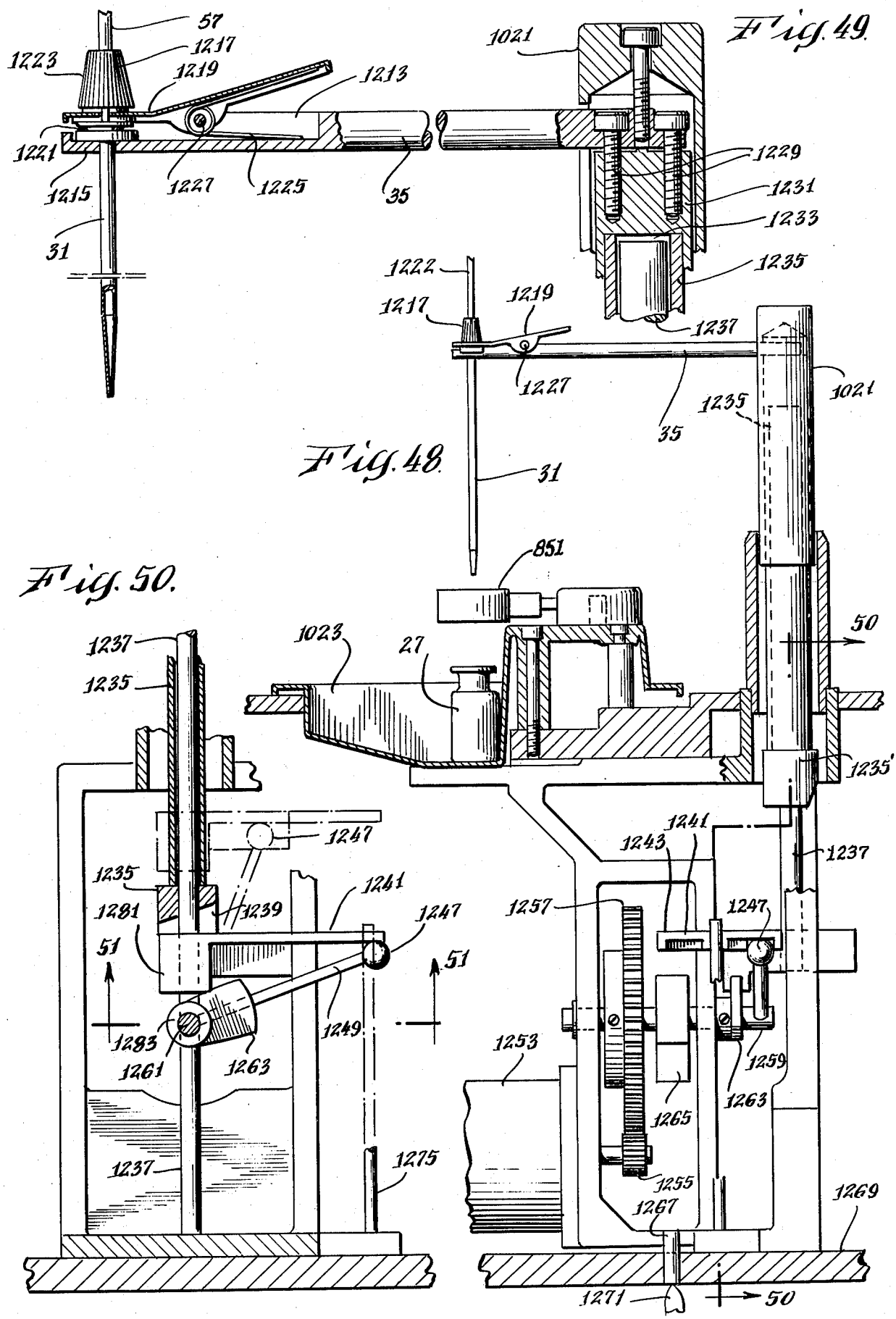

KINETIC ANALYZER

This application is a continuation of Ser. No. 499,602, filed Aug. 22, 1974, and now abandoned.

BACKGROUND OF THE INVENTION

This invention relates to kinetic analysis in general, and more particularly to an improved method and apparatus for automatically carrying out classical kinetic chemistries on an ultra-micro scale at high rates and low cost.

In the serum chemistry art, various classical kinetic chemistries for performing kinetic analysis have been developed over the years. Typical of these tests are the tests for the determination of enzymes known as LDH, ALKP, SGOT, SGPT, and CPK. In general, each of these tests require mixing two reagents, along with a diluent, with a serum sample to be analyzed and, after a period of incubation, analyzing the kinetic chemistry by observing the photo-absorbence of the mixture over a predetermined period and calculating the rate of change of such absorbence. Various automated devices have been developed to speed up this analysis. In particular, automatic apparatus for transferring the reacting mixture to be observed to a photometer has been developed. The various types of apparatus available generally require a certain amount of the work be done by the operator and few can be truly considered completely automatic. In addition, prior art methods generally fail to provide adequate temperature control. Moreover, these prior art automatic analyzers generally work with relatively large quantities of sample and reagent thereby increasing the cost of running the test. Apart from the cost involved, the availability of adequate quanties of serum for analysis is sometimes a factor, for example, in the case of small infants. The photometric apparatus in these devices is limited in sensitivity and the prior art methods of computing absorbence give rise to various types of errors. Furthermore, the speed at which they can process samples is relatively low thereby further increasing the cost of running tests.

In view of these various deficiencies in prior art analyzing apparatus, it is clear that there is a need for automatic apparatus of this type which can quickly, efficiently, inexpensively and accurately carry out a large plurality of the different tests which must be performed.

SUMMARY OF THE INVENTION

The present invention provides such an apparatus. It automates classical kinetic chemistries on an ultra-micro scale and handles samples at a rate of 150 per hour. It is extremely simple to operate and uses low cost reagents. For example, reagents for running CPK tests cost only 14 cents per test at current prices. Since it works with ultra-micro quantities only 100 microliters of reagent and 10 microliters of serum are required for each test. The instrument is ideal for either routine or stat work permitting four different tests to be run on a stat sample in about 20 minutes.

In operation, it is only necessary for the operator to load the samples, place the reagents in position and press the test selector. The apparatus is push-button programmed for LDH, ALKP, SGOT, SGPT and CPK tests. All test parameters are present and results are printed out once each 24 seconds directly in units per liter. If curvature (i.e., non-linearity in the rate of change of absorbence) is excessive or absorbance is out of range, the printout is in red and an error message given. Changeover from one test to another can be accomplished in less than 30 seconds. Other enzyme substrates can be run with the use of an auxiliary control panel.

The instrument can measure sample activities as high as 1600 units per liter. Profiles can be run on single samples since the instrument's covered sample platter prevents evaporation and the serum pumps and the diluter never contaminate the sample with reagent. Carryover from sample to sample is reduced to less than 0.2% by a unique continuously irrigated wiping system and self-cleaning diluter.

The apparatus of the present invention uses optimum methodology and its accuracy and freedom from non-specific interferences is equal to that of the best reference method. All enzyme analyses are performed using the classical kinetic approach employing two separate reagents. The first contains the buffer, co-enzyme and auxiliary enzymes. When it is mixed with the serum, non-specific reactions begin and go to completion during a six-minute preincubation period. The second reagent contains the substrate for the enzyme test involved and triggers the specific reaction whose rate is catalyzed by the serum enzyme to be measured.

The instrument will operate at any laboratory ambient temperature. A thermo-electric heat pump regulates the temperature of the reaction in the curvette or photometric sample cell and either cools or heats as required. A thermometer which monitors reaction temperature is visible at all times. The photometer itself is unique in that it uses two hollow cathode lamps as a light source. Its sensitivity greatly exceeds that of prior art apparatus, the system being sensitive to a rate of change of absorption of $5 \times 10^{-6}$ absorbence units per second.

In operation, the following steps are automatically carried out:

a. a first reagent is pipetted into a reaction cup;

b. the sample is then diluted into the reaction cup;

c. the sample and first reagent are preincubated together;

d. a second reagent is pipetted into the reaction cup and the mixture stirred to start a desired reaction;

e. the reacting mixture is then transferred to the photometer through a thermostated heat exchanger to bring its temperature to a desired value;

f. the reacting mixture is then continuously observed and its absorbance measured over a predetermined period;

g. the rate of change of absorption is measured and displayed as a enzyme concentration or activity;

h. simultaneously with the observation of rate, curvature is computed;

i. curvature is checked to see whether it is sufficient to invalidate the rate measurement and, if so, an error message is printed out.

Samples are stored in a 40-cup platter and processed through the apparatus in a 10-cup magazine. The magazines run through a preparation portion where the steps of adding the first reagent, diluent and serum is carried out and then through a pre-incubation area to a second portion where the second reagent is added and the analysis carried out.

The kinetic reaction rate and curvature measurement and the error checking system provide features not found in the prior art. The absorbance of the reaction mixture is continuously observed over a measuring time and converted to an analog voltage linearly realted to absorbance. This signal is then converted to a pulse frequency modulated signal having a frequency linearly related to absorption. The pulse frequency modulated signal is integrated by counting pulses in a reversible counting register accumulating counts for the first half of the measuring time in one direction, then reversing the direction of counting so as to subtract the cumulate counts in the second half from that of the first half. As a result, the final net count is proportional to the average rate of change of the absorbance signal over the measuring period. Measurement in this way means that the final output is a measure of the change over the full measuring period. Clearly, this method of measurement is much superior to methods taking a reading at the beginning and end of the period and subtracting the results. With such methods which were generally used in the prior art, it is possible to obtain greatly erroneous results because of the fact that random variations in the absorbance can occur at various points in the measuring cycle due, for examle, to solid material in the sample. In addition, while the rate is being computed, an accumulation of the same pulse train in a second reversible counting register occurs in which counts are accumulated in one direction from the first quarter of the measuring time, the direction reversed and the counts accumulated in the second and third quarters in the opposite direction, the direction of counting again reversed and counts in the fourth quarter of the measuring time accumulated in the first direction, to obtain a net value proportional to the curvature of the rate. This gives a measure of its linearity. The count stored in the curvature register is compared with that in the rate register and if it exceeds a certain percentage of the rate count, an error signal is printed out. Specific means for doing this are disclosed in detail.

Computation in this manner has two beneficial effects. In the first place, as the computations are carried out simultaneously, no time is wasted. Furthermore, making the decision as to whether the rate observed is within limits, based on a percentage of the rate, is superior than prior art methods where, if an arbitrary curvature value was exceeded, the rate measurement was considered erroneous regardless of its magnitude. In addition, an indication is given as to the sign of the curvature where an excessive error exists. This gives the operator a clue as to what occurred during the measurement which causes excessive curvature, e.g., an accelerating rate or exhaustion of the reagent.

As alluded to above, the photometer of the present invention is highly sensitive and has this high sensitivity while measuring extremely small quantities. The photometer design of the present invention obtains increased sensitivity in measurement of extremely small changes in absorbance of a fluid sample at a particular wavelength of interest. It also improves the sensitivity of measurement of the rate of change of absorbance of a fluid sample over a short period of time as is desired in kinetic measurement of the rate of reactions catalyzed by enzymes. Furthermore, it broadens the dynamic range of absorbances over which a small change in absorbance can be measured, and as noted above, it does all this with small volumes in a range of 100 microliters or less.

It has been common practice in the prior art in the design of most sensitive and stable photometers for measuring small changes in absorbance of samples to achieve sensitivity and stability through the use of the double beam principle and an optical modulation system in which a beam of spectrally filtered radiation or portions of the beam from the source are alternately directed along a path thought the sample and a reference path not through the sample. The beams through the two paths are combined on a single detector to produce a periodically time-varying signal. In these prior art systems, the periodic signal is then demodulated to generate a signal which is the measure of the difference of absorbance in the sample reference paths. In the very best examples of this prior art approach to sensitive photometry, the least detectable change in absorbance is about $5 \times 10^{-4}$ absorbance unit.

The photometer of the present invention on the other hand does not require this modulation found in the prior art but still achieves a sensitivity which is an order of magnitude better than that found in prior art photometers. That is, it can regularly measure changes in absorbance of fluid samples as small as $5 \times 10^{-5}$ absorbance unit. Features of the photometer which permit achieving this result are a high stability optical design in an unmodulated double beam arrangement with a pair of silicon diode detectors used to detect a signal output and a reference output. The silicon diode detector outputs are amplified in high accuracy DC amplifiers and then followed by a silicon diode log-taking circuit. The silicon diode log-taking circuit is maintained at a controlled temperature environment. In addition, the cell itself is thermally isolated within a cavity and maintained at a predetermined temperature. Because of its thermal isolation, the sample, which is preheated on its way through the photometer cell, and the cell remain at a constant temperature throughout the measurement cycle. The sample is heated by being passed through a thermostated metal block whose temperature is controlled by a control system including a thermistor and a heat pump.

Transfer of the sample to the photometer is accomplished by a transfer system which has very low carryover from sample to sample yet works extremely rapidly with very small sample volumes. This is achieved through the combination of a cam-driven positive displacement pump, a cam-driven probe, which dips into a cup containing the sample, oscillating up and down in a controlled way to produce air slugs in between sample slugs, a cam-driven pump that squirts a measured amount of wash liquid into the cup after the sample is exhausted, and a valve which stops the sample flow through the flow cell during measurement. The wash liquid chemically conditions the system between samples and washes out carryover. The cam-driven pump momentarily reverses the flow once each sample cycle so as to dislodge any foreign matter that may become hung up in the cell. All the cams including sample pump, probe motion, wash liquid pump and valve motion are coordinated on a single shaft to make the complex interrelated motions occur in a closely timed pattern.

The apparatus includes a serum diluter which achieves good repeatability in metering an ultra-micro sample yet operates rapidly and with very low sample carryover in spite of a relatively low dilution ratio such as 10 to 1. This performance is achieved through a combination of a moving tubular probe and a cam-driven pumping system with two pistons in two cylinders and a sliding valve connected to it by flexible tubing, the actions of the moving probe and pump being coordinated so as to produce the following series of events:

a. The valve disconnects the large diluter-pump cylinder from the probe and connects it to the diluent supply. The diluter-pump piston retracts and fills the pump cylider during the next several events. Meanwhile, the sample takeup-pump piston expels a small volume of diluent to form a drop at its tip.

b. The probe moves from its rest position to an irrigated sponge wiper, then down through the sponge wiper. After the tip of the probe has passed down through the sponge wiper which wipes off any diluent drip at its tip, but before the probe reaches the sample, a sample pickup-pump piston retracts the body of the diluent in the probe to form a small air slug in the probe tip. After the probe has entered the sample, the same sample pickup-pump piston retracts the diluent further to bring sample into the probe tip, below the air slug. The probe then rises up through the irrigated sponge wiper, which wipes off excess sample from the outside and tip of the probe. The probe moves to the container in which the diluted sample is to be prepared, and decends into it. The valve moves to connect the diluter-pump cylinder to the probe and disconnects it from the diluent supply. The sample is expelled from the tip very slowly, to permit the air slug between the sample and diluent time to thoroughly scrub out the film of sample adhering to the inner walls of the probe tip.

c. After the sample and part of the air slug have been expelled slowly, the diluter-pump piston moves to expel the desired amount of diluent through the tip at a more rapid flow rate to save time, and to mix sample with diluent by turbulence. After the desired volume of diluent has been expelled, the probe moves out of the diluted sample container and back to its rest position. At the rest position, the diluter pump expels a substantial additional amount of diluent to a waste drain to wash out nearly all remaining sample adhering to the inner walls of the probe tip.

The wetting of the tip with diluent before each use and the wiping off of the excess liquid by the sponge wiper system permits metering volumes precisely by reducing carryover. Formation of the air slug separating the sample and diluent in the probe tip further prevents contamination and carryover keeping the diluent and samples separated until they are discharged into the cup. The slow expulsion of the sample followed by a rapid expulsion of diluent at the waste station further reduces carryover.

The slide valve used in the diluter pump system has a very small volume displacement and a very small leak rate achieved through the use of a guarding groove completely surrounding the ports on the sliding valve part with the groove filled with sealant liquid under a small positive pressure. Sealant liquid lubricates the sliding valve surface, seals out air leaks and prevents freezing of the sliding part when the valve is not used for a long period caused by the drying out of the liquid containing solid solutes at the margin of the slider. Also shown is a water column arrangement for obtaining the small positive pressure placed on the sealant liquid with the water column further arranged to provide cooling water to the heat pumps used in controlling the temperature of the thermostated block and the temperature of the log taking diodes.

The pipetters which add the first and second reagents to the sample have several features which increase the accuracy and flexibility of the apparatus. No reagent is stored in any of the tubes in the system, reagent being in contact only with an easily exchangeable probe tip or pipette. This permits an easy changeover of reagents by simplifying changing reagent bottles and probe tips thereby facilitating the running of different tests. An irrigated sponge is used in the same manner as for the diluter probe to wipe the tip of the pipette to insure that a precise volume is delivered, to reduce carryover and to dispose of small amounts of reagent wasted each cycle. Reagent is pipetted directly out of the bottles in which it is reconstituted from the freeze-dried state in which it is supplied.

The pipetter system comprises a mechanism that moves an exchangeable pipette between a reagent supply vial and the reaction mixture cup in a cyclic manner. The pipette is connected by a long thin flexible tube filled with air to a cam-driven displacement piston and cylinder with valves whose motion is coordinated with the probe mechanism. The cycle starts in a rest position with the probe stuck through the irrigated sponge wiper, its tip being just below the sponge but not in the reagent bottle. The steps in the cycle include:

a. probe descends into reagent;

b. pump sucks up the required reagent volume plus a small extra volume for margin;

c. probe ascends through wiper, wiping drop off outside of tip;

d. probe moves to reaction mixture cup and descends into it to a level such that after its delivery the tip will be in contact with the resulting liquid surface in the cup;

e. pump expels the required volume into cup;

f. probe ascends and returns to the sponge wiper and stops directly over it, without penetrating;

g. pump expels a volume slightly greater than the extra volume for margin, thus cleaning any carry-back that may have gotten inside the probe tip from the cup contents;

h. probe descends through sponge to the rest position above the reagent, thus wiping off any carry-back from the outside of the probe;

i. pump sucks in a volume of air required to return it to its starting conditon thus ending the cycle.

This cycle has the effect of very precise volume delivery because of wiping of the tip, and because the volume delivery does not require total clearing of the tip, since part of the extra volume for margin may "hang up" inside the probe without affecting the volume delivered.

The cycle gives very low carryover because the explusion of the extra volume as waste into the sponge wiper cleans the inside and the sponge itself cleans the outside.

The analyzer of the present invention avoids the unreliability of microswitches and the like through the use of a novel fiber optic sensing system. Light from a single projection lamp illuminates one end of a bundle of some 30 or 40 optical fibers. These fibers fan out throughout the instrument each one going to a location where the motion of one of the mechanisms is to be controlled.

At each control location, light leaves the illuminated fiber and is directed toward a sensing optical fiber. Depending on the status of the mechanism being controlled, the light is either transmitted to the sensing fiber, or interrupted so as to not enter the sensing fiber. Each sensing fiber goes from its control location to a common circuit card where it illuminates a single photodetector. A substantial amount of light is transmitted to the photodetector only when light from the illuminated fiber is transmitted to the sensing fiber. The photodetector senses the light and sends its signal to an amplifier and trigger circuit, creating a logic-level signal which depends upon the status of the mechanism being controlled.

Just as many illuminated fibers are illuminated by a single projection lamp, many sensing fibers terminate on a single circuit card, where the photodetectors, amplifiers, and trigger circuits can be implemented using integrated solid state circuits.

The logic-level signals are transmitted to various logic circuits whose outputs ultimately control actuators or displays dependent upon the status of the various mechanisms.

At the control locations, there are two distinctly different kinds of optical elements which terminate the optical fibers. One type is designed to sense the presence or absence of an opaque object intervening between the illuminating and the sensing fibers. It is called an object sensing terminal. Another type is designed to sense angular rotation of a shaft. It is called an angle sensing material.

Object sensing terminals are small one-piece molded transparent plastic collimators which are cemented to the ends of the fiber optics in such a way that the light emanating from the attached end of the illuminating fiber is approximately at the focus of the distal spherical lens surface of the terminal. The light emitting into the solid plastic body of the terminal diverges toward the lens surface, and upon entering the air, it is approximately collimated.

An identical terminal cemented to the input end of the sensing optical fiber, receiving collimated light at its lens surface from the correct angle converges the light and images it at the end of the sensor fiber, thus, transmitting the collimated light it receives into the sensing fiber.

The object sensing materials of the illuminating and sensing optical fibers are mounted with lenses facing each other so their axes of collimation are approximately colinear. They may be up to several centimeters apart, the maximum distance being limited by loss of light transmission caused by spreading of the partially collimated light beam to an area larger than the lens of the sensing fiber terminal.

Passage of an opaque or diffusing object between the two terminals interrupts the collimated beam of light passing between them, causing a logic-level signal change in the sensing circuit. The optical design of the object sensing terminal is such that its focal ratio is similar to that accepted or illuminated by the optical fiber, and its focal length is such that the optical fiber subtends a field angle conveniently large so that angular alignment of the optical axes of the two terminals need be no more precise than is conveniently attainable by a simple mechanical clamping of the outer surface of each terminal, so that no critical adjustments are necessary.

The angle sensing terminal for detecting the angular position of a rotating part consists of a small one-piece molded transparent plastic spherical auto-collimator lens with provision for two optical fibers cemented to it such that the end of each fiber is at a point conjugate to the other fiber's end on opposite sides of the focus of the lens, the optical axis of the lens being oriented in a plane perpendicular to the axis of rotation of the rotating part. One optical fiber is the illuminating fiber, the other the sensing fiber.

The angle sensing terminal is used in connection with a small reflector mounted on a rotating part whose angular motion is to be sensed. As the rotating part moves, it brings this reflector into the collimated light beam emanating from the illuminating fiber, through the terminal's lens. As the reflector rotates with the rotating part, it reaches a position such that the reflection from it re-enters the angle sensing autocollimator at just such an angle as to be transmitted efficiently into the end of the sensing fiber. At this particular angle, a strong optical signal is transmitted to the sensing photodetector causing a logic-level output from the sensing circuit.

To avoid the need to control the angle of mounting of the reflector on the rotating part in any other plane than the one perpendicular to the axis of rotation of the rotating part, the reflector may be designed to be a retro-reflector in the plane parallel to the axis of rotation. In the embodiment use, this is achieved by making the reflector a molded transparent plastic part with a flat surface toward the angle sensing terminal and, on the side away from the terminal, an array of flat surfaces which form vee-grooves acting as roof-reflectors by total internal reflection, the roof edges of the reflector being oriented perpendicular to the axis of rotation of the rotating part.

With this type of retro-reflector, minor maladjustments of the angle of the sensing terminal or reflector in the plane parallel to the axis of rotation cause no effect, while the sensitivity to angle in the plane perpendicular to the axis is essentially undiminished.

The optical design of the angle sensing terminal is such that the focal ratio of the auto-collimator is similar to that illuminated or accepted by the optical fibers, while the focal length is chosen so that the diameter of the end of the optical fiber subtends a field angle in air about half the angle within which it is desired to sense the rotation of the rotating part.

The angle sensing system can be made unusually sensitive to angular rotation by making its field angle relatively small. In a system using both object-and angle-sensing terminals and one diameter for all optical fibers, this is achieved by making the focal length of the angle sensing terminal relatively long. Because the reflected beams' angle changes at double the rate of rotation of the reflector, and because the physical length of the auto-collimator is shorter than its focal length in air by the ratio of the refractive index of the transparent material to the refractive index of air, the angle sensing system can detect rotation to better than $\pm 1°$ sensitivity in an apparatus no longer than 3 centimeters fusing a 1 millimeter diameter fiber. Especially important is that the rotating part need not have any large radius to achieve this sensitivity. The radius at which the reflector is mounted is of no importance, and the distance from auto-collimator lens to reflector is not critical as long as too much vignetting does not occur. Because of the high directionality of the terminals on the sensing optical fibers, diffuse illumination from the environment is seldom a practical problem in the embodiments described because not too much enters the sensing terminals at precisely the right angles.

An outstanding advantage of the fiber optic sensing system over other systems such as microswitches, magnetic reed switches, etc., is that once installed and adjusted, its operating margins can be easily checked. For example, in the embodiment described, an assembler or field service technician can connect an indicating unit to the sensing circuit card which displays the states of the logic-levels of all outputs. The strength of illumination in the common beam from the source illuminating all the fibers can be increased or decreased above and below the nominal value by raising or lowering the lamp voltage or by inserting or removing filters from the beam.

If all the sensors continue to function correctly at the extremes of illumination tested, then on restoring the illumination to its nominal value, margins for degradation of optical transmission, or increase of stray illumination from the environment, have been established. This is extremely difficult to do when any kind of mechanical or magnetic sensing systems are used.

The operation of the whole system including the pipetters, diluters, transfer system and measuring system is all carried out under the control of a solid-state logic arrangement. Separate timers are provided for the preparation unit portion where the first reagent, diluent and serum are added for the analyzer section where the second reagent is added and the reacting mixture transferred to the photometer and measured. All operations involving mechanical movements are accomplished by motors having on their shaft a retro-reflector such as that described above with the end of the motor cycle being controlled in response to an output from the angular sensing device. This ensures that all cycles stop at the same point each time avoiding any possibility of the system getting out of synchronization.

Various other features of the system are disclosed including the use of spacer magazines to automatically stop the apparatus when it is desired to change over from one test to another.

BRIEF DESCRIPTION OF THE DRAWINGS

FIG. 12a is a tabulation designated Table IV helpful in understanding operation of the apparatus.

FIG. 25 is a similar illustration of the hyraulic portion of the transfer system which provides oscillating probe motion.

FIG. 30a is a section on line 30a—30a of FIG. 30.

FIG. 31 is a plan view of the analyzer of FIG. 1 illustrating the location of various mechanical elements.

FIG. 32 is a section on line 32—32 of FIG. 31 illustrating the diluter drive.

FIG. 33 is a section on line 33—33 of FIG. 32.

FIG. 34 is a view along the section line 34—34 of FIG. 32 illustrating a spring biasing arrangement for the diluter probe.

FIG. 35 is an exploded view of the cams used for controlling a motion of the diluter probe.

FIG. 36 is a developed view of one of the cams of FIG. 35.

FIG. 39 is a section on line 39—39 of FIG. 31 illustrating belt drives and stepper drives for moving magazines through the apparatus of FIG. 1.

FIG. 40 is a section on line 40—40 of FIG. 31 showing a further view of one of the belt drives.

FIG. 41 is an additional sectional view illustrating from a different angle the stepper drive and showing in more detail the construction of the magazines.

FIG. 42 is a sectional view on line 42—42 of FIG. 41 illustrating in more detail the stepper drives of FIG. 39.

FIG. 48 is a sectional view taken along the line 48—48 of FIG. 31 illustrating the pipetter of the analyzer of FIG. 1.

FIG. 49 is a detailed sectional view of the arm of FIG. 48 which supports the pipetter.

FIG. 50 is a sectional view along line 50—50 of FIG. 48.

DETAILED DESCRIPTION OF THE PREFERRED EMBODIMENT

The kinetic enzyme analyzer of the present invention is capable of performing a plurality of different tests on serum and other samples. These tests include the quantitative determination of enzymes known by the common names LDH, SGOT and SGPT, CPK, and alkaline phosphatase, as well as other substrates, by enzyme methods. In general terms, each of these tests requires that one or two reagents be mixed with a diluted serum sample to obtain a reaction which results in a change in photo-absorbance with time, the change in absorption being measured by a photometric system. More details as to the various tests and the reagents used will be given below.

Figure 1:
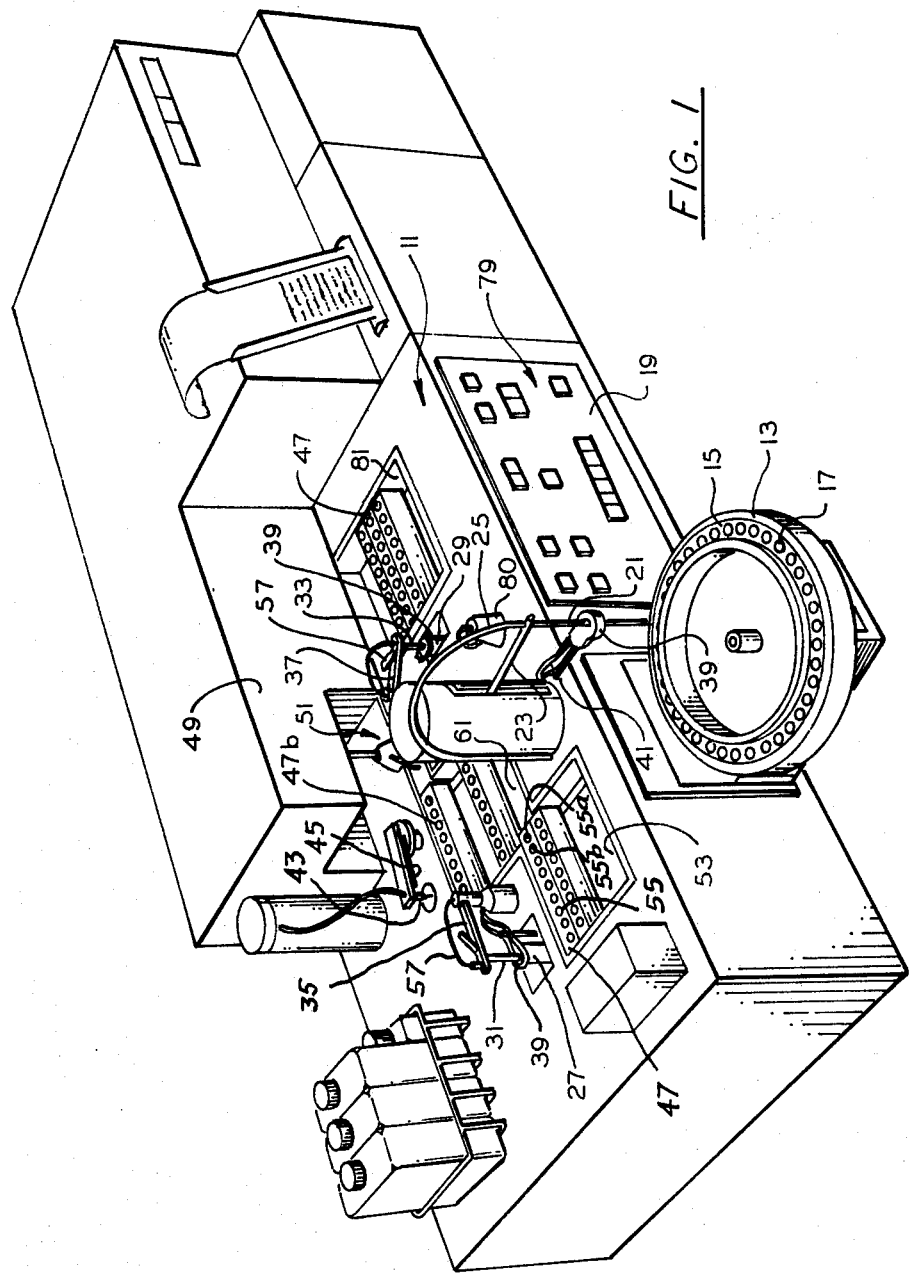
FIG. 1 is a perspective view of the analyzer apparatus of the present invention.

A perspective view of the apparatus of the present invention is shown on FIG. 1. The apparatus, designated generally as 11, includes a sample table 13 containing a 40-cup platter 15 in which standard disposable polystyrene cups 17 containing serum samples to be treated may be placed. As shown in the drawing, the tray and other components are mounted at the front of an enclosure 19 of the overall apparatus. Above the tray 13 is a diluter probe 21 mounted on an arm 23 for controlled vertical and rotating motion. Attached to the probe 21 is a tube 25 for providing diluent liquid in a manner to be described below. The tube 25 leads to appropriate pumps and valves. The reagents for use in the test are contained within changeable reagent bottles. A first reagent bottle is designated 27 and a second reagent bottle 29. Disposed above each of the reagent bottles are respective interchangeable pipettes 31 and 33, preferably of glass or similar material. The pipettes 31 and 33 are mounted respectively to arms 35 and 37 in a removable fashion. The arms 35 and 37 are adapted for vertical and rotational motion in a manner to be more fully described below. Associated with each of the pipettes 31 and 33 and with the probe 21 is a sponge 39 contained within an annular enclosure. Tubing 41 is provided to each of the enclosures to provide irrigating water to constantly clean the sponges. A suction drain is also provided to each enclosure to remove the irrigating water. In this manner, each time a pipette or a probe is vertically moved through the sponge to pick up a reagent or serum sample, it is cleaned. Also shown is a stirrer 43 mounted on an arm 45 also adapted for vertical and rotational motion.

Samples being processed through the apparatus are contained within magazines 47 visible within various portions of the apparatus. Particular magazines are designated 47a, 47b, etc. The photometric equipment which is not shown in detail on FIG. 1 is contained within the enclosure 49. The samples which are provided to the photometric equipment are picked up and transported by transfer means designated generally as 51 to be described in more detail below.

Figure 2:
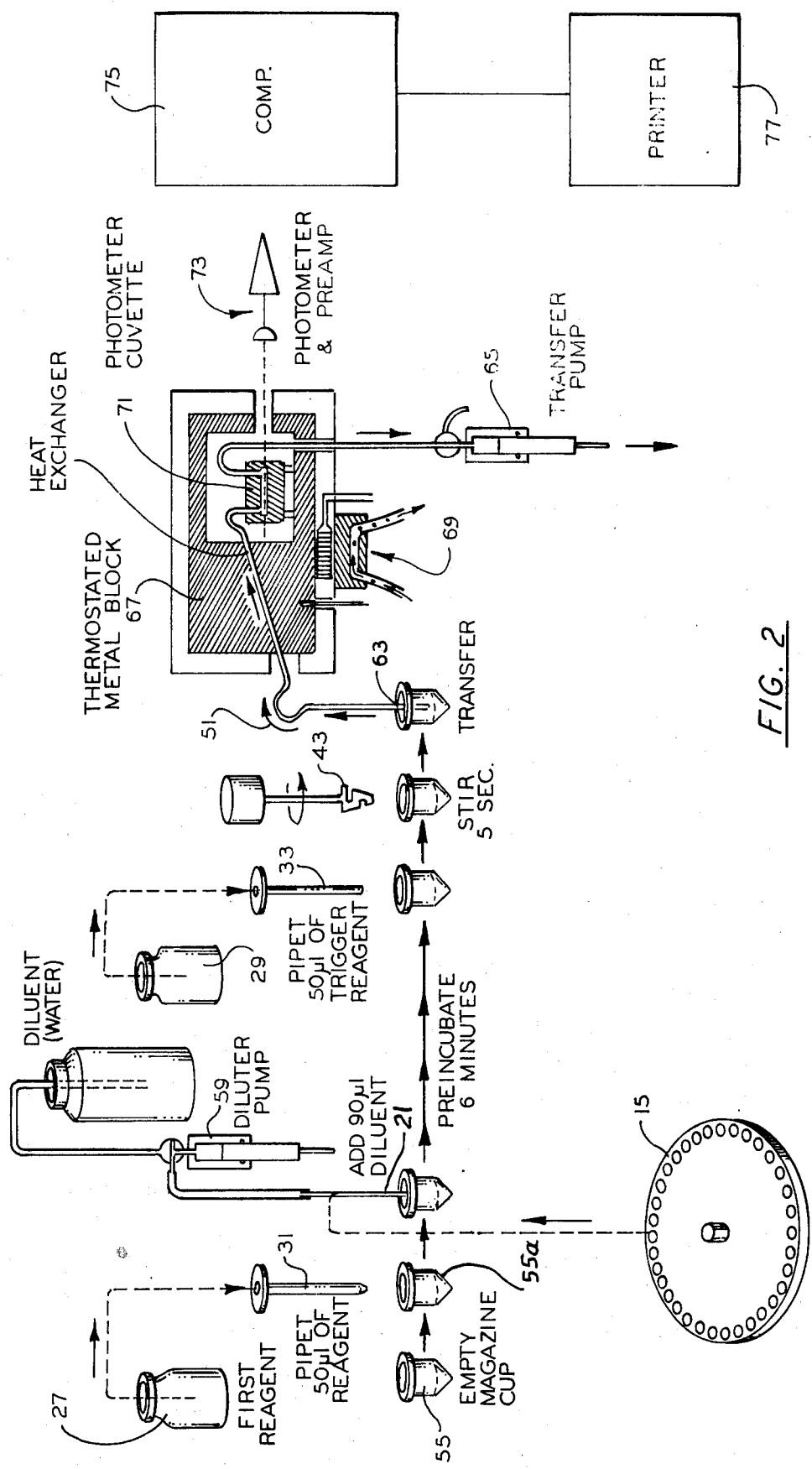
FIG. 2 is a schematic representation partially in perspective view of the steps carried out by the analyzer of FIG. 1.

Further understanding of the operation of the apparatus may be had from examining FIG. 1 along with FIG. 2. With the aid of these two figures, the basic steps followed in carrying out a test will be described.

Up to forty serum samples may be loaded into the 40-cup platter 15. The proper reagents for the test to be performed are placed in reagent bottles 27 and 29 and the bottles are put in place. Clean pipettes 31 and 33 are installed. Four clean magazines 47 are loaded at position 53. Drive means at this position drive the magazines so that at least one magazine is always fully to the rear in a position where it can receive reagent from pipette 31. As illustrated, each of the magazines contains ten reaction cups 55. Particular cups being designated 55a, 55b, ... from right to left in FIG. 1. With the magazine 47a in the position shown, the first step of the process comprises pipetting 50 microliters of reagent into the empty magazine cup 55a. The arm 35 is caused to move down submerging the pipette in the reagent 39 to pick up 50 microliters of reagent. The arm 35 is then raised and rotated to a position above the empty cup 55a and then lowered into the cup after which the reagent is discharged into the empty cup. At the end of the delivery of reagent, the pipette tip is below the surface of liquid in the cup 55a. Pipetting is accomplished in essentially the same manner as done manually with a finger pipette. As illustrated, appropriate vacuum control lines 57 are connected to each of the pipettes 31 and 33 for this purpose. The system controlling the picking up and release of reagent will be described in greater detail below.

While the first reagent is being placed in a cup 55a, the diluter probe 21 is lowered into one of the sample cups 17. Typically, only from 20 to 100 microliters of serum need be in each cup. A diluter pump 59 is operable to draw out of the cup 10 microliters of serum. Prior to drawing in serum, a small air bubble is first drawn in. The arm 23 is then raised and rotated to a position over the cup 55a whereupon the probe 21 descends into the cup with its tip below the surface of the liquid therein and 10 microliters of serum along with 90 microliters of diluent (water) is pumped by the diluter pump 59 into the cup. After this, the probe 21 ascends and the magazine 47a is advanced one position (to the right in FIG. 1) to cause the cup 55b to be positioned to receive the first reagent and another serum sample placed therein. Simultaneously therewith, platter 15 is rotated to the next serum sample cup. The process of adding reagent and serum plus diluent to each of the empty magazine cups 55 continues until all 10 cups are filled, or until the magazine is cleared away by another control signal.

Thus magazine 47a is progressively transferred to the area 61 where it is then moved completely rearward to a position shown on the figure as occupied by magazine 47b. As illustrated by FIG. 2, operation is such that there is a pre-incubation period of a minimum of 6 minutes between the time when the serum, diluent and first reagent are mixed until the addition of the second reagent by pipette 33. This pre-incubation period allows pre-heating of the mixture, and completion of some reactions before the next state of the analysis.

With the magazine 47b in the position shown, the arm 37 is lowered causing pipette 33 to enter the reagent bottle 29 to pick up 50 microliters of a trigger after which it is raised and rotated to a position over the first cup 55a in magazine 47b, into which it descends. The trigger reagent is then pipetted into the cup 55a containing the serum previously diluted with water and mixed with the first reagent. Once this occurs, the stirrer arm 43 is raised, rotated and lowered into cup 55a with the stirrer 43 rotating to stir the reagents and serum to obtain adequate mixing. As indicated in FIG. 2, stirring continues for approximately 5 seconds. The magazine 47b is then advanced one cup spacing to the right. As the magazine is advanced, cup 55a moves into position below the transfer means 51. The sequence is set up to permit an incubation time of at least 25 seconds after pipetting of the trigger reagent and before absorbance measurement begins.

The transfer means include a probe 63 which is mounted for vertical motion, in a manner to be more fully described below, and is coupled through a line passing through the photometric apparatus to a transfer pump 65. The transfer pump is operated and the probe 63 moved up and down in a oscillating manner which causes a plurality of samples of the contents of cup 55, separated by bubbles or slugs of air to be picked up. A plurality of short sample slugs are picked up and then a long sample slug which is the one on which the measurement is made. The sample passes through a thermostated metal block 67 having associated therewith a thermoelectric heat pump 69 capable of either heating or cooling so that the temperature of the sample can be maintained to within ± 0.2.° C of a desired temperature and regulated to ± .05° C.

The large sample slug now at the proper temperature for measurement is transferred to the photometer cuvette 71 where it remains for about 12 seconds. During the last 8.8 seconds of the 12 second period, the photometer indicated schematically along with its preamplifier 73 measures the absorption of the reaction mixture. During this time, the average rate of absorption change and the curvature of absorption are measured simultaneously. The actual value of the absorption is checked against high and low thresholds throughout the measuring period. This is all carried out by computing apparatus designated generally as 75 which will also be described in detail below.

The enzyme activity of the serum sample is computed and printed out directly in international units/liter [u/l] by a printer 77. If the curvature is excessive or the absorption out of the expected range, the printout is in red and annotated with a warning message.

Test selection and automatic operation are initiated by pressing appropriate switches on a control panel 79 shown in FIG. 1. These control the various computation parameters, wavelength used in the photometer, etc., as will be fully described below. As noted above, typically 100 microliters of serum may be poured into each of the cups 17. This will be sufficient for running several tests. This is particularly true since the serum diluter causes negligable contamination of the serum which remains in the cups due to its washing by the sponge 39 and furthermore by irrigation which is carried out after each sample cycle. This occurs with the probe 21 positioned over a receptacle 80. After depositing the serum diluent in a cup, the probe 21 is moved to this position and flushed with additional diluent water. Contamination within the transfer system is also avoided by flushing the complete system with a washing liquid after each test. This portion of the system not shown in detail on FIG. 1 and 2, will be described in detail below when discussing the transfer system.

The system is capable of performing tests on 40 samples in 22 minutes. This includes 6 minutes of preincubation plus 16 minutes for 40 samples at a rate of 150 samples per hour. When running CPK tests, the total time is 2 minutes longer because these tests require an extra 2 minute incubation after triggering and before measurement to accommodate their lag phase.

As is evident from the discussion above, test change is quite simple. It is only necessary to replace the reagent bottles 27 and 29 and their associated pipettes 31 and 33 after which a different test selector button on the control panel 79 may be pressed. Much of this simplicity results from the use of water as the serum diluent in all tests. Since the reagent pipettes work on the same principle as a manual thumb operated pipette only the replacement tip touches the reagent with no reagent being present in the pumps or tubes and thus no flushing cycle is required.

Furthermore, the analyzer of the present invention has a convenience feature unique among automated analyzers. Its serum diluter and first reagent pipette can prepare samples for preincubation almost twice as fast as the photometer measures. A full platter of 40 samples can be loaded into the preincubator area 61 in only 10 minutes. Ten minutes later, another platter of 40 samples can be started through. This can be repeated and the loading of 200 samples can be done in about 40 minutes. The first result is produced 7 minutes after loading begins and 200 results are available in less than 1½ hours. During this period, only intermittent attention of the operator is required to replenish reagents. Replenishing reagents for the same test is done by replacing the vial only, which takes only a few seconds. When operating in this manner, magazines full of prepared samples move into the preincubator area 61 faster than the measuring system takes them out. For this reason, the preincubator area 61 is designed to store up to eight magazines so that it can act as a buffer between sample preparation and analysis. Magazines 47 after all tests are completed are transferred to the area 81 where they are removed and washed by the operator.

The analyzer of the present invention also has capabilities of running two to five enzyme tests on the same set of serum samples. When operating in this manner, the same platter of samples makes several complete revolutions. At the beginning of each revolution, the operator changes the first reagent for the new test. The second reagent is changed to that required for the same new test after the first test is fnished and before the set of magazines with the new test gets to the second pipette. In order to ensure that the changeover is made at the proper time, a spacer magazine is used. This is a dummy magazine with no cups. The spacer magazine is placed between the magazines representing the two different sets of tests. This magazine is arranged so that its passage into the preincubation area 61 is sensed and the exit gate behind it is closed preventing magazines containing the new test from passing through the second reagent pipette until the operator has had a change to change the second reagent to that required for the new test. After doing so, he then presses the test selector button and an analyzer gate control on control panel 79, opening the exit. This can all be accomplished in less than a minute. Through this simple measure, the use of proper reagents for each test when multiple tests are run is ensured. Thus, without any significant loss in time and with almost no chance of error due to using wrong reagents, a plurality of different tests may be made to follow one another. The results of these tests will be enzyme profiles of single 100 microliter samples done very rapidly. A profile of three different enzyme tests on a platter of 40 samples can be run in less than an hour.

The analyzer of the present invention is also capable of running emergency samples in a "stat" mode. When it is desired to run in this mode, the analyzer can be put on standby, in which condition, it is warmed up with its diluter and reagent pipettes idle but ready. To run a stat sample from this condition, the operator starts an empty magazine 47 through the system, obtains the reagent vials from the refrigerator, places them on the instrument and introduces the sample into the next magazine. A stat takes 8 minutes for most tests and 10 minutes for CPK. Sampling can be done directly from a cup 17 on the platter or may be done from a test tube of serun as desired. The diluter probe is designed so that it can reach the bottom of a 100 microliter test tube to accommodate operation of this nature. If stat profiles are to be run, i.e., if more than one enzyme test is to be run on a single sample, the operator uses a new magazine for each test with spacer magazines between, changing reagents and test selector buttons as required. To run 4 tests on one stat sample in duplicate takes 15 minutes, for most tests or 17 minutes if one of the tests is CPK. The printout for each sample is a line containing a platter number, an incrementing sequence number, the test name, and the result in units per liter. If an error condition has been detected, the line is in red, with a message indicative of the type of error.

Lines of printout are grouped in blocks of 10, corresponding to magazines. Unlike many instruments, the printout is "right side up," that is, the first sample is at the top of the printout, the last at the bottom. Since platters of 40 samples are used, the instrument adapts well to a wide variety of sample identification systems which may already be installed in the laboratory.

All the enzyme methods for the analyzer of the present invention have been adapted to the particular volumes shown in the FIG. 2 legends. The final end volume is 200 microliters. Roughly half the end volume is water diluent, while the first and second reagents each comprise a fourth of it. One twentieth is serum.

This overall serum dilution factor of 20X is well above the level at which undesirable effects of non-linearity upon further dilution can be detected.

Figure 3:
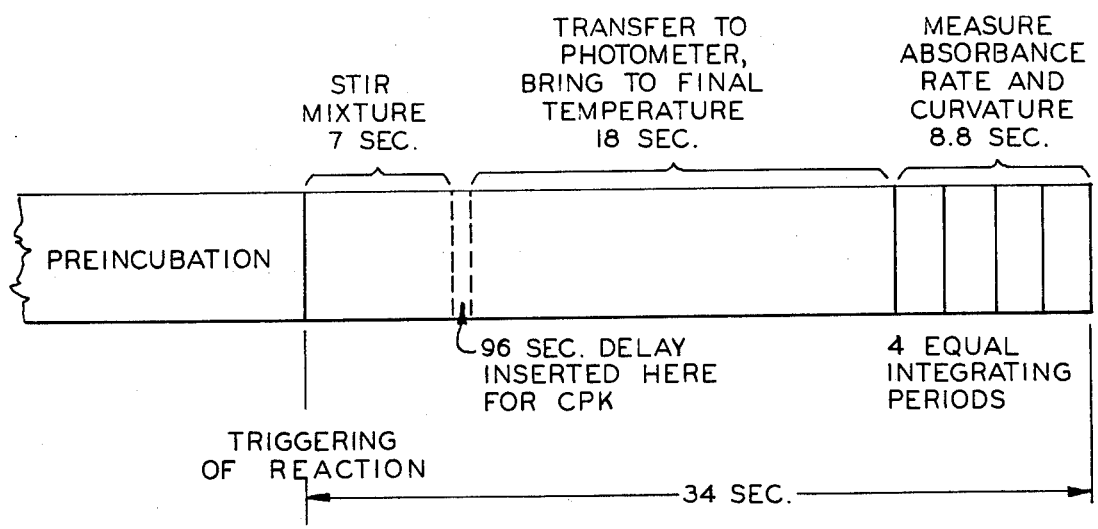
FIG. 3 is a timing diagram illustrating the timing in the operation described in FIG. 2.

FIG. 3 illustrates the details of timing of the measurement process. The overall time from triggering to completion of measurement is only 130 seconds for CPK and 34 seconds for other tests. After preincubation for a minimum of 6 minutes, during which non-specific substrates are exhausted, the reaction mixture is stirred for 7 seconds, then transferred to the photometer through the heat exchanger. After 18 seconds for transfer and thermal equilibration, the 9 second measuring period begins. The absorbance is observed and integrated continually during four equal integrating periods. The four integrals are used to digitally compute the slope and curvature of absorbance versus time.

For CPK, which has a lag phase, an additional 96 second delay is introduced between stirring and transfer. It is this combination of large dilution factor and very short overall reaction time which gives the analyzer linearity at higher enzyme activities than any other automated analyzer.

The various sub-systems involved in the above described analyzer will now be described in detail after which the manner of their control by the electronic logic in the analyzer will be described with the aid of appropriate logic diagrams.

LOGIC AND CONTROL

Figure 4:
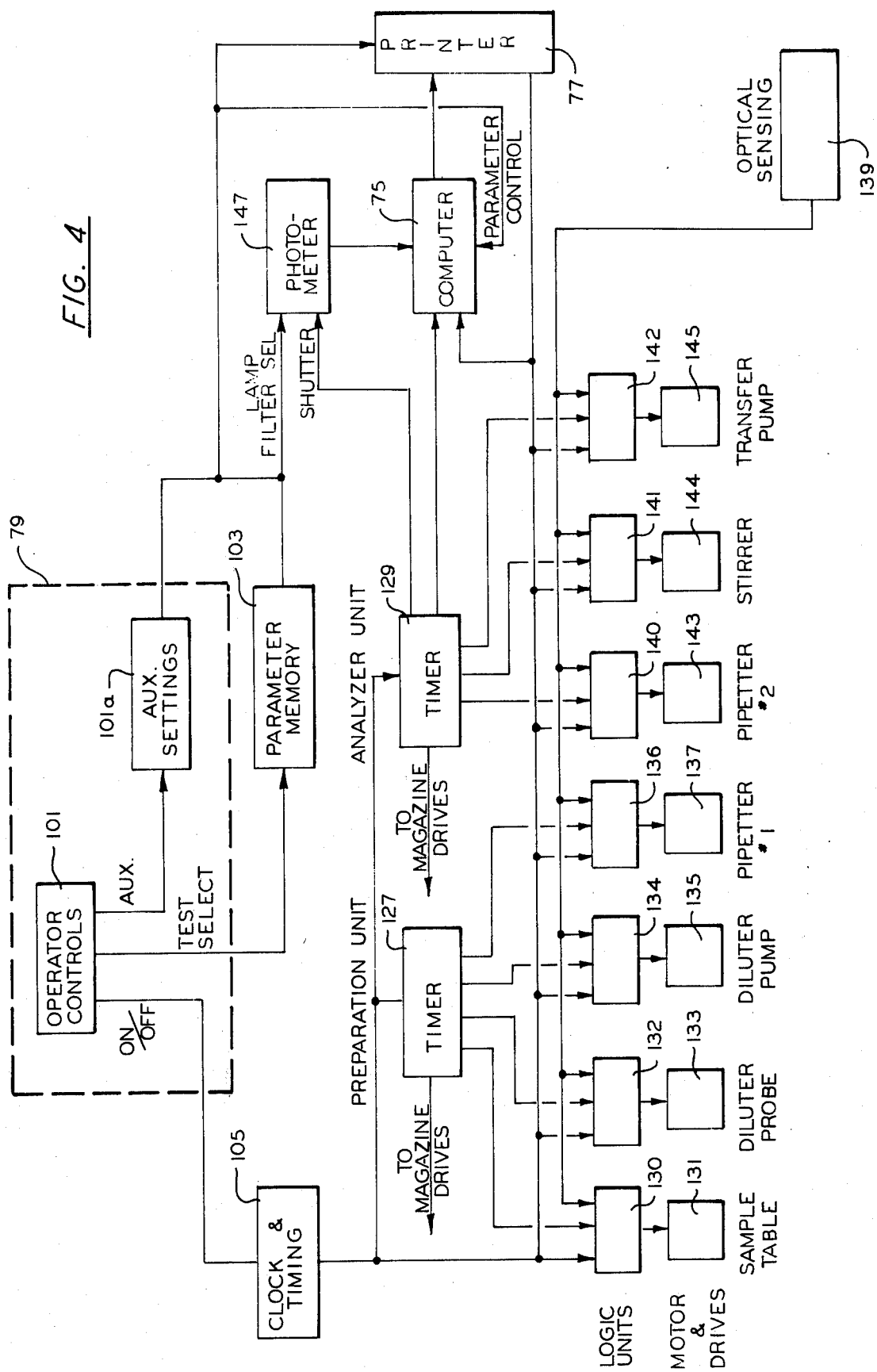
FIG. 4 is a block diagram illustrating the logic arrangement of the analyzer of FIG. 1.

FIG. 4 is a simplified block diagram giving an overall view of the control and logic associated with the analyzer of FIG. 1. In essence, the analyzer can be broken down into what are logically two separate units. These units comprise a preparation unit in which the first reagent is added to the magazine cup and the sample picked up and diluted. In other words, with reference to FIG. 1, this portion of the system is the diluter probe 21 and its associated equipment and the first pipetter 31 and its associated equipment. The other portion is the analyzer unit which includes the rest of the apparatus. That is, it includes the second pipetter 33 and its associated equipment, the stirrer 43 and the transfer means 51 along with the photometer system, computer and printer. The area 61 between these two sections acts as a buffer. The apparatus would operate equally well as two separate units with the magazines transferred by hand from one to the other. However, their combination with the buffer 61 between facilitates smooth automatic operation.

Referring now to FIG. 4, there is illustrated a block 101 designated "operator controls." The complete operator panel will be described in detail below. For the purposes of FIG. 3, only a few of the functions of the control are indicated. These include the on-off function, the test selection function, in which one of the above noted tests is selected, and an auxiliary selection which permits setting in auxiliary parameters via an auxiliary panel shown on the figure as block 101a. Selection of one of the standard tests will result in an input to a parameter memory 103 which will then provide the proper parameters for that test as outputs to the various other units. Alternatively, similar outputs are provided by the auxiliary settings of block 101a if an auxiliary test is selected. Turning on the machine will start up a clock and timing unit 105. Clock and timing unit 105 provides a plurality of clock outputs at different frequencies to various parts of the system.

Figure 5:
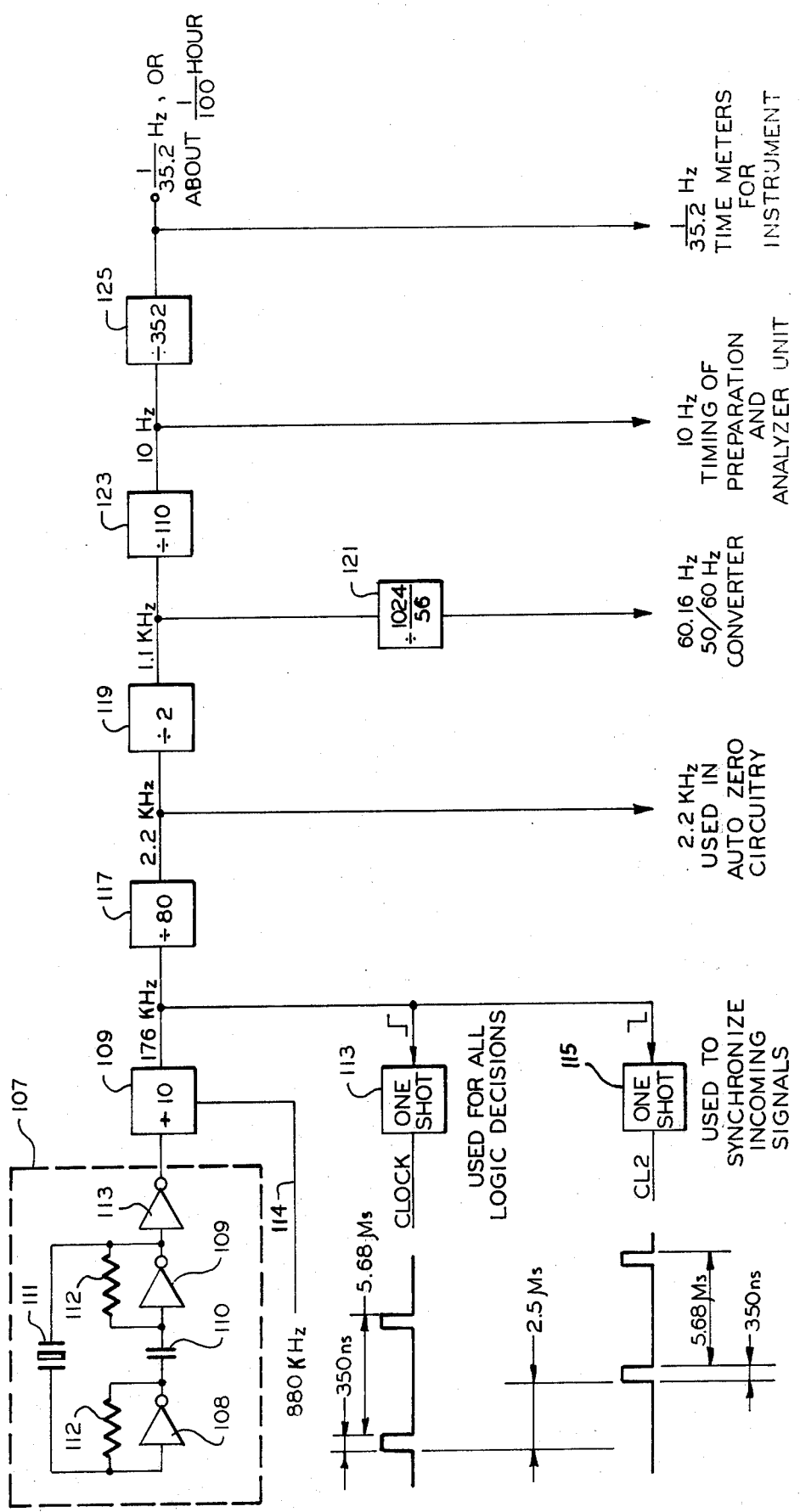
FIG. 5 is a block diagram of the clock used in FIG. 4.

FIG. 5 illustrates in schematic block diagram form the construction of the clock 105 of FIG. 4. Shown, is an oscillator 107 made up of first and second inverters 108 and 109 coupled in series with a capacitor 110 between and having a crystal 111 in a feedback path around the two inverters. Also included is a resistor 112 feeding back around each of the inverters. The oscillator output from inverter 109 is then inverted by a further inverter 113. As indicated, the crystal can be a 1.76 mhz crystal to provide an output at that frequency from the oscillator. The oscillator 107 output is divided by 10 in a binary dividing stage 109a of conventional design to obtain an output at 176 khz. From one of the stages in this divider, an output frequency at 880 khz on line 114 is taken off. The 176 khz output is provided to a one-shot 113 and a one-shot 115. The first one-shot 113 responds to the leading edge of the pulse and is used for logic decisions. The second one-shot 115 responds to the trailing edge of the pulses and is used for synchronizing incoming signals. The 176 khz is divided by 80 in a further dividing stage 117 to obtain a 2.2 khz output which is used in auto-zero circuitry to be described below. This frequency is also divided by two in a dividing stage 119 to obtain a 1.1 khz output which is further divided by 1024/56 in a divider 121 to provide a 6.16 Hz output for use in a 50 to 60 Hz converter when the unit is to be used in Europe where a 50 Hz standard frequency is available. It is also divided by 110 in divider 123 to provide a 10 Hz output used in the timing of the preparation and analyzer units. Finally, it is divided by 352 in a dividing unit 125 to provide an output at 1/35.2 Hz or about 1/100th of an hour used for time meters for the instrument.

Returning to FIG. 4, the output of the clock and timing unit 105 of FIG. 5 is shown as being provided to various parts of the system. Although shown as a single line, it will be recognized that the appropriate lines of FIG. 5 having thereon different frequencies will be provided to these different units as required.

As noted above, the machine of the present invention is logically two separate devices, i.e., a preparation unit and an analyzer unit. The preparation unit portion of the apparatus has associated therewith a timer 127 which has an input from the clock and timing unit 105 and counts through a timing cycle providing outputs to carry out all the necessary preparation unit functions. A similar timer 129 is provided for the analyzer unit.

Consider first the operation of the preparation unit. The preparation unit must operate the first pipetter 31 to transfer the first reagent to a magazine cup, e.g., 55a, and then must pick up a serum sample from a cup 17 in the platter 15 of FIG. 1 and 2, transfer this sample to an empty magazine cup 55a and add diluent thereto. Shown associated with the timer 127 are four functional units. Each of the functional units is made up of a logic unit and a motor and drive. Thus, there is shown for the sample table, a logic unit 130 and motor and drive unit 131. Similarly, for the diluter probe, a logic unit 132 and motor and drive 133 is shown. For the diluter pump, a logic unit 134 and motor and drive 135 is provided and for pipetter No. 1, a logic unit 136 and motor and drive 137. Each of the logic units 130, 132, 134 and 136 is shown as having inputs from the clock and timing block 105, from the timer 127 and from an optical sensing block 139.

Operation can best be explained by a simple example. Assume that the sample tray is properly positioned with a new sample ready and that the first reagent has been transferred to the reaction cup. The function now to be carried out is that of picking up the sample. As will be seen below, timer 127 is preset to run through a fixed cycle of operations. With the diluter probe 21 of FIG. 1 at its rest position over the irrigation receptacle 80 of FIG. 1, an output of the timer will be provided to the logic unit 132 to provide an output therefrom to cause its associated motor to turn and cause the arm 23 to be rotated and lowered into the sample cup 17. The mechanical mechanism which causes this movement will be described in detail below. As the probe is being lowered, the timer will also provide an output to the logic unit 134 to cause its asssociated motor and drive to operate the diluter pump to draw in a small air bubble. When the probe is down into the cup, the timer will provide an output to stop the motor associated with the probe for a sufficient period of time to permit the diluter pump to draw in the required amount of serum sample. The motor is then started again by the timer unit and the arm 23 raised and rotated to a position over the magazine containing the cup 55a. Proper timing signals are provided from timer 127 to stop and lower the probe into the cup and to then cause the diluter pump to discharge the serum sample along with the required amount of diluent. The motor then continues its travel and raises the arm bringing it to the irrigation receptacle 80 where additional diluent is pumped out to wash out the probe. This is all carried out with proper timing signals being provided from the timer 127 to stop and start the probe motion and to stop and start the action of the diluter pump. In similar fashion, appropriate timing outputs to the logic unit 136 associated with pipetter No. 1 are provided to cause its motor and drive 137 to operate properly. The pump for enabling the first pipetter to draw in and discharge reagent is included with the diluent pump and operates in response to appropriate inputs to logic unit 134 and motor and drive 135. Once the first reagent, serum and diluent are all in cup 55a, timer 127 provides an output to a drive, (not shown for sake of simplicity) to advance the magazine to place the next cup in position.

Within a cycle of operation of any of the motors associated with the diluter probe, pipetters and so on, stopping and starting of the motor is done in response to signals from the timer 127. However, it is essential that the motor on completion of its cycle be stopped at the exact spot that it started in order to maintain proper operation. To assure such proper stopping of the motor, optical angular sensors are used. For that reason, the logic units are shown as having an input from the optical sensing block 139. In addition, the operations described should not take place unless the magazine is properly positioned. Optical object sensors are used throughout the unit to detect whether or not a magazine is properly positioned and these signals used to enable the various logic units to carry out their functions. These signals are also used in stepping the magazines properly through the various positions shown on FIG. 1. The optical sensing will be explained in more detail below. Other outputs from the timer 127 are then used to advance the sample table 13 once the above-described sample has been taken in order to ready it for taking another sample.

The timer 129 associated with the analyzer unit operates in similar fashion, providing inputs to logic units 140, 141 and 142 to cause them to drive their associated motor and drives 143, 144 and 145. The functions of adding the second reagent, stirring the reagents and samples, and then picking up and transferring the sample to the photometer are carried out in proper sequence by outputs from timer 129. The timer also provides an output to the photometer unit 147 to open a shutter therein for the required measurement. Also shown as an input to the photometer 147 is a lamp and filter selection input which is dependent on the test being run. This input is obtained from parameter memory 103 or auxiliary settings 101a. The analog photometer output is provided to the computing unit 75 which also receives timer and clock inputs along with inputs from the auxiliary settings or parameter memory depending on the test being run. This also will be described in more detail below. The output of the computer is then provided in digital form to the printer 77 also under control of the timer 129 and of the clock 105. The printer also receives inputs from the auxiliary settings 101a or parameter memory 103 so that it will print out the specific time selected.

Figure 6:
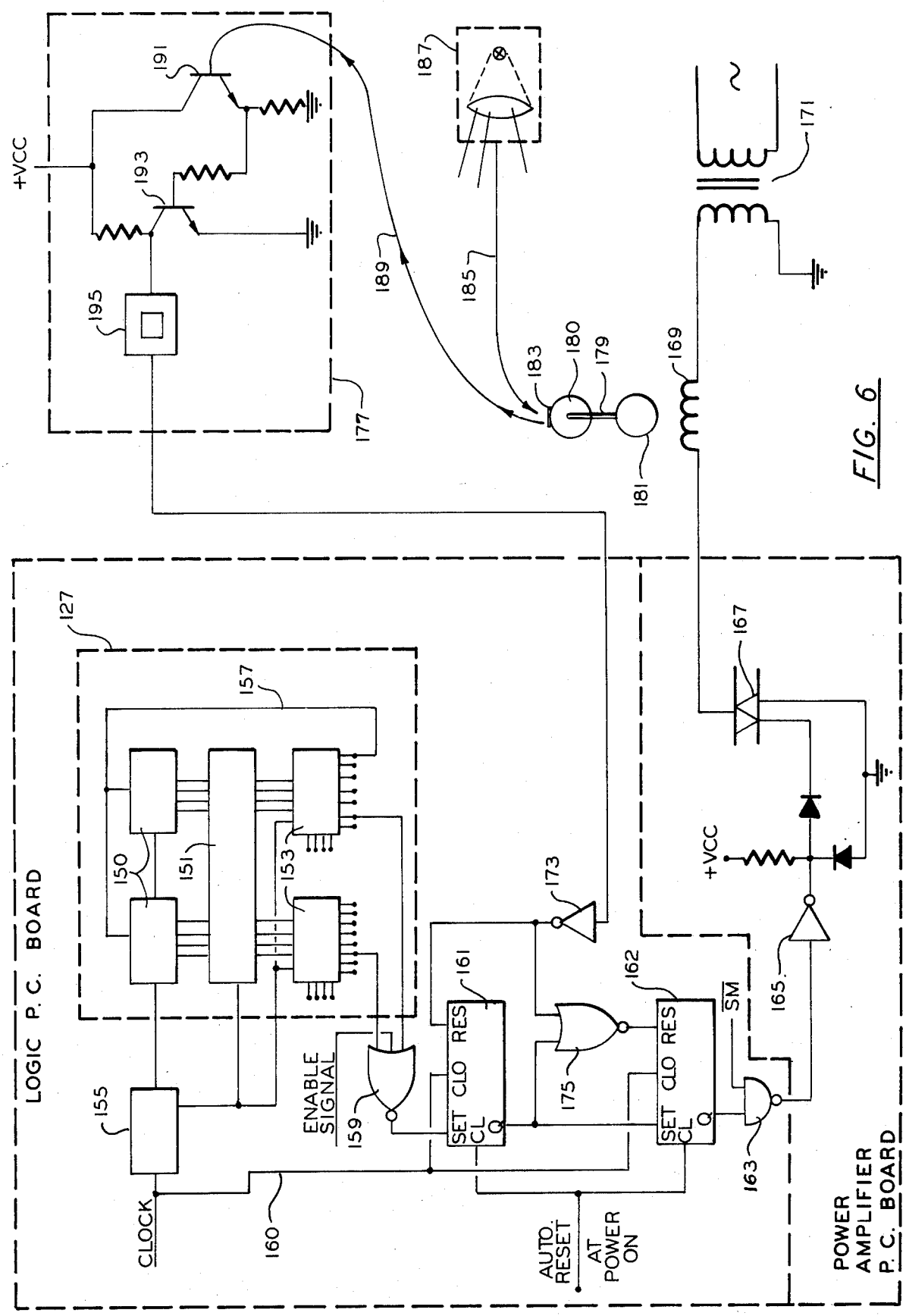
FIG. 6 is a block-logic diagram illustrating the logic used in driving the various motors used in the analyzer of FIG. 1.

FIG. 6 is a more detailed logic diagram illustrating a timer 127, a logic unit such as logic unit 136 and a motor drive. The timer 127 comprises two divided-by-16 counters 150 in series, the outputs of which are coupled to an eight-bit latch 152 used as a buffer. The outputs of the latch 151 are provided to binary to decimal decoders 153. The input to the counters 150 is the 1 Hz signal shown on FIG. 5 with the division of the oscillator output by 17,600 illustrated by the block 155. An output from the clock of FIG. 5 which occurs between the 10 Hz pulses is provided as a strobe to the latch 151. The same strobe is also provided for strobing data from the latch into the decoders 153. The arrangement of the counters 150 permits breaking up the total cycle into tenths of a second. Thus, it is possible to pick off from the decoder output any desired time period from the beginning of the cycle for use in actuating the units controlled by the timer. In the example given, 8.6 seconds is picked off. Also shown is the last output of the decoder indicating the end of the cycle provided over a line 157 to reset the counter in preparation for the next cycle. The two outputs, i.e., the 8 second and the 0.6 second outputs are provided as inputs to a NOR gate 159. NOR gate 159 will provide an output at a logic "1" level when all its inputs are "0". For this reason, as indicated, rather than taking the 8 second and 0.6 second outputs from the decoders 153, the outputs 80 and 6 are taken, (where the number equals the number of tenths of seconds). Thus, at 8.6 seconds into the cycle, these two outputs will be "0". The third input to gate 159 is an enable signal. This signal may, for example, be a signal indicating that the magazine is properly in position to permit carrying out a pipetter cycle. This signal is provided in a manner which will become clearer below. If all is in order, it will be an "0" and gate 159 will have a "1" output. The output of gate 159 is a set input to a clocked flipflop 161. With a "1" at the set input and the occurrence of a clock signal, such as that from the one-shot 115 of FIG. 5 on line 160, flipflop 161 will be set and its Q output will be go a logic "1". This output is the input to a second flipflop 162 and will thus cause it to be set on the next clock pulse. The Q output of flipflop 162 is provided as one input to a NAND gate 163. A NAND gate will have a "0" output only when both of its inputs are logical "1"s. The second input to NAND gate 163 is a signal designated SM. SM represents stop mode and is a signal generated in the apparatus if a malfunction or something of that sort occurs indicating that all operations should be stopped. During normal operation, the signal SM will be a logical "O" and thus SM will be a logical "1". As a result with flipflop 162 set, the NAND gate 163 will have two logical "1" inputs and will have as an output a logical "0". This output is inverted through an inverter 165 resulting in a logical "1" output. This output is used to turn on a triac 167. Triac 167 has its one side grounded and its other side coupled to the winding 169 of a motor 181 such as the motor associated with pipetter No. 1. The other side of the motor is coupled to one side of the secondary of a transformer 171 which has its other side grounded. The primary of the transformer is coupled to the A-C line, the transformer being used primarily for isolation and providing a 110 volt A-C output. With triac 167 on, the motor will turn.

The reset input to the flipflop 161 is coupled to the output of inverter 173. The output of inverter 173 is also one input to a NOR gate 175 having as its second input the Q output of flipflop 161. The input to inverter 173 is provided from an optical electronic converter 177. On the shaft 179 a cam or disc 180 on the motor 181 is mounted a mirror 183. The light from a fiber optic or light pipe 185 is directed onto the mirror. A source 187 provides light to the light pipe 185 and to other similar light pipes as will be described in more detail below. A second light pipe 189 is also directed toward the mirror 183 to pick up reflected light. Its other end is directed at a photo-transistor 191 which is in turn coupled to a second amplifier transistor 193 whose output is then coupled as the input to a schmitt trigger 195 for pulse shaping. The output of the schmitt trigger 195 is the output of the converter 177 which is the input to inverter 173.

The circuit can best be understood by an example of its operation. In this example, it is assumed that in carrying out its function, the motor is required to make one revolution. As will be seen below, in some cases, the motor is required to stop and to even reverse direction before completing its cycle. However, for the present example, one full turn at constant speed is assumed. At the proper point in the timer cycle, the 80 and 6 outputs from the decoder 153 are present and the output of gate 159 becomes a "1" causing flipflop 161 to be set. This in turn causes flipflop 162 to be set. It is assumed that on a previous cycle the motor had properly stopped at the mirror. That being the case, there will be a light output to the phototransistor 191. The setting of flipflop 162 will cause gate 163 to have an output at logic "0" which will be inverted in the inverter 165 causing the triac 167 to turn on and the motor 167 to begin rotation. As the motor rotates to a position where the mirror is passed, an output from the converter 177 results in a logical "0" input to the inverter 173 and the resetting of flipflop 161. Its Q output now becomes a "0". At this point, the output of inverter 173 is a "1". As a result, the output of NOR gate 175 remains at "0". The motor continues to rotate until a reflection from the mirror is again picked up by the light pipe 189. Now the output of the converter 177 goes from a logical "0" to a logical "1", and the output of inverter 173 to a logical "0". NOR gate 175 now has two "0" inputs resulting in a "1" output to reset flipflop 162. The result is a Q output of "0" from flipflop 162 which through the gate 163 and inverter 165 turns off the triac 167 stopping the motor 181.

The use of the dual flipflop arrangement insures that the flipflop 162 will not be reset until the motor has rotated sufficiently to get out of the range of the mirror and then returns into that area. Some of the motors in the system rotate at very low speeds and were this provision not made, an output resetting the flipflop 162 would occur before the motor even had a chance to turn.

Figure 7:
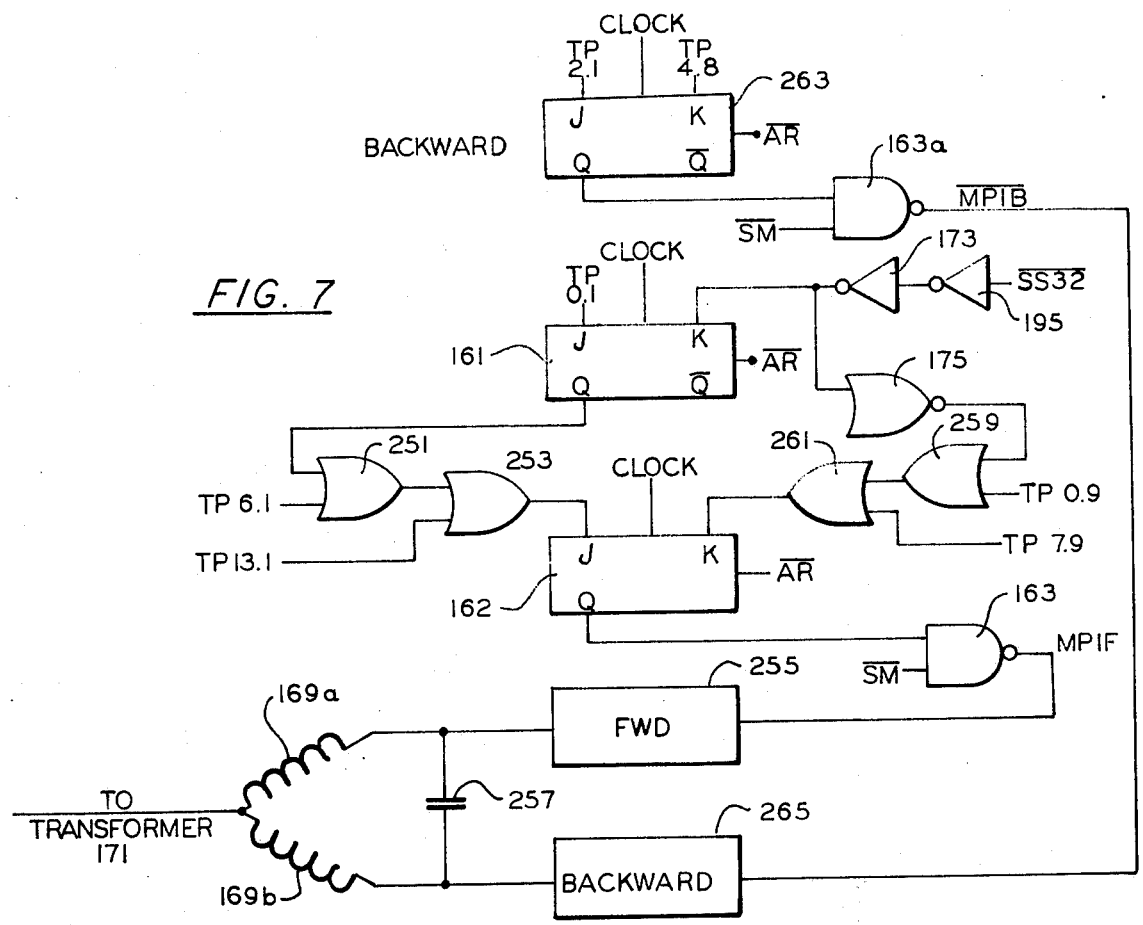
FIG. 7 is a diagram similar to FIG. 6 illustrating the manner in which a two-direction motor is driven.

As mentioned above, some motor drives are required to go in two directions. As example of such operation is the pipetter control. FIG. 7 illustrates the detailed logic circuitry associated therewith. In this figure, reference numerals in common to the reference numerals of FIG. 6 will be used where possible. In this cycle, it is desired to start a forward motion of the motor for the pipetter at the time of 0.1 second. Thus, a 0.1 second output from the decoder 153 of FIG. 6 is provided as the set or J input to flipflop 161. When a clock pulse appears, flipflop 161 is set. This results in a Q output of "1" which is one input to a OR gate 251. The second input to OR gate 251 is from the 6.1 second output of the decoder 153. Previously, both inputs were "0" and the output of gate 251 was a "0". Its output now goes to "1". This output is one input to a OR gate 253 which has as its other input the 13.1 second output of the decoder 153. This output will be "0". Thus, the output of gate 253 will go to a "1" and flipflop 162 will be set. In the manner described above, through a NAND gate 163, it will provide an input to a Triac motor control 255 such as that shown on FIG. 6. The motor in this case has instead of the one winding shown on FIG. 6, two windings designated 169a and 169 with a capacitor 257 between the windings. Winding 169a is arranged to cause forward rotation of the motor and winding 169b reverse rotation. As described above, the output of gate 163 will fire the Triac in Triac circuit 255 causing the motor to rotate in a forward direction. This will cause the pipette 31 of FIG. 1 to be lowered into the reagent. In the meantime, flipflop 161 has been reset through the Schmitt trigger 195 and inverter 173 in the manner described above in connection with FIG. 6. Thus, its Q output is a "0". At time 0.9 seconds sufficient lowering will have taken place and the motor is to be stopped. This is accomplished through the 0.9 input from the decoder 153 to an OR gate 259. This input will cause its output to become "1" causing the output of an OR gate 261 to have one "1" input and to provide a "1" input to the K or reset input of flipflop 162. The motor will stop and another motor associated with a different assembly will cause reagent to be drawn into the pipette using a vacuum pump to be described below. This will be accomplished by the time 2.1 seconds at which point, it is desired to move the pipetter backward. This backward movement is a movement which will cause the pipette to be raised and then rotated to a position over the cup in the magazine and lowered into the cup. To accomplish this, a further flipflop 263 is provided having as its set input the 2.1 second output of the decoder 153. Its Q output is provided to a NAND gate 163a operating in the same manner as gate 163 to initiate the firing of a second Triac circuit 265 to cause a flow of current through the reverse winding 109a of the motor. The motor turns in a reverse direction until the time 4.8 seconds when a corresponding output from the decoder 153 is used to reset the flipflop 263 causing the output of gate 163a to change and turn off the Triac circuit stopping the motor. Now, at time 6.1, an input from the decoder is provided into OR gate 251 causing its output to go from "0" to "1". Again with one "1" input, OR gate 253 will have a "1" output causing the flipflop 162 to be set to begin forward motion in the manner described above. This forward motion continues until the time 7.9 when an input to OR gate 261 results in an output therefrom resetting the flipflop. The pipette is now positioned at the wiper sponge where any remaining reagent is discharged. After discharge at time 13.1 seconds, forward motion is started again by the 13.1 output of the docoder 153 being provided as an input to OR gate 253. Rotation continues until the mirror 183 of FIG. 6 is encountered at which point, the changing output of Schmitt trigger 195 and inverter 173 through gates 175, 259 and 261 resets the flipflop 162 in the manner described above. Thus, throughout the cycle starting and stopping is controlled by the timer. However, the end of the cycle and the position at which the motor is stopped is controlled by an angular position sensor sensing the exact motor position. This ensures accurate repeatability from cycle to cycle. The cycle carried out in the preparation unit is given by the Table I below. Operation of the diluent and reagent pump drives and diluter probe drive is essentially the same as that described for the pipetter.

TABLE I

| PREPARATION UNIT TIMING | |
|---|---|
| Time (Real) | Action |
| 0.1 | Start Pipetter |
| 0.9 | 1) Stop Pipetter |
| | 2) Start Diluter Pump |
| 1.5 | Start Diluter Probe |
| 2.1 | Start Pipetter |
| 3.4 | Stop Diluter Pump |
| 4.0 | Stop Diluter Probe |
| 4.6 | Start Diluter Pump |
| 4.8 | Stop Pipetter |
| 6.1 | 1) Start Diluter Probe |
| | 2) Start Pipetter |
| | 3) Stop Diluter Pump |
| 7.9 | Stip Pipetter |
| 10.1 | 1) Start Diluter Probe |
| | 2) Check Mode |
| 10.9 | 1) Stop Diluter Probe |
| | 2) Start Table |
| 13.1 | Start Pipetter |
| 13.5 | Start Diluter Probe |
| 13.9 | Stop Diluter Pump |
| 15.4 | 1) Start Diluter Pump |
| | 2) Move, Go |
| 16.8 | End of Cycle |

Figure 8:
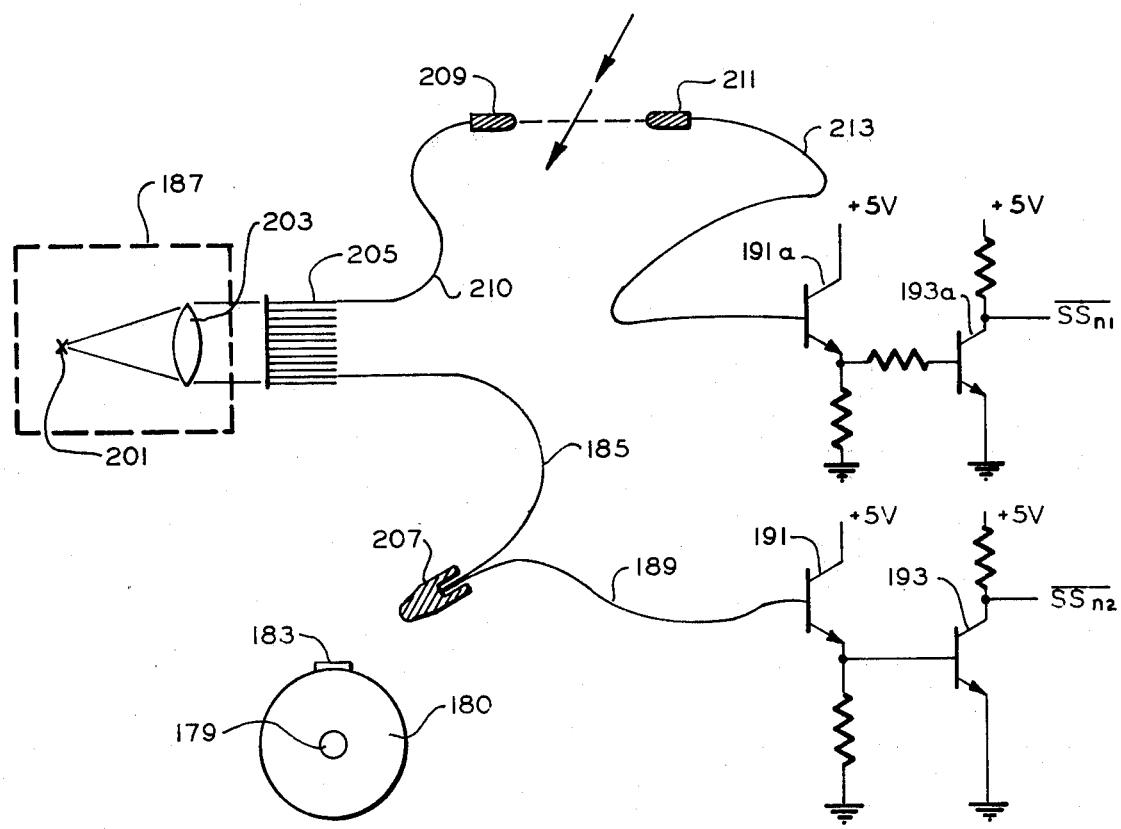
FIG. 8 is a circuit-optical diagram illustrating the optical sensing arrangement of the analyzer of FIG. 1.

The general opto-electric arrangement of the fiber optics in the system of the present invention is illustrated in more detail on FIG. 8. As shown, the optical sensor source 187 comprises a light source 201 and a lens 203 focusing the light source on a bundle 205 of optical fibers. In the present embodiment, thirty-eight light carrying fibers in all are used. For angle sensors such as described above in connection with FIG. 6, a fiber is brought to a lens unit 207 which acts both as a source and receiver. The lens unit is directed to a specific angular position on a disc or cam 180 associated with a motor shaft 179. As indicated above, a mirror 183 is mounted on the disc 180. A second fiber 189 is also inserted into the lens unit 207 to pick up light reflected from the mirror. Its other end, as indicated above is brought to a photo-transistor 191, the output of which is coupled to an amplifier transistor circuit 193.

Also illustrated on FIG. 8 is the arrangement for detecting magazine and cup position. At each of the detection positions, a source lens 209 having one of the fibers such as a fiber 210 from the bundle 205 as in input is positioned on one side and a receiving lens 211 on the other side. A fiber 213 is taken from the receiving lens to another photo-transistor 193a. As indicated by the drawing, if nothing is interposed between the source lens 209 and the receiver lens 211, an output will be provided from the transistor 193a. This output is indicated as $SS_{nl}$ or in other words, the condition of $SS_{nl}$ is not fulfilled, i.e., there is no magazine or cup in position. Once the light passage is blocked, the photo-transistor and the amplifier transistor will be turned off and the state of the output will change.

Figure 8A:
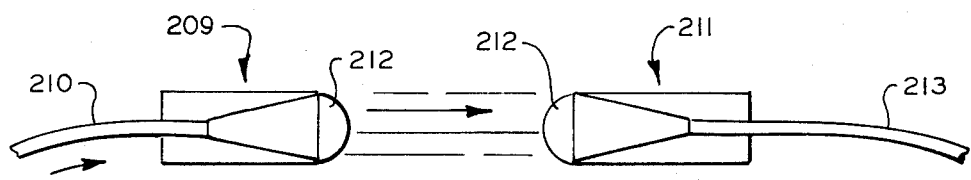
FIG. 8a shows a first type of optical object sensor.

FIG. 8a illustrates in more detail the construction of the source lenses 209 and receiving lenses 211. Each are one piece molded transparent plastic collimators cemented to the end of the fiber optics 210 and 213 respectively so that the end of the fiber is approximately at the focus of the spherical lens surface 212. Thus, the light entering from the fiber 210 ± diverges toward the lens surface ± 212 and on entering the area is approximately collimated. At the identical receiving terminal 211, the lens 212 acts in to opposite way to converge the light on the end of the fiber 213. As shown, the sources and receivers 209 and 211 respectively are mounted with their lenses 212 facing each other so that their axis of collimation are approximately colinear. They may be up to several centimeters apart with the maximum distance being limited by loss of light transmission caused by spreading of the partially collimated light to an area larger than the lens of the receiving terminal. The design is such that the focal ratio is similar to that accepted or illuminated by the optical fiber and its focal length is such that the optical fiber substends a field angle conveninently large so that the angular alignment of the optical axis of the two terminals need be no more precise than is conveniently attainable by a simple mechanical clamping of the outer surfaces of the source and receiver.

Figure 8B:
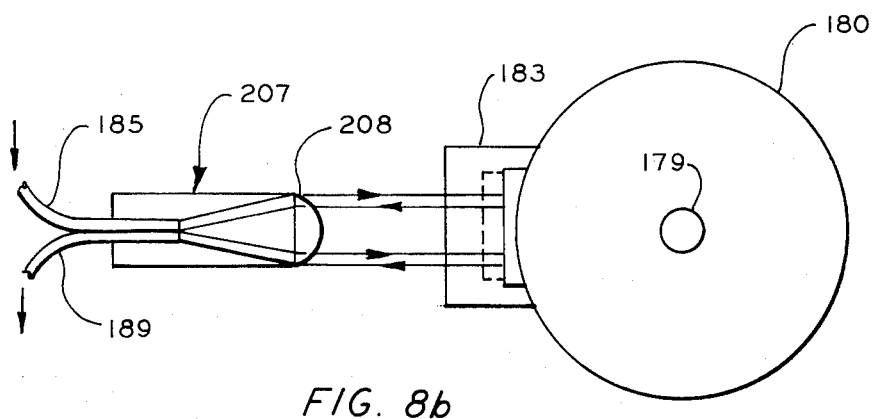
FIG. 8b is a plan view of an angular sensor.
Figure 8C:
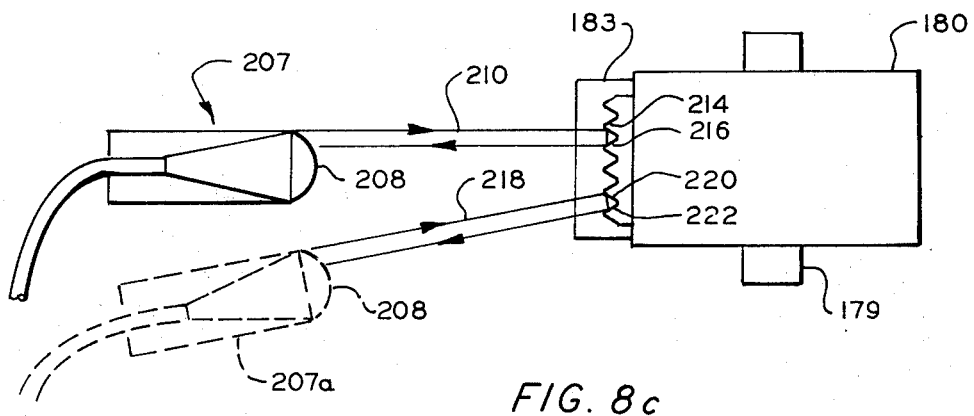
FIG. 8c is an elevation view of the angular sensor of FIG. 8b.

The angular sensing arrangement is shown in more detail on FIG. 8b and 8c. The lens unit or sensing terminal 207 consists of a small one piece molded transparent plastic auto-collimator with provision for receiving two fibers. The fibers 185 and 189 are cemented to it such that the end of each fiber is at a point conjugate with the other fiber end on opposite sides of the focus of the lens formed by the spherical surface 208. As shown on the plan view of 8b, the fibers 185 and 189 are arranged side by side and this manner oriented in the plane perpendicular to the axis of the shaft 179 of the rotating part to be sensed. As indicated above, the fiber 185 is the illuminating fiber and the fiber 189 the receiving fiber. The mirror 183 is preferably a retro-reflector. In the plan view of FIG. 8b, the mirror 183 is illustrated along with the light being directed from the lens unit 207 to the mirror and back to the lens unit. As with the units of FIG. 8a, the light is approximately collimated as it leaves the lens 208. The same lens then images the reflecting light on the end of the receiving fiber 189. Only when the mirror 183 is properly aligned with the axis of the lens unit 207 will a strong optical signal be transmitted which is then processed by the photodetector as described above. The use of a retro-reflector as a mirror 183 avoids the need to control the angle of mounting of the reflector on the rotating part in any other plane than the one perpendicular to the axis of rotation of the rotating part. That is to say, the mirror 183 is made as a retro-reflector in a plane parallel to the axis of rotation. This axis is the axis of the shaft 179.

FIG. 8c illustrates this principle. In a plane parallel to the plane of that shaft 179, the mirror 183 is a retro-reflector. Preferably, it is a molded transparent plastic part with a flat surface toward the lens unit 207 and on the side away therefrom contains an array of flat surfaces forming V-grooves acting as roof reflectors by total internal reflection. As shown, the roof edges are perpendicular to the axis of the shaft 179. The lens unit 207 is shown first in a perfectly oriented position. Light from the fiber is collimated as it leaves the lens 208 and the ray 210 illustrated strikes a surface 214 of the V-groove where it is reflected to the surface 216 and directly back to the lens 208 which then images it on the receiving fiber. However, because of the roof principle, even if the lens unit 207 is in the position of the lens unit 207a, operation will still take place in the desired manner. This is illusrated by the ray 218 which is reflected from the surface 220 thence to the surface 222 and back to the lens 208. Thus, minor maladjustments of the positioning of the lens unit 207 or reflector in the plane parallel to the axis of rotation causes no effect while the sensitivity to angle in the plane perpendicular to the axis is essentially undiminished.

As with the sensors of FIG. 8a, the optical design is such that the focal point of the auto-collimator is similar to that illuminated or accepted by the optical fibers but the focal length is chosen so that the diameter of the end of the optical fiber subtends a field angle in air about half the angle within which it is desired to sense the rotation of the rotating part.

The angular sensing system can be made unusually sensitive to angular rotation by making its field angle relatively small. Where it is desired to use the same diameter of optical fiber for the sensing arrangement of FIG. 8a and that of FIGS. 8a and 8c, this can be achieved by making the focal length of the lens unit 207 relatively long. Because the reflected beams angle changes at double the rate of rotation of the reflector and because the physical length of the auto-collimator is shorter than its focal lens in air by the ratio of the refractive index of the transparent material to the refractive index of air, the sensing system illustrated of FIG. 8b and 8c can detect rotation to better than $\pm$ 1° sensitivity to an apparatus no longer than three centimeters using a 1 millimeter diameter fiber. It is particularly important that the rotating part does not need to have any large radius to achieve this sensitivity. The radius at which the reflector is mounted is of no importance and the distance from the auto-collimator lens unit 207 to the reflector 183 is not critical as long as too much vignetting does not occur. Because of the high directionality of the lens units, on the sensing optical fibers, diffuse illumination from the environment is seldom a practical problem in the embodiment described since sufficient light does not enter the sensing terminals at precisely the right angles.

Figure 9:
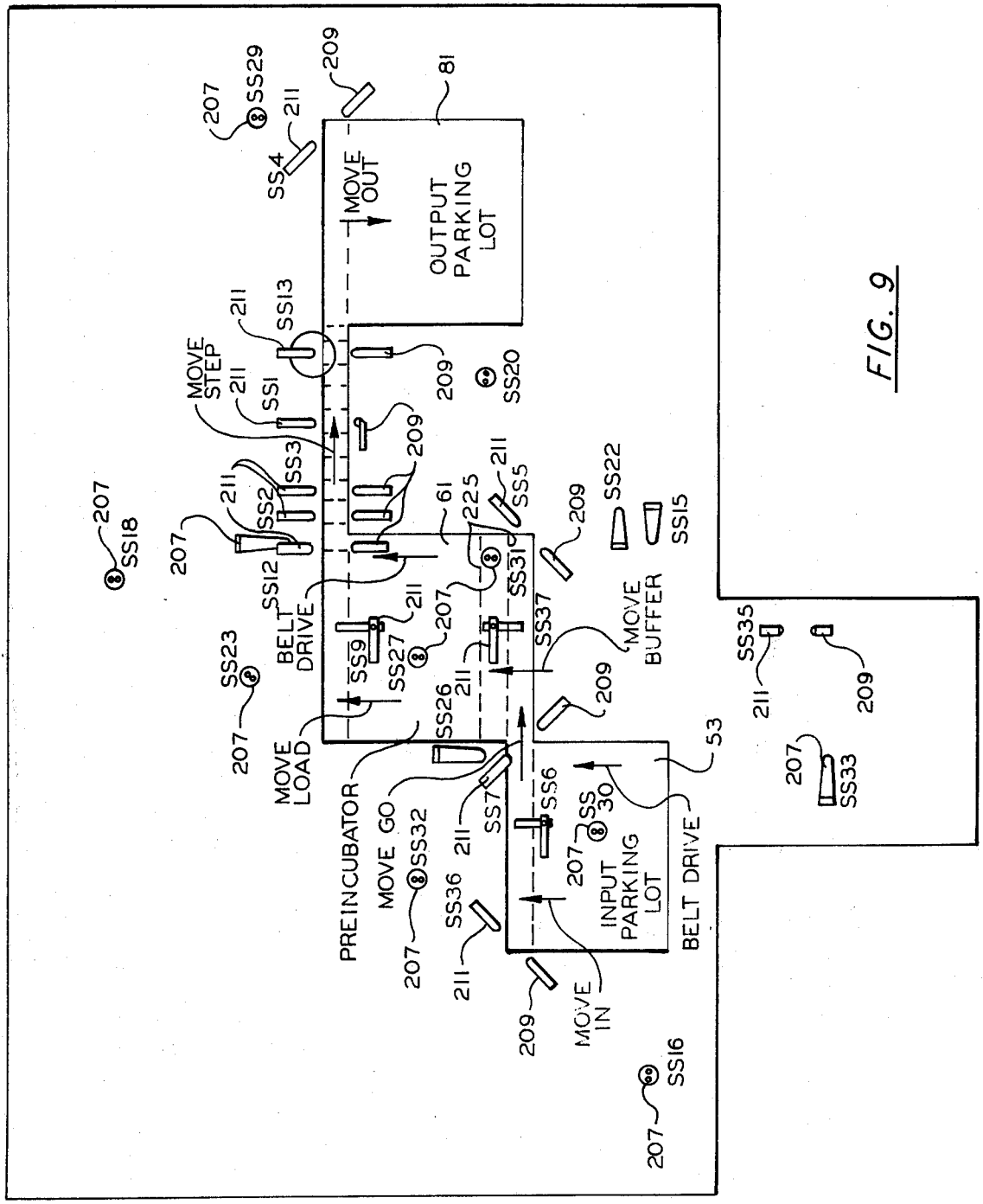
FIG. 9 is a plan view illustrating the location of optical sensors in the analyzer of FIG. 1.

FIG. 9 is a schematic plan view of the movement of the magazines through the apparatus. The specific mechanical means for obtaining such movement will be described in more detail below. The purpose of FIG. 9 is to illustrate sensor locations and to give an indication of their purpose. Within the area 53 referred to as the input parking lot, three sensors are provided. These are the sensors designated SS6, SS36 and SS7. The sensors SS7 and SS36 are shown including lens sources 209 and lens receivers 211 such as shown on FIG. 8 above. For sensor SS6, only the lens receiver is shown with the lens source being located vertically above the sensor. Sensor SS6 indicates that a magazine has been moved by the belt into a position where serum, diluent, and the first reagent are to be located into a cup. Mechanical stop means are provided as will be seen below to hold the magazine in this position until it can be loaded. Sensor SS36 is used to sense the presence of a magazine in position and sensor SS7 to sense the presence of a cup in the position designated by cup 55a on FIG. 1, i.e., the position for filling. Clearly, before a new magazine can be loaded in the preparation position, neither sensor SS36 nor sensor SS7 can be indicating the presence of a magazine or cup. Essentially, these magazines are constructed so that an indication of the presence of a magazine but the absence of a cup will be sensed. This is an improper condition and in response thereto, the magazine transport is stopped until further action is taken by the operator. These sensors are also used in a manner which will be described below to stop preparation where a spacer magazine is inserted to indicate a change of tests.

Once the magazine has been stepped through all its cup positions, it will encounter the sensor arrangement SS5. Again, sensor arrangement SS5 includes a source lens 209 and receiver lens 211. This indicates that the magazine is ready to be moved into the pre-incubator area 61. Before such movement is carried out, however, there must be an available space, i.e., the space indicated between dotted lines 225. Thus, another sensor lens receiver 211 with a source not shown thereabove is provided in order to insure that space is clear. Thus, if this space is clear and a magazine is behind it, this combination of signals is used to operate the mechanism to move the magazine into place. The magazine is then driven by the belt drive until it reaches the position of sensor SS9. Again, only the lens receiver 211 is indicated, the source lens being thereabove. If a magazine is in the position ahead, this will be indicated by the sensor SS12. This sensor indicates the presence of a magazine in that position and that a new magazine cannot be loaded. Once that area is free, the sensor SS12 output changes and the means to move the magazine into position will be operated. Next in line is a sensor SS2 again comprising receiver 211 and source 209. This senses the presence of a cup. Its output is used to enable the second pipetter and the stirrer to add the second reagent and stir the reagents, diluents and serum. This sensor in conjunction with sensor SS12 is also used with the spacer magazine to stop operation of the analyzer section. Again, if the presence of a magazine is indicated by sensor SS12 but the absence of a cup is indicated by SS2 within a cycle then the analzyer cycle is stopped until the operator takes further action. Next, sensor SS3 senses that the cup is in position for transfer of the sample to the photometer. This is a transfer of position associated with the tests other than CPK, i.e., those having a short incubation period. When one of these other tests is selected and the sensor SS3 senses the presence of a cup in that position, the transfer cycle is initiated to transfer the sample and reagents mixture to the photometer. Similarly, the sensor SS1 is used in conjunction with the CPK test to initiate transfer when that test is selected. Sensor SS13 is a magazine sensor used to indicate that there is still a magazine in the analyzer section. If there is no magazine therein, nor a magazine sensed at the position SS12, then operation of the analyzer may cease. The final sensor shown SS4, senses that the magazine has moved all the way over and is aligned with the output parking lot 81. When a magazine is sensed thereby, means are actuated to move it into the output parking lot 81. Also shown on FIG. 8 are the locations of all the motor shaft angular sensors. Table II below lists all sensors.

TABLE II

| Sensor Number | Function |
|---|---|
| 1 | 120 SEC (CUP POSITION) |
| 2 | R2 (CUP POSITION) |
| 3 | 24 SEC. (CUP POSITION) |
| 4 | MOVE OUT (MAGAZINE POSITION) |
| 5 | MOVE BUFFER (MAGAZINE POSITION) |
| 6 | MOVE IN (MAGAZINE POSITION) |
| 7 | PREP UNIT (CUP POSITION) |
| 9 | MOVE LOAD (MAGAZINE POSITION) |
| 12 | ANALYZER (MAGAZINE FIRST POSITION) |
| 13 | ANALYZER (MAGAZINE LAST POSITION) |
| 15 | DILUTER PROBE |
| 16 | DILUTER PUMP |
| 18 | TRANSFER PUMP |
| 20 | PIPETTE R2 |
| 22 | REAGENT PUMP R2 |
| 23 | STIRRER |
| 26 | MOVE GO (MAGAZINE DRIVE) |

TABLE II-continued

| Sensor Number | Function |
|---|---|
| 27 | MOVE LOAD (MAGAZINE DRIVE) |
| 28 | MOVE STEP (MAGAZINE DRIVE) |
| 29 | MOVE OUT (MAGAZINE DRIVE) |
| 30 | MOVE IN (MAGAZINE DRIVE) |
| 31 | MOVE BUFFER (MAGAZINE DRIVE) |
| 32 | PEPETTE R1 |
| 33 | SAMPLE TABLE DRIVE |
| 34 | SOURCE CONTROL |
| 35 | LAST SAMPLE INDICATOR (TABLE) |
| 36 | PREP UNIT LOADED (MAGAZINE POSITION) |
| 37 | PREINCUBATOR LOADED (MAGAZINE POSITION) |

After transfer to the analyzer section, the reagent is added to the second cup and stirring carried out under the same type of control as described in connection with FIGs. 6 and 7. When a cup gets to the position of the sensor SS3 or SS1, depending on the test being conducted, the transfer cycle is initiated and carried out by motors driven essentially in the manner described above. A motor is used for driving the pump with various motions taking place at assigned times under control of the timer. Oscillating motion is provided by a hydraulic system driven by the same motor. The exact operation of the mechanical arrangement and the transfer pump will be explained below. At this junction, suffice it to say that the mechanism is effective to transfer a sample of the reagents mixed with the serum sample and diluent to the photometer cell 71 shown on FIG. 2. The sequence of events in the analyzer unit is given in Table II below.

TABLE III
TIMING OF THE ANALYZER UNIT

| Time (Sec) | Function |
|---|---|
| 0.0 | Start of Cycle |
| 0.1 | Start of Transfer Pump |
| 2.1 | 1) Reset Output Registers |
| | 2) Reset Calculator |
| | 3) Move Load |
| | 4) Move Out |
| 5.8 | Start Pipetter |
| 6.6 | 1) Start Reagent Pump |
| | 2) Start Mirror Selection |
| | 3) Stop Pipetter |
| 7.8 | Start Pipetter |
| 9.5 | 1) Open Photometer Shutter |
| | 2) Stop Mirror Selection |
| 10.3 | 1) Stop Transfer Pump |
| 10.5 | Stop Pipetter |
| 11.7 | 1) Auto Zero |
| | 2) Start Stirrer |
| 11.8 | 1) Start Pipetter |
| | 2) Stop Reagent Pump |
| | 3) Start Transfer Probe Position Selecting |
| 12.7 | 1) Start Reagent Pump |
| | 2) Start Measuring 1st Quarter |
| 13.6 | Stop Pipetter |
| 14.5 | 1) Start Pipetter |
| | 2) Stop Transfer Probe Position Selection |
| 14.9 | 1) Start Measuring 2nd Quarter |
| | 2) Stop Stirrer |
| 17.1 | Start Measuring 3rd Quarter |
| 19.3 | Start Measuring 4th Quarter |
| 21.5 | Stop Measuring |
| 21.6 | 1) Do Curvature Check |
| | 2) Transfer Result to Output Registers |
| | 3) Reset TTY-Interface |
| 21.8 | 1) Start Stirrer |
| | 2) Indicate Red Print |
| | 3) Set Sequence No. |
| 22.1 | 1) Print Result |
| | 2) Start Transfer Pump |
| | 3) Close Photometer Shutter |
| 23.1 | 1) Transfer Result to TTY |
| | 2) Paper Feed 1 |
| 23.3 | 1) Paper Feed 2 |
| | 2) Move Step |
| 23.9 | Check for Spacer Magazine |
| 24.0 | End of Cycle |

PRIMARY CONTROLS

Figure 10:
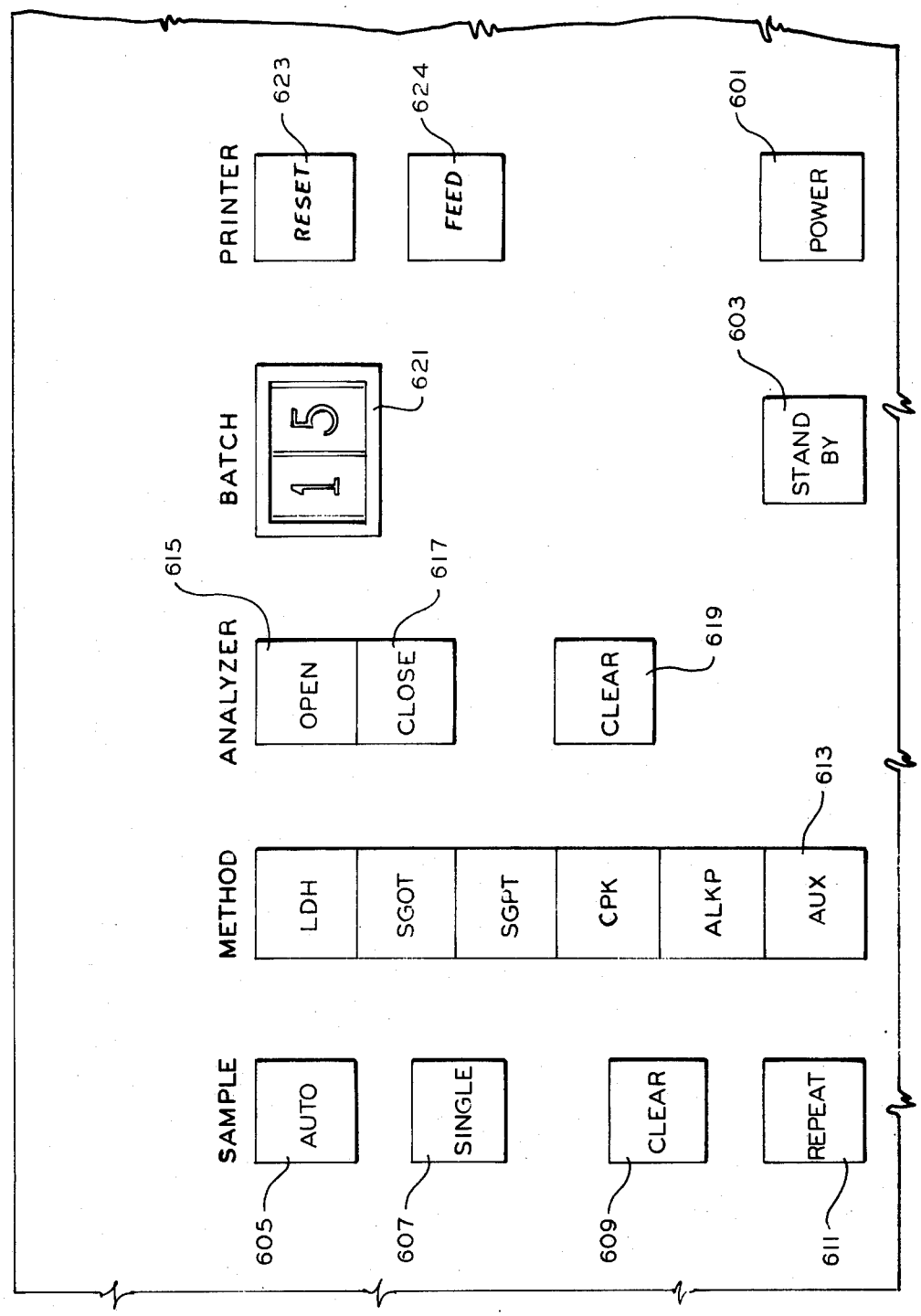
FIG. 10 is a front view of the control panel of the analyzer of FIG. 1.

FIG. 10 is a front view of the main control panel. It includes a power switch 601 used for turning on the machine. Power switch 601 will turn on all the necessary power supplies and start up the clock in conventional fashion. As with all switches, this is a combined switch-indicator and lights when operated. Next to the power switch is a standby switch 603. Standby switch 603 is used to disable all motors in the machine to avoid excess wear if the machine is not being used but still must be maintained in a condition where it can be started at any time without warmup.

As noted above, the machine is logically two separate machines, i.e., a preparation unit and an analyzer unit. Below a heading labeled "sample" are a plurality of switches. The first of these, switch 605, is the auto switch, which, when activated, puts the preparation unit into an automatic mode where it will continually add samples, diluent and reagent to the magazines. Pressing the single button 607 will result in only a single cycle of serum sample, diluent and reagent addition. A clear switch 609 is provided so that a magazine can be cleared out of the preparation unit and advanced to the analyzer unit. Pressing this button causes the mechanism which steps the magazine through its cup position to advance it out of the preparation unit and into the preincubation area where it will be transported to the analyzer unit. Finally, there is a switch 611 labeled "repeat" which is pressed if a test is to be repeated. The next column of switches are labeled "method" and permit selection of one of the tests, described above. These tests are LDH, SGOT, CPK and ALKP. These switches cause the required parameters to be set into three various parts of the unit. Finally, a switch 613 labeled "AUX" is provided for selecting a test which can be set in on the auxiliary control panel to be described below.

The next group of switches deal with the analyzer. These include a switch 615 labeled "Open" and a switch 617 labeled "close", along with a switch 619 labeled "Clear." The "open" switch opens the analyzer or enables it to carry out its function. The "close" switch closes the analyzer section so that no more magazines can enter into it. Closing of the analyzer unit will be described in more detail below. The clear switch 619 performs a similar function to the clear switch 609 in the preparation unit. It is used to move magazines in the analyzer area over to the output parking lot. A digital switch 621 is provided and labeled "Batch." This permits setting in a batch number which will then be printed out on the printer for all samples. Finally, there are two printer controls 623 and 624 labeled "Reset" and "Feed." The switch labeled "reset" is used to reset to zero a sample sequence number. The switch labeled "feed" is used to advance the paper feed in the printer 77.

Figure 11:
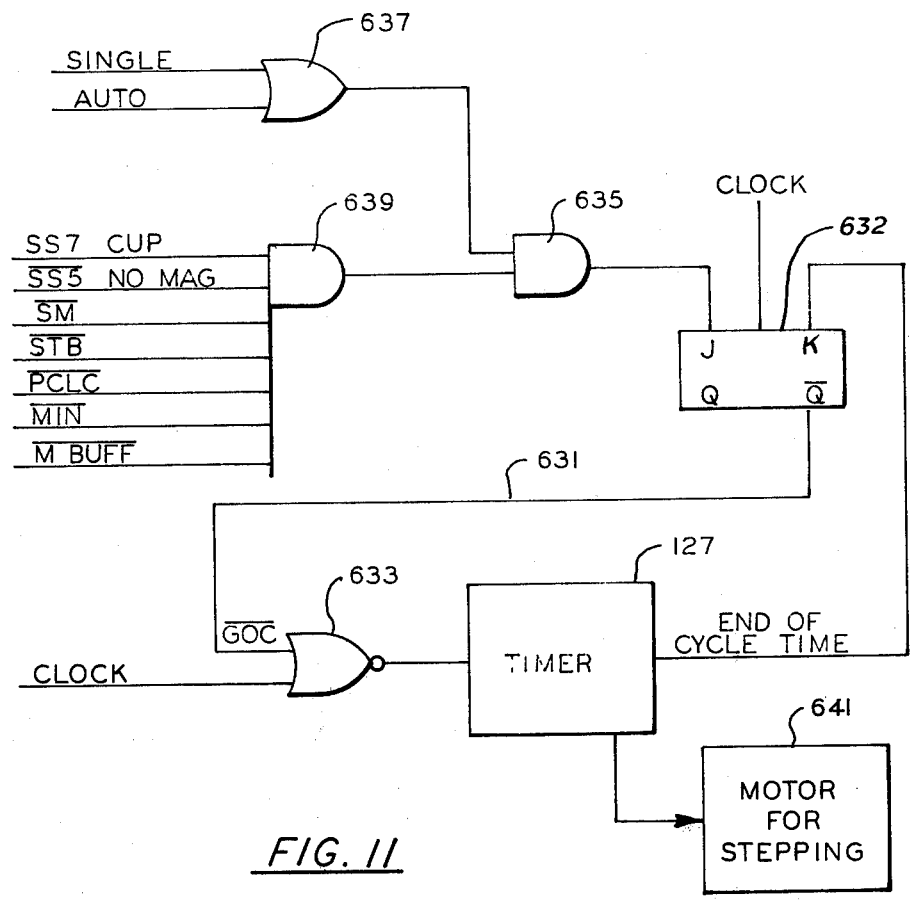
FIG. 11 is a logic diagram illustrating the logic used in starting a preparation cycle.

FIG. 11 is a simplified illustration of the control of the preparation unit. The timer 127 of the preparation unit is not started unless a signal on line 631 labeled "GOC" representing a go cycle is present. This signal enables gate 633 to permit clock pulses into the timer. The signal on line 631 is the output of clocked flipflop 632 (note that in this figure, and in other figures for the sake of simplicity AND and OR gates are used as examples). In practice, most logic functions will be implemented using NAND amd NOR logic as is the more conventional practice. It will be evident to those skilled in the art how the necessary AND and OR functions can be obtained using NAND and NOR logic. Flipflop 632 has as its J input the output of AND gate 635. Gate 635 has as its first input the output of an OR gate 637 which has as its two inputs the single and auto outputs of the switches of the control panel shown on FIG. 10. Thus, once the machine is operating the operator may then select a single or auto cycle whereupon a signal will appear at one input of the AND gate 635. However, before starting a cycle in the preparation unit, a number of conditions must be checked. To check that all the proper conditions are fulfilled, an AND gate 639 is used. Reference to FIG. 9 in conjunction with FIG. 11 is helpful in understanding the meaning of the various conditions. The first condition is the presence of a cup as sensed by the sensor SS7 of FIG. 9. Unless there is a cup in place, there is no reason to carry out the cycle. The second check is to make sure that there is no magazine at the position sensed by the sensor SS5. Since the last step of the timer cycle is the movement of the magazine toward the preincubator area, the carrying out of this cycle with a magazine present at the position sensed by the sensor SS5 will cause trouble. Thus, the cycle is not carried out until the area into which the magazine is to move during the cycle is clear. The next condition is that a stop mode has not occurred. Stop mode is a condition initiated by failure of the lamp in the optical sensor system, as described above, or when the machine is being serviced and a switch has been thrown by the serviceman. The next check is that standby has not been selected. If the apparatus is in the standby mode, the operator does not desire to carry out processing. The next is to see if the clear mode has been selected. This is necessary since during the clear mode the conditions will be met, that the cups will be in position and no magazine will be in position. Next, a check is made to make sure that a magazine is not being moved into the preparation area. The necessary indication from sensor SS7 would be present during the move-in cycle and it is desired that this cycle be completed before the timer cycle starts. Finally, a check is made to insure that the magazine is not being moved into the buffer or preincubator area 61 of FIG. 9. This essentially is an extension of the sensor SS5 output. In other words, if a buffer magazine movement is in process, the magazine may still be in a blocking position even though the sensor output of SS5 indicates no magazine in that position. If all these conditions are met, then a preparation cycle can be carried out and an appropriate signal from gate 639 enabling gate 635 is provided. As long as "single" or "auto" has been selected, on the next clock cycle flipflops 632 will be set and a signal on line 631 indicating a go cycle will be present enabling gate 633 to pass clock pulses to the timer 127. At the end of the timer cycle, an appropriate output to the K input of flipflop 632 is provided to cause it to be reset.

The manner in which the magazine is moved, before, during and after a preparation cycle will now be described. As alluded to above, movement of the magazine once it is in the preparation position, i.e., an advance of one cup after each cycle, is carried out in response to an output from timer 127. Thus, there is shown an output from the timer to a motor for stepping designated 641. Operation of this motor is essentially as described above in connection with FIG. 6. That is, in response to an appropriate output from the timer its control circuitry will start the motor and the motor will rotate until an optical sensor senses the mirror on the motor shaft or cam. The advancing mechanism is a modified geneva mechanism with projections engaging the bottom of the magazine. Three projections on a disk are provided so that for each advance of one cup, one-third revolution of the motor is required. Thus, this motor contains three separate mirrors on its shaft and advances one-third revolution in response to each timer output. Movement of the magazine into the preparation unit is controlled by logic illustrated on FIG. 12. Shown is the move-in motor which operates a mechanical means also to be described below which pushes the magazine from the input parking lot 53 into the preparation position. This motor is shown as a block 643 representing the motor itself and the associated logic controls such as those described in connection with FIG. 6. The motor drive rather than responding to a timer output responds to a set of conditions which must be present at the input to an AND gate 645. These conditions include no magazine in position as sensed by the sensor SS36 of FIG. 9; no cup as sensed by the sensor SS7 of FIG. 9; no go cycle indicating a preparation cycle in process (i.e., a go cycle could be in progress in which a magazine was moving into the position where it would be sensed by sensor SS5 — it could be out of the range of sensor SS7 but still be in the way of a magazine moving in); a magazine ready as sensed by sensor SS6; and no stop mode. With all these conditions met, the space is free and the magazine can be moved in.

Movement of the magazine into the preincubator area 61 is carried out in similar fashion. Thus, if no magazine is in the position SS37, which indicates a backed up condition and the fact that no further magazines could be loaded into the preincubator, and if a magazine is sensed at the sensor SS5 and the other conditions such as no stop mode are present, the magazine is moved into the preincubator area. Similar logic initiated by time signals is used for moving the magazine into the analyzer area stepping it through the analyzer area and moving it to the output parking lot 81.

Figure 46:
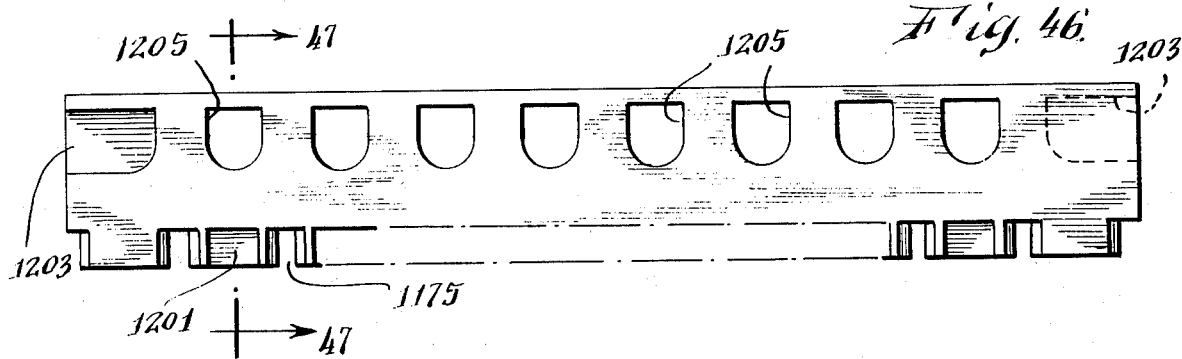
FIG. 46 is an elevation view of the magazine shown in FIG. 45.
Figure 47:
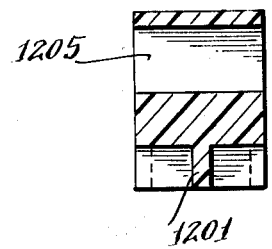
FIG. 47 is a sectional view through the spacer magazine of FIGS. 45 and 46.

At this point, it might be well to describe the manner in which spacer magazines are used to stop the cycle in order to notify the operator that reagents must be changed. The spacer magazine (shown on FIG. 46) is formed so that it has a cutout at its end and so that it has a clear path through each cup. The cutout at its end results in no change in output from the sensor SS7 after the magazine is moved into position. As a result, gate 639 of FIG. 11 will not be enabled and a timer cycle will not be started. The output of sensor SS7 along with the sensor SS36 can be used to give an indication of this condition, i.e., a condition where a magazine is in position but no cup is present.

Operation in the analyzer unit is somewhat different. Note that in the analyzer, two magazines may be in position for processing and when a spacer magazine moves in to the point where it is sensed by the sensor SS12, another magazine may be in front of it being processed. The timer in the analyzer unit runs continuously and the carrying out of its various sequence of operations is initiated strictly by the sensing of cups at the sensors SS2, SS3 and SS1. Once a magazine is in position and sensed by the sensor SS12, it will automatically be moved one step ahead. At this point, the sensor SS2 looks to see if there is a cup. If no cup is present but if there is a magazine sensed at the sensor SS12 at a specific time, a command is generated to close the gate. This is the closed indication which will be displayed on a light switch 617 of FIG. 10. This signal disables the drive used to move subsequent magazines into the analyzer position. Thus, all further magazines will be stopped at the sensor SS9 and will not move into the analyzer unit until this condition is cleared by pressing the open button 615 of FIG. 10. The analyzer timer cycle continues to run and to step the magazine through the analyzer unit. However, the fact that no cups are present will be sensed at the sensors SS2, SS1 and SS3 and signals enabling the motors driving the second pipetter, the stirrer and the transfer pump will not occur. Thus, the spacer magazine will be stepped through without any action being taken by the analyzer unit other than the stepping itself.

PHOTOMETER

Figure 12:
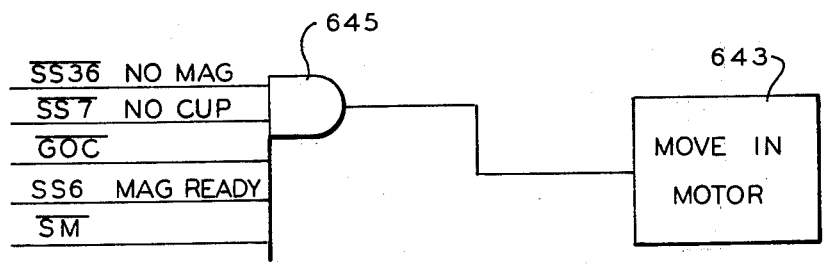
FIG. 12 is a logic diagram illustrating the logical conditions required for a typical motor operation.
Figure 13:
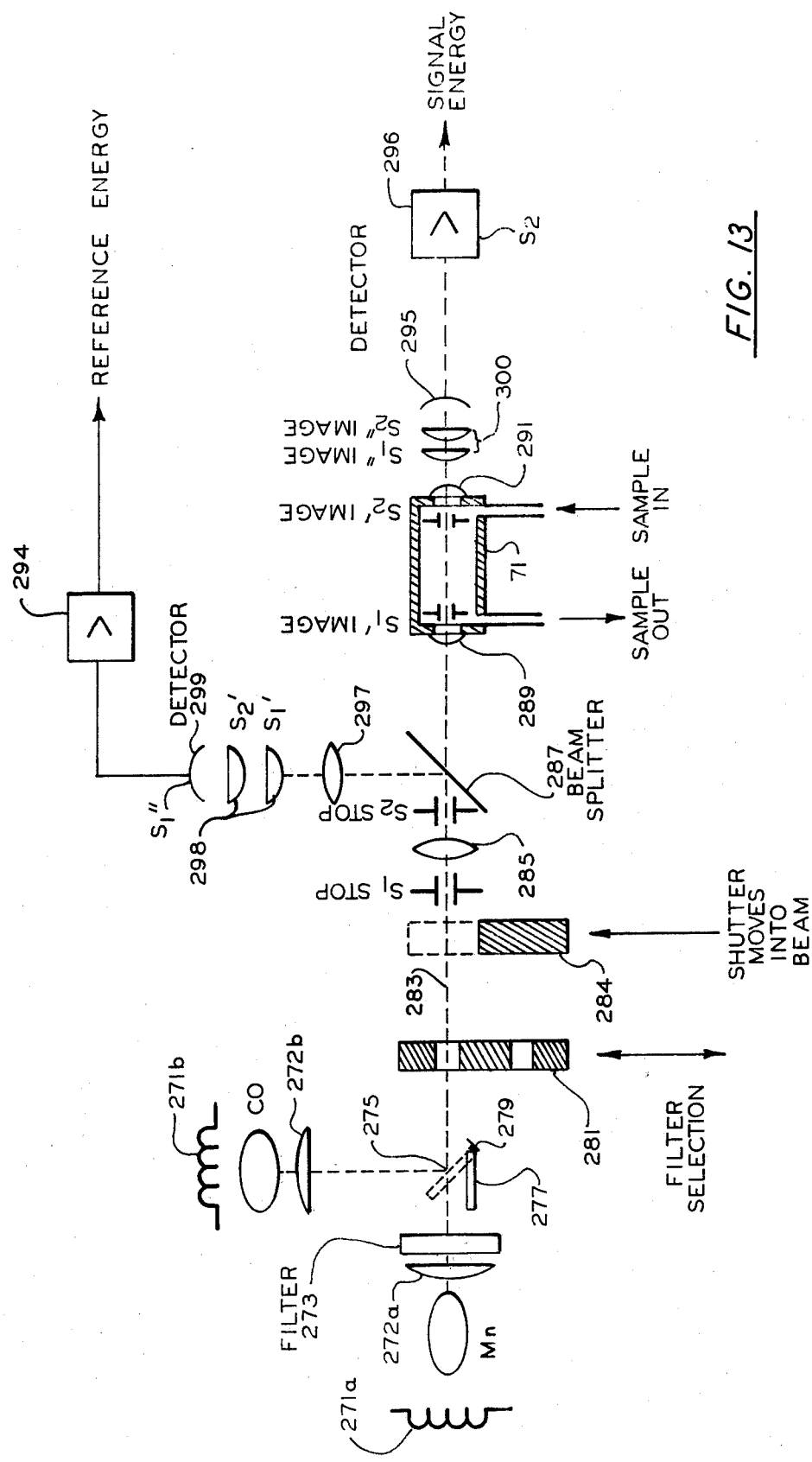
FIG. 13 is an optical schematic partially in section illustrating the photometer of the analyzer of FIG. 1.

The curvet, also referred to as the cell, along with the optical elements of the photometer are shown on FIG. 13 which is an optical/mechanical schematic. The photometer of the present invention provides improved sensitivity and stability through a number of means. The system starts out with a light source emitting light of predetermined wavelengths. In the embodiment of FIG. 13, two hollow cathode lamps are provided: a maganese lamp 271a emitting light at about 404 nm and a cobalt lamp 271b emitting light at about 340 nm. Since the wavelengths emitted are those of the atoms of the lamps' cathodes, these wavelengths are extremely stable and repeatable, contributing to the stability of the photometer. Lenses 272a and 272b are provided respectively in front of the lamps 271a and 271b to form a beam of light. A 404 nm filter 273 is installed in front of the lens 272a. The two light paths intersect at a point 275. At this point, a mirror 277 rotatable about an axis 279 is installed. Which of the lamps is used is determined by the test being run. The various parameters associated with the different tests are detailed in Table IV of FIG. 12a. Depending on the selection, an output from the parameter memory or auxiliary setting panel will cause the mirror to be rotated to the position in solid lines for light at 404 nm or to the position shown on dotted lines for light at 340 nm. In conjunction therewith, a movable filter 281 is positioned to pass only a band containing the selected wavelength. The selected wavelength of light then travels along the optical axis 283 toward the cell 71.

The next important step followed in the photometer apparatus of the present invention is that of defining the etendu of the beam. This is essential in order that a beam of known and uncontrolled throughput of light flux is provided, and so that it is possible to split the beam into a signal path and a reference path, each of which will also have known and controlled throughputs of light flux. It is essential in so defining the etendu and in generating the beam that the light source have an area of essentially uniform brightness, and that the image of this area of uniform brightness overfills the first stop upon which it is imaged. The etendu is defined through the use of a field stop S1 and an aperture stop S2 with a lens 285 therebetween. The light beam prior to encountering the stops S1 and S2 passes a shutter 284. The shutter is normally maintained closed and is opened only for a predetermined period during which the measurement is made for reasons described below. The shutter is controlled by an appropriate timer output. The beam having a defined etendu is then directed to a beam-splitter 287 of the coated type which preserves uniformity of illumination in both light paths. The beam-splitter 287 is coated so as to transmit approximately 90% of the beam and reflect the remaining 10% of the beam. Thus, the two beams formed thereby will be of lower intensity than the original beam, but will both be of uniform illumination across their respective cross-sections. The transmitted portion of the beam, i.e., the portion containing 90% of the energy, enters the cell 71 first passing through a lens 289. The lens 285 images the field stop S1 near the entrance to the cell with the lens 289 imaging the stop S2 near the exit of the cell. These lens means are shown only as examples and it will be recognized by those skilled in the art that any equivalent lens arrangement which will so image the stops may be used. The purpose of this imaging is to ensure that the light path is kept away from the sides of the cell, and further that the boundaries of the beam are well defined, so that small mechanical motions of the parts may occur without the beam's hitting either the walls of the cell or the margins of any of the optical parts. This makes the throughput of light flux in the beam stable with respect to small mechanical or optical disturbances. A further lens 291 is provided at the exit end of the cell 71. This lens images the stop S1 at a condenser lens arrangement 300. The condenser lenses shown as two lenses image the stop S2 on a detector 295. It is essential that these lenses are able to encompass as large an input angle as possible so that they can collect as much scattered light as possible. Although the beam is well defined travelling through the cell 71 the liquid therein may scatter the beam to some degree and the improved results obtained with the photometer system are at least partially due to this ability to collect nearly all such scattered light. Furthermore, it is essential that the lenses 300 image the light well within the boundaries of the active area of the detector 295 so that all of the output from the cell is measured in spite of small mechanical motions of the optical parts which may cause the beam to move. Light in reflective path from beamsplitter 287 is directed through a lens 297 and a pair of condenser lenses 298. Lens 297 images the field stop S1 on the first lens and the stop S2 on the second lens. The second lens images the image S1 time on the detector on a second detector 299. Again, it is essential that all of the beam be imaged within the sensitive area of the detector 299.

As will become more evident below, the output of the detector 299, which is a reference detector, is used to cancel out of the output of the detector 295, which is the signal detector, any output variations resulting from variations at the illumination sources 271a and 271b. Any variations occurring before the splitting of the beam 283 will thus be cancelled out. The signals from the detectors as illustrated are amplified in respective amplifiers 296 and 294 and then processed in a manner to be described below. The shutter 284 is kept closed except during a measurement cycle, that is, when samples are being transferred, the shutter remains closed. This prevents any inaccuracies due to a response time effect of the detectors 295 and 299, the proper light levels being applied to these detectors at the same time. Were the shutter left open, the light would always be on the reference detector 299 whereas, the detector 295 could have a lag in responding to a sample transferred to the cell. Under such circumstances, errors could result, because of the difference in the history of illumination on the two detectors.

In spite of all precaution, small mechanical and optical disturbances will occur, some of which may cause the images to move or change size on the detector's sensitive areas. Therefore, it is advantageous that the detectors have uniform response to light over their active area.

Further, since the response of detectors to light is dependent upon their temperature, it is important that the two detectors be at the same temperature and that this temperature not change during the measurement.

If these teachings are faithfully carried out, then the only phenomena that will significantly affect the ratio of the signals detected in the two beams is a change in absorbance of the sample.

Figure 14:
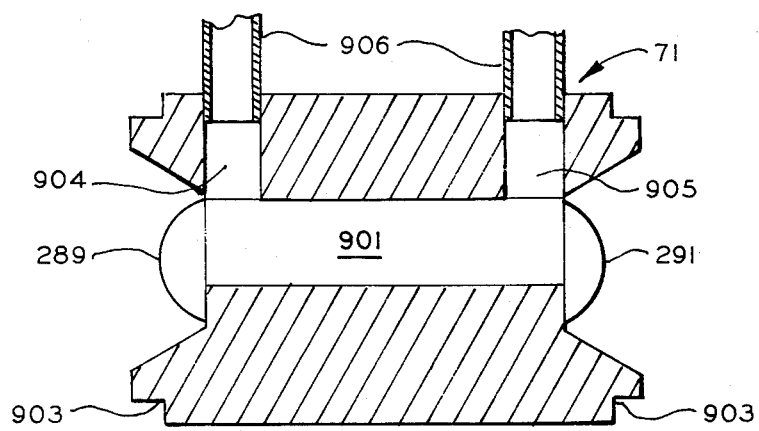
FIG. 14 is a longitudinal section through the photometer cell of the photometer of FIG. 13.

A more detailed drawing of the photometer cell 71 is shown on FIG. 14. The cell itself is made of silver, because of its high thermal conductivity, and contains a chamber 901 in which the sample rests during measurement. The exterior of cell 71 is essentially cylindrical; cutouts 903 at each end of the cell are provided for resting the cell in a plastic block as described presently. Ports 904 and 905 at the respective ends of the cell enable transfer of the sample into and out of chamber 901. Inserted into each of the ports 904 and 905 is a stainless steel nipple 906.

While it is essential that the sample be maintained at a particular temperature during measurement, it is more important that the temperature not change at all during measurement. Specifically, it is sufficient if the temperature of the sample in the cell is within 0.2° C of the desired temperature 30° C; however, the temperature during the measuring period should not vary more than 0.01° C. In the buffer or preincubation area 61 shown on FIG. 1, resistance heating is provided to bring the samples to approximately the desired temperature.

Figure 15:
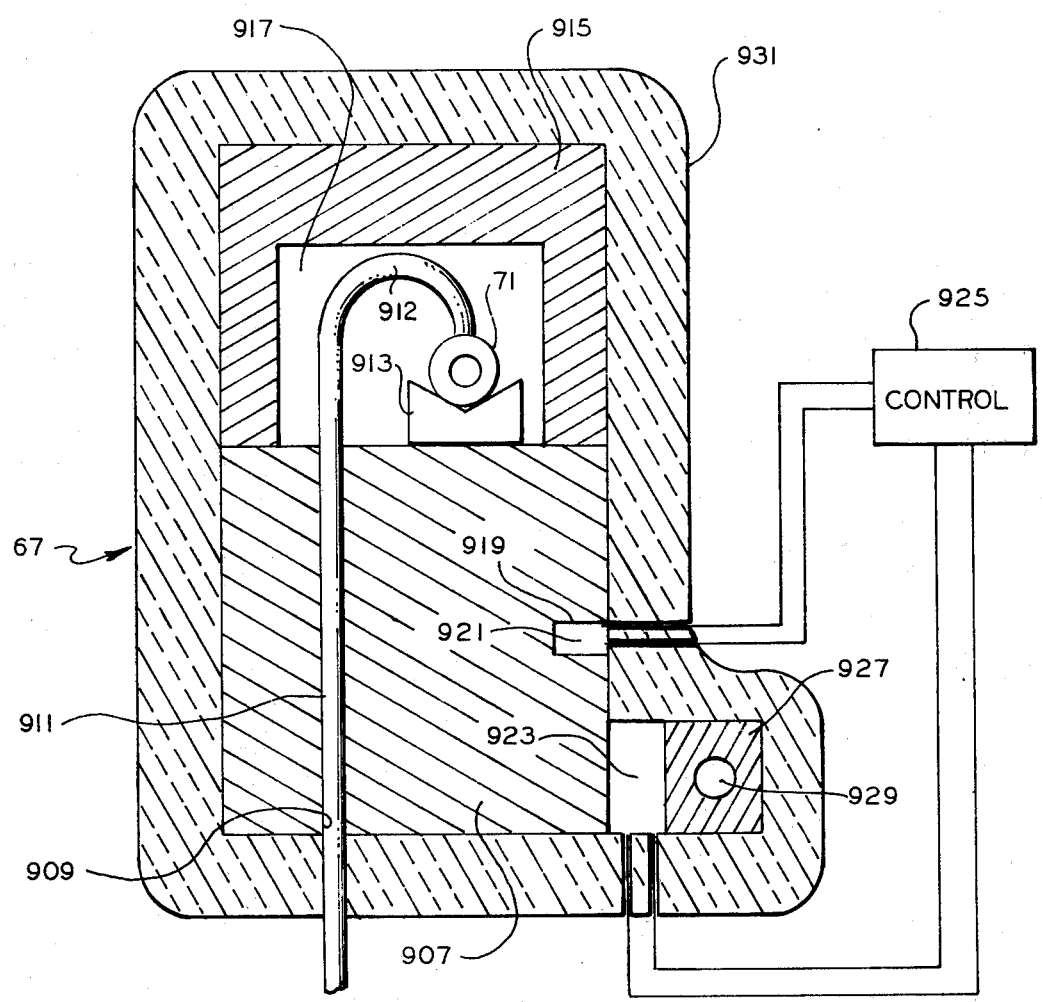
FIG. 15 is a cross sectional view illustrating the temperature control system for the photometer of FIG. 13.

As indicated in connection with FIG. 2, the samples are then brought to the desired measurement temperature while passing through a thermostated aluminum block 907 as shown in FIG. 15. Block 907 contains a cylindrical passage 909 within which is inserted a stainless tube 911. The upper end of the stainless tube 911 is connected, as by Tygon tubing 912, to nipple 906 which connects with the cell 71. The cell itself rests on a plastic V-block 913 attached to the top of the block 907. A cover 915, also of aluminum and containing a cavity 917 for the block 913, cell 71 and associated tubing, is placed atop the block 907 and bolted in place. A cutout 919 in block 907 contains a thermistor 921. Attached to the side of the block below the thermistor is a heat pump 923 which will preferably be a Peltier device such as Borg Warner part no. 930-17. The leads from thermistor 921 are provided to a control device 925 which provides outputs to operate the heat pump 923 in conventional fashion. On the other side of the heat pump 923 is a further metal block 927 having a passage 929 through which water is directed to remove heat from the heat pump when it is operating in a cooling mode. The whole arrangement is surrounded with insulation 931 which may comprise, for example, plastic foam insulation. The heat pump 923 controls the temperature of the aluminum block 907 to the desired value. This results in the recess space 917 being approximately at the desired value, i.e., it is close enough to this value to provide accurate results. However, as noted above, the sample must not change its temperature during measurement. The use of the silver cell and its isolation through the plastic V-block 913 assures this. The high thermal conductivity of the silver causes it to reach an equilibrium temperature with the sample very quickly during the period shown as being between $t1$ and $t2$ on FIG. 17 to be described below. The heat pump will proportionally change the temperature of the aluminum block slightly, i.e., as the temperature of the block drops a small amount, the heat pump will increase its heat flow to bring it up. The temperature does not vary much but this small variation would be sufficient to effect the measurement if felt at the cell. The imposition of the plastic V-block 913, which is a good insulator, prevents these small variations in the block 907 from reaching the sample cell 71, i.e., it acts as a thermal filter.

The essential requirement for the cell is that it have high thermal diffusivity, i.e., the time for reaching temperature equilibrium in the cell must be short as compared to the time required for transfer of the sample through the heat exchanger.

COMPUTATION

Figure 16:
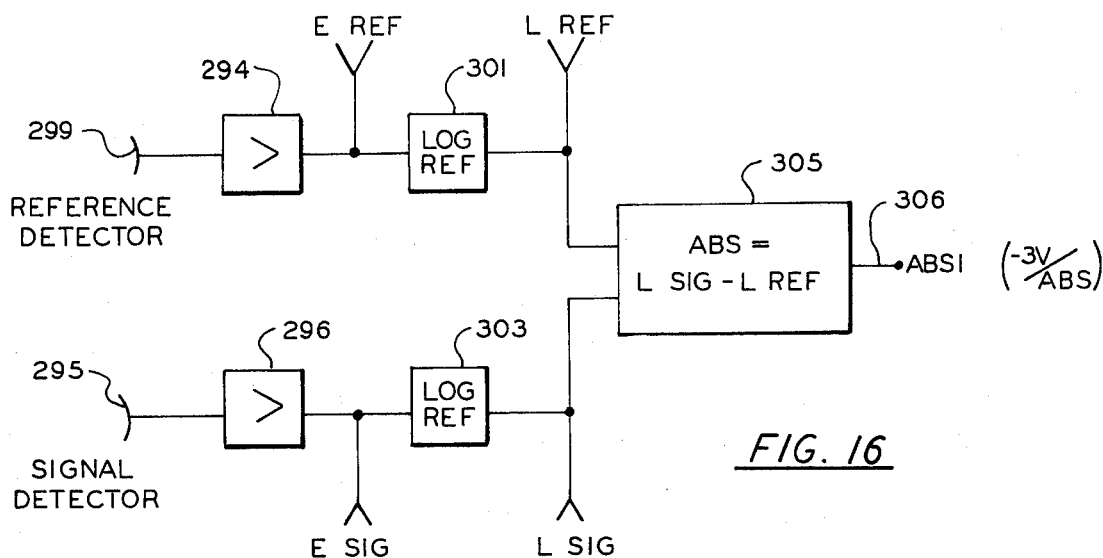
FIG. 16 is a block diagram illustrating the pre-amplifier used for processing the output of the photometer of FIG. 13.

A basic block diagram of the pre-amplifier arrangement in the computation section of the analyzer is shown on FIG. 16. Once again, the detectors 299 and 295 are shown along with the amplifier stages 294 and 296. The amplifiers respectively are provided with test point outputs indicated "E ref" and "E sig." These outputs are also provided into a logarithmic circuit, the logarithmic circuits being designated 301 and 303. Circuit 301 takes the log of the reference detector output and circuit 303 the log of the signal detector output. These two logarithmic signals are also provided as outputs to test points designated "L ref" and "L sig." From these two values, the absorbance is calculated by subtracting in an analog subtractor 305 the logarithm of the reference signal from the logarithm of the measurement signal. The output then is provided on a line 306 and, as indicated, is scaled such that it is $-3$ V per absorption unit. A circuit which may be used for this purpose is described in Application Ser. No. 499,855 of John G. Atwood et al., filed on Aug. 22, 1974, and entitled "Photometric Measuring Apparatus."

For accurate operation, it is necessary that the feedback element providing the logarithmic function be maintained at a constant temperature. Thus, the printed circuit board on which the preamplifier is mounted is installed within a thermostated metal block much in the same manner as the sample cell shown above on FIG. 15; that is, it is inserted in a recess between a bottom block and a cover and a separate heat pump, sensing thermistor and control device provided to maintain it at the desired temperature of 30° C.

Before describing how the computation is performed using the output of the preamplifier of FIG. 16, the quantity which is desired to be measured must be considered. What occurs after the two reagents are mixed together with the sample is a change in optical absorptivity of the reacting mixture. After a startup period, this change should occur linearly until the reagent is used up, at which time, the change will taper off. The change may be an upward change or a downward change depending on the particular test being run, i.e., the absorptivity may increase or decrease during the reaction. The measure of the serum activity is determined by the rate change. In order to have an accurate indication of the rate of change, it is necessary to ensure that the rate is being measured on a linear portion of the curve. To do this, a curvature measurement must also be made. As will be explained in more detail below, the rate and curvature are measured simultaneously by the apparatus of the present invention. This is in contrast to prior art apparatus which first did a curvature check and then measured rate. A disadvantage of this prior method was that a portion of the limited reaction time available for measurement had to be used up in making the curvature measurement leaving only the remaining portion for the rate measurement. A second disadvantage was that an allowable curvature needed to be preestablished before knowing the rate produced by any sample. The present invention on the other hand establishes allowable curvature as a function of the rate and thus can test samples which would otherwise be rejected by prior art apparatus. In particular, it allows a sample with a higher rate to have higher curvature so that maximum allowable error due to curvature is fixed percentage. More importantly, it uses the full measurement time available. It does this in a number of ways as will become apparent as this description proceeds.

Figure 17:
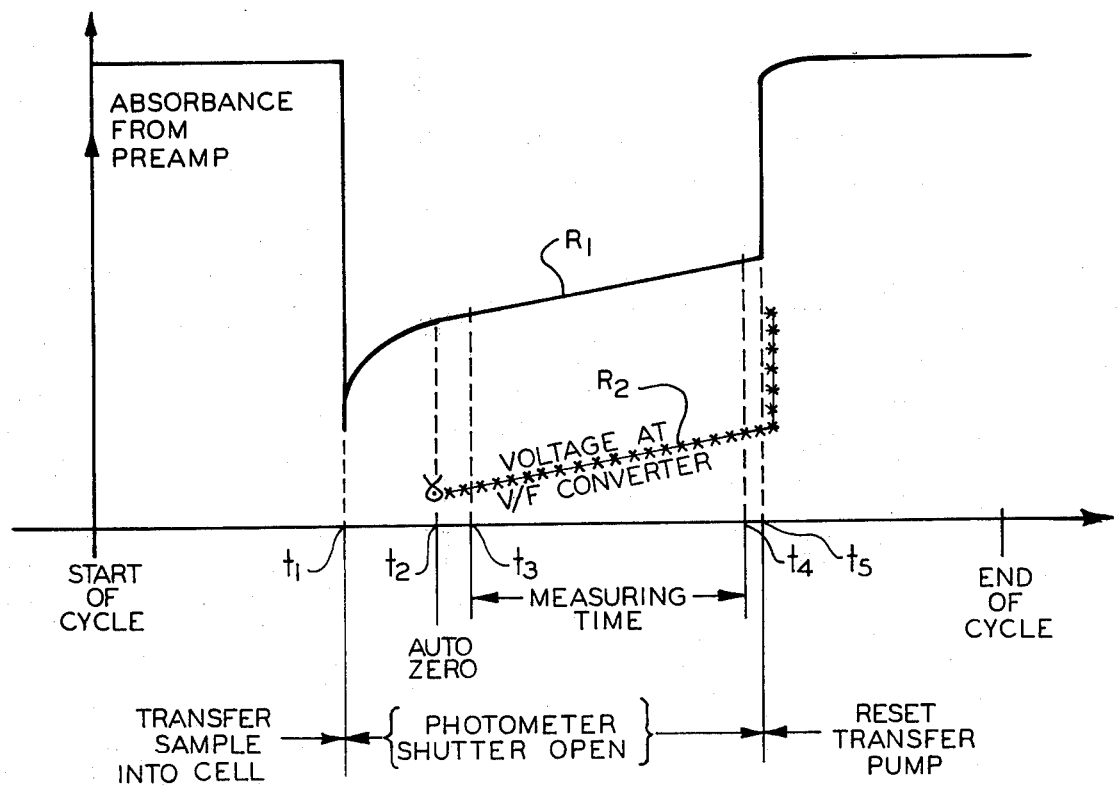
FIG. 17 is a timing diagram illustrating the operation of a measurement cycle.
Figure 18:
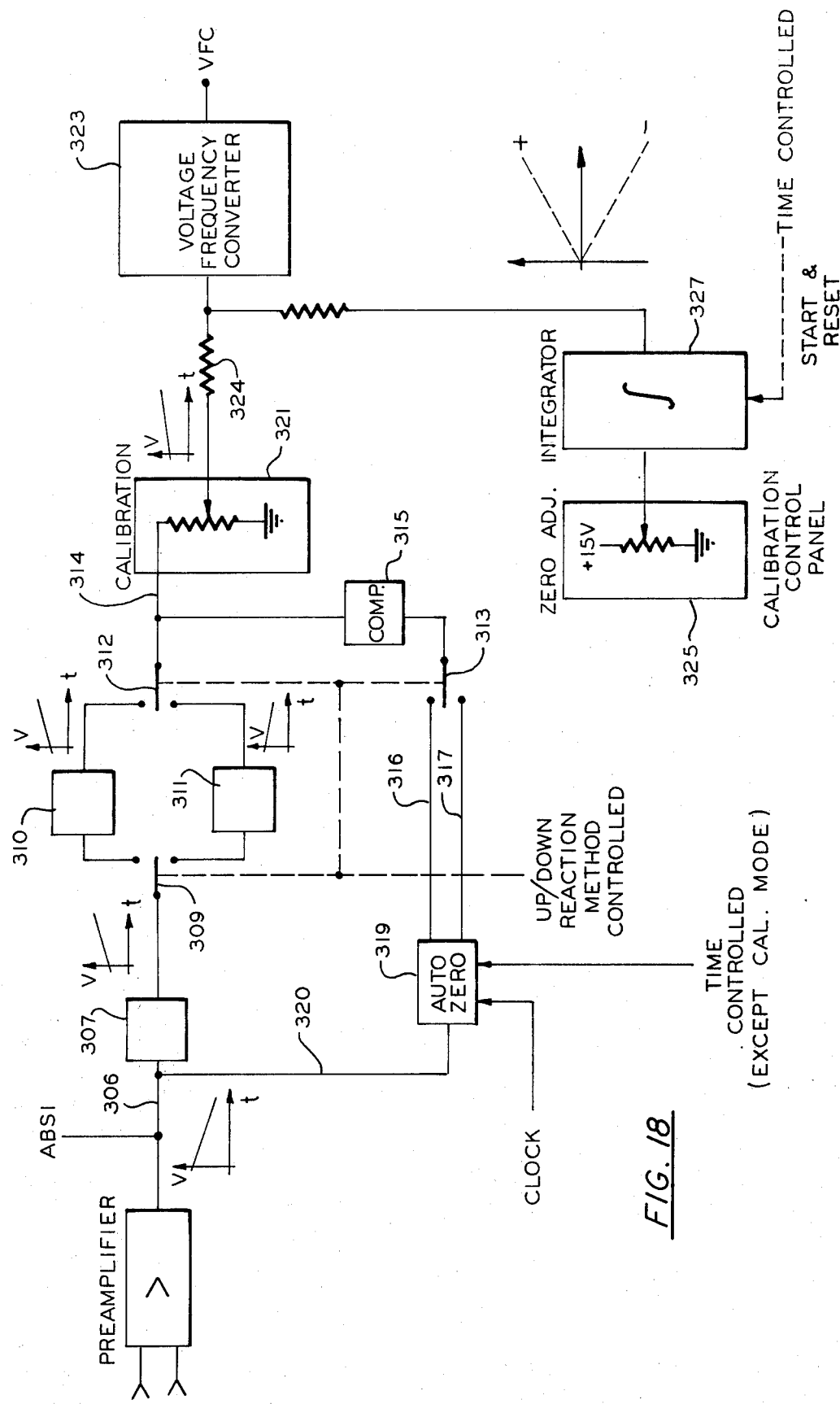
FIG. 18 is a block schematic diagram illustrating the auto-zeroing of the output of the pre-amplifier of FIG. 16 and its conversion to a frequency.

An understanding of the measuring system can best be obtained through an examination of FIG. 17 and FIG. 18. FIG. 17 illustrates the measuring cycle. As explained in conjunction with FIG. 13, shutter 284 remains closed until the reacting mixture is in the cell. On FIG. 17, the output from the preamplifier is shown as being at a maximum with the shutter closed. The shutter is opened at a time $t1$. Nothing is done immediately. This allows everything to stabilize for a short period. At time $t2$, an auto-zero cycle is started. The curve R1 shows the manner in which the preamplifier output will change without auto-zero. The curve R2 shows the effect of auto-zero. Auto-zero brings the level of the curve down near zero so that the measurement can be carried out at a higher gain than would ordinarily be possible. After the end of auto-zero, at time $t3$, measuring begins and continues until time $t4$. Thereafter, at time $t5$, the shutter is closed and the transfer pump goes through its reset cycle.

Referring now to FIG. 18, the output on line 306 is provided to a further amplifier stage 307. It is then provided to a first switch 309 which can couple it either to an amplifier 310 with a gain of $+2$ db or an amplifier 311 with a gain of $-2$ db. This is only a symbolic amplifier change. Actually, the amplifiers, 310 and 311, are one amplifier used in the described manner. Since the voltage to frequency converter at the output of the system can only operate at one polarity, it is essential that only positive signals be provided at that point. Thus, if the sample being tested is one having a decreasing or down reaction, inversion is necessary. A second switch 312 which operates with switch 309 is also provided at the output of the amplifiers 310 and 311. These two switches can, of course, be a transistor or FET switch rather than mechanical switch. A third switch, also coupled to switches 309 and 312 are designated 313, is also provided. This switch, which can be a logical gate, couples the output of a comparator 315 which has as its input the output on line 314 from one of the amplifiers 310 or 311. Comparator 315 is preset to a value close to zero, e.g., $+0.7$V. A comparator output is provided on one of the lines 316 or 317 to an auto zero logic circuit 319. The output of the auto-zero logic circuit 319 is provided as a second input to the summing junction of the amplifier 307. Within the auto-zero block 319 are contained counters, a digital to analog converter and appropriate gating. Its operation is a type well known in the art with the counters enabled to count clock pulses until the threshold of a comparator 315 is exceeded at which time, the count is stopped. The count stored in the counter is an input to the digital to analog converter whose output is the output on line 320 which is added to or subtracted from the input on line 306. Thus, a counter will be caused to count until an output is provided on line 320 which brings the output of the amplifier 307 near + 0.7V. Clearly, other types of auto-zeroing can be used. It will be recognized that what is being carried out is a closed loop integration and that in place of a clock and counter an analog integrator or motor integrator may also be used.

The output which is now near zero is provided through a calibration potentiometer 321 through an input resistor 324 to the input of a voltage-to-frequency converter 323. Although not shown, separate calibration potentiometers are provided for each wavelength and in conjunction with test selection will be switches in the circuit in conventional fashion using relays or semiconductor switches. Because a small slope can occur, i.e., an apparent change in absorption, which is not the result of the chemical reaction due to the sample being measured, compensation to offset this unwanted slope is also provided. Thus, there is included a zero adjust potentiometer 325 which is a input to an analog integrator 327. The integrator output is summed at the input to the voltage-to-frequency converter 323 with the signal from the calibration potentiometer 321. It is, of course, selected to be in a direction opposite to the unwanted slope. The integrator is started and reset by appropriate outputs from the timer. The voltage-to-frequency converter will convert the analog signal present at its input to an output whose frequency is proportional to the analog magnitude in well known fashion. A typical voltage-to-frequency converter which may be used for this purpose is type 1700-5044-00 from Anadax Instruments Inc.

Figure 19:
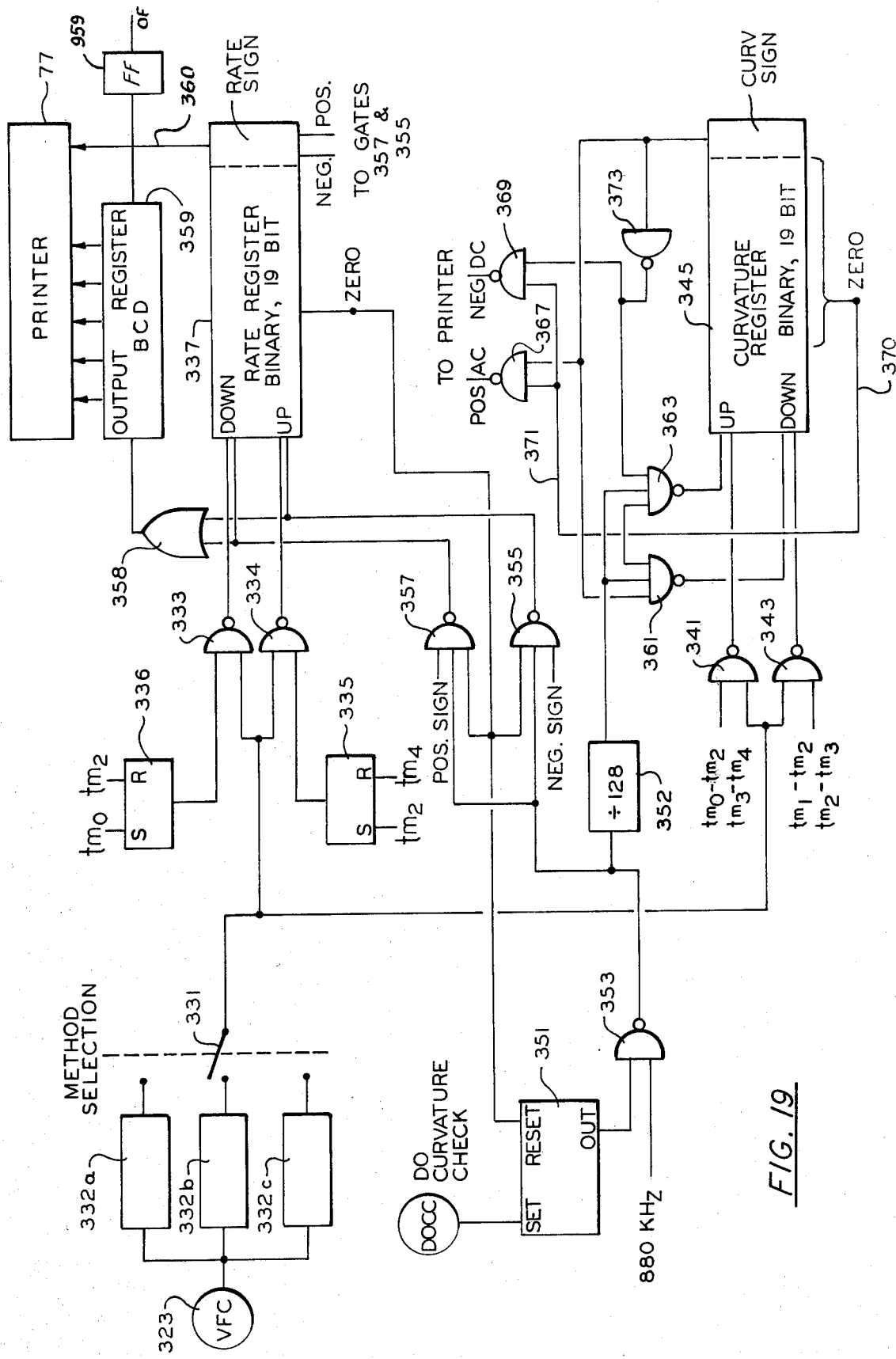
FIG. 19 is a logic-diagram illustrating the manner in which the frequency output is used to calculate rate and curvature.
Figure 20:
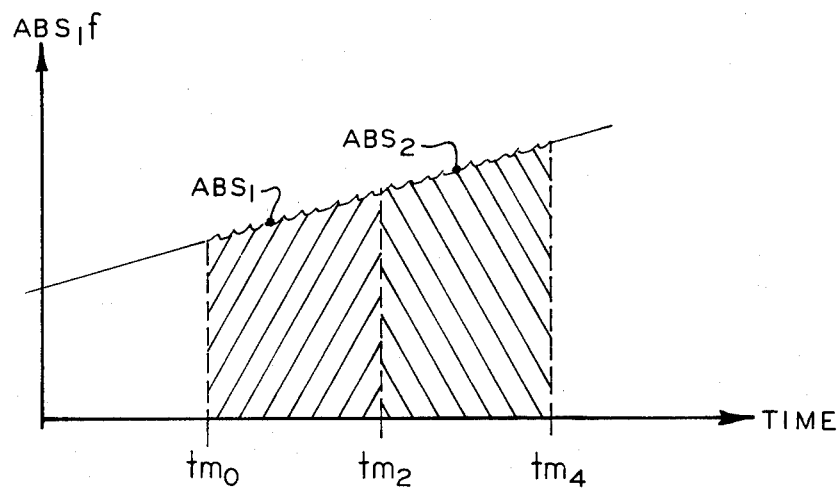
FIG. 20 and 20a are diagrams helpful in understanding the operation of the apparatus of FIG. 19.

FIG. 19 illustrates the manner in which rate and curvature are calculated and FIG. 20 is a curve illustrating the manner in which the signal changes during the measurement period. As noted above, it is the rate of the change of absorption which is to be measured. Referring to FIG. 20, the output of the voltage-to-frequency converter 323 is provided to three dividers. The dividers designated 332a and 332b and 332c divide the frequency by predetermined factors depending on the test selected. As noted above, Table IV in FIG. 12 indicates the various parameters associated with each of the individual tests.

The divider 332a is associated with the photometer source wavelength of 340 nm and the divider 332b with the wavelength of 404 nm. The final divider 332c is used in conjunction with the auxiliary test and may be preset to divide by a number N/10,000. The output of one of these dividers, depending on which test is selected, is provided through a switch 331 to a pair of gates 333 and 334. These gates are enabled respectively by signals from flipflops 335 and 336. The flipflops are set and reset by outputs from the timer. Thus, at the time $t_{m0}$ (see FIG. 20 and Table II), flipflop 336 is set to enable the gate 333. Pulses output from the gate are provided as a down input to a rate register 337 comprising a binary up-down counter. As long as the gate is enabled, the counter counts down. With reference to FIG. 20, it counts down for the period between $t_{m0}$ and $t_{m2}$. This corresponds to one-half the measurement cycle. It will be recognized that this has an integrating and averaging effect in the signal which, as illustrated, is not flat but contains noise. The signal is integrated so as to obtain an average value cancelling out much of the noise. The value in the counter at the end of the first half of the time period at time $t_{m2}$ will be proportional to the average absorbance value over that period (ABS 1 indicated on FIG. 20). At this point, flipflop 336 is reset and flipflop 335 set to enable gate 334. The counter now counts up. The number of up counts will be proportional to the average value during the time between $t_{m2}$ and $t_{m4}$ or, in other words, the value ABS 2 shown on FIG. 20. The down count followed by the up count effectively carries out a subtraction of the two counts so that the remaining value in the register will be the difference between ABS 1 and ABS 2. This difference clearly is proportional to the slope. Thus, the value stored in register 337 at the time $t_{m4}$ will be an indication of the rate of change of absorption, the desired value. Note that measurement occurs during the full period and is averaged thereover to eliminate errors due to noise. In contrast, prior art systems generally measure only at two points to compute slope and are thus subject to large errors due to noise.

Figure 20A:
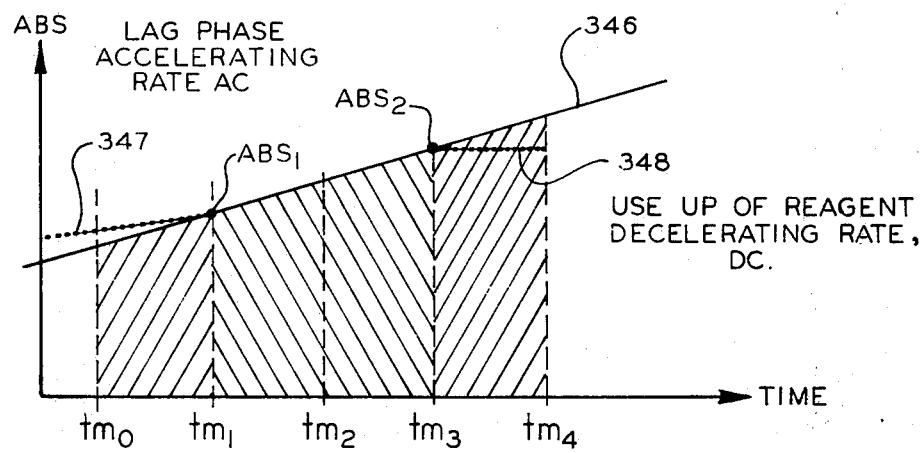

As indicated above, the rate is not valid unless it has been measured on a linear portion of the curve. Thus, a curvature check must also be made. The output of divider 332a, b or c through switch 331 is also the input to two gates 341 and 343. Again, the outputs of the gates are inputs to a register 345, which is the curvature register. FIG. 20a is helpful in understanding the manner in which the curvature determination occurs. Shown is a linear curve portion 346 and in dotted lines at the beginning what is referred to as a lag phase 347 and at the end of the curve a decelerating rate or use up of reagents designated 348. The time is broken up into four periods, the first defined by $t_{m0}$ and $t_{m1}$, the second by $t_{m1}$ and $t_{m2}$, the third by $t_{m2}$ and $t_{m3}$, and the fourth by $t_{m3}$ and $t_{m4}$. Times $t_{m0}$ and $t_{m2}$ and $t_{m4}$ are the same times referred to above in connection with FIG. 20.

Flipflops similar to flipflops 335 and 336 will be provided to enable gates 341 and 345 to pass pulses from the voltage-to-frequency converter 323 after being divided and coupled through the switch 331. Gate 341, enabled from the time $t_{m0}$ and $t_{m1}$ and from the time $t_{m3}$ to $t_{m4}$, is coupled into the up count input of a curvature register 345. Gate 343 having its output coupled to the down input of curvature register 345 is enabled from the times $t_{m1}$ to $t_{m2}$ to $t_{m3}$. Examination of FIG. 20a will show that if the curve is perfectly linear, this will result in a net count of zero. A positive net count will occur for an accelerating rate or lag phase such as lag phase 347 shown on FIG. 20a. A negative sum will result for a decelerating rate or use up of reagent indicated by 348 on that figure.

After the end of the time period as indicated by $t_{m4}$, a command (DOCC) from the timer, indicating that a curvature check should be performed sets a flipflop 351. Flipflop 351 enables a gate 353 to pass an 880 Khz pulse train which is provided to the inputs of gates 355 and 357. Each of these gates is enabled by an output from the rate register 337. These gates will be enabled by a condition in rate register 337 indicating non-zero, e.g., the least significant bit output may be used. Gate 357 has a second enabling input the positive sign obtained from the rate sign section of rate register 337. Similarly, gate 355 is enabled by the negative sign. The output of gate 355 is coupled to the up input of the rate register 337 and that of gate 357 to the down input. The two lines are also provided to an OR gate 358 having its output coupled as an input to an output register 359 which is a BCD register providing a BCD output to the printer 77. The output of gate 353 is also divided by 128 in a binary divider 352 and provided to gates 361 and 363. These gates are enabled by the zero output of the curvature register 345 and respectively by the positive and negative sign outputs from that register. As shown, the positive and negative indications may be developed by taking the positive sign directly from the register and by obtaining a negative sign indication through an inverter 373. The output of gate 361 is coupled to the down input of register 345 and the output of gate 363 to the up input. Thus, in each case, the register 337 or 345 will be counted in a direction to cause it to approach zero. If it contains a positive count, it will be counted down and if it contains a negative count, it will be counted up. Counting begins with the setting of flipflop 351. The 880 Khz signal will be provided to register 337 counting it toward zero and at the same time will be provided to register 359 causing its count to increase until the rate register reaches zero. At this point, the gates 355 and 357 will be disabled and the flipflop 351 reset. If prior to this point, the curvature register reached zero, its zero output will disable the gates 361 and 363 causing it to remain at zero count. Thus, if after the rate has been loaded into the output register, a count remains in the curvature register 345, the curvature is too great and an indication of this should be given. This will be indicated by an output remaining on line 370 which is provided to gates 367 and 369 on line 371. Gate 367 has as a second input the positive sign output of register 345 and will be indicating an accelerating rate. An output from gate 369 indicating a decelerating rate will occur when a non zero output is present on line 371 and a negative sign output as indicated by an output from inverters 373, is present at its second input. These outputs are then provided to the printer to cause it to print an error message. Table IV illustrated on FIG. 12 shows the setting of the various parameters for different tests; reference is made in the column headings of Table IV to the figures previously described and the element affected.

Although the curvature check has been disclosed in connection with an essentially linear rate of change, it is possible through a simple modification to check the curvature on non-linear curves. This may be done in a simple fashion by changing the scale factor within each of the four measuring periods. Basically, two methods of accomplishing this exist. The four periods can be divided up into unequal sections designed to end up with a zero count if the measured curvature follows a predetermined curvature. The other solution comprises keeping constant time intervals and changing the amplification or scaling of the count during each of the four quarters. Such scaling may be done in simple fashion by using appropriate divide-by-N counters.

Figure 21:
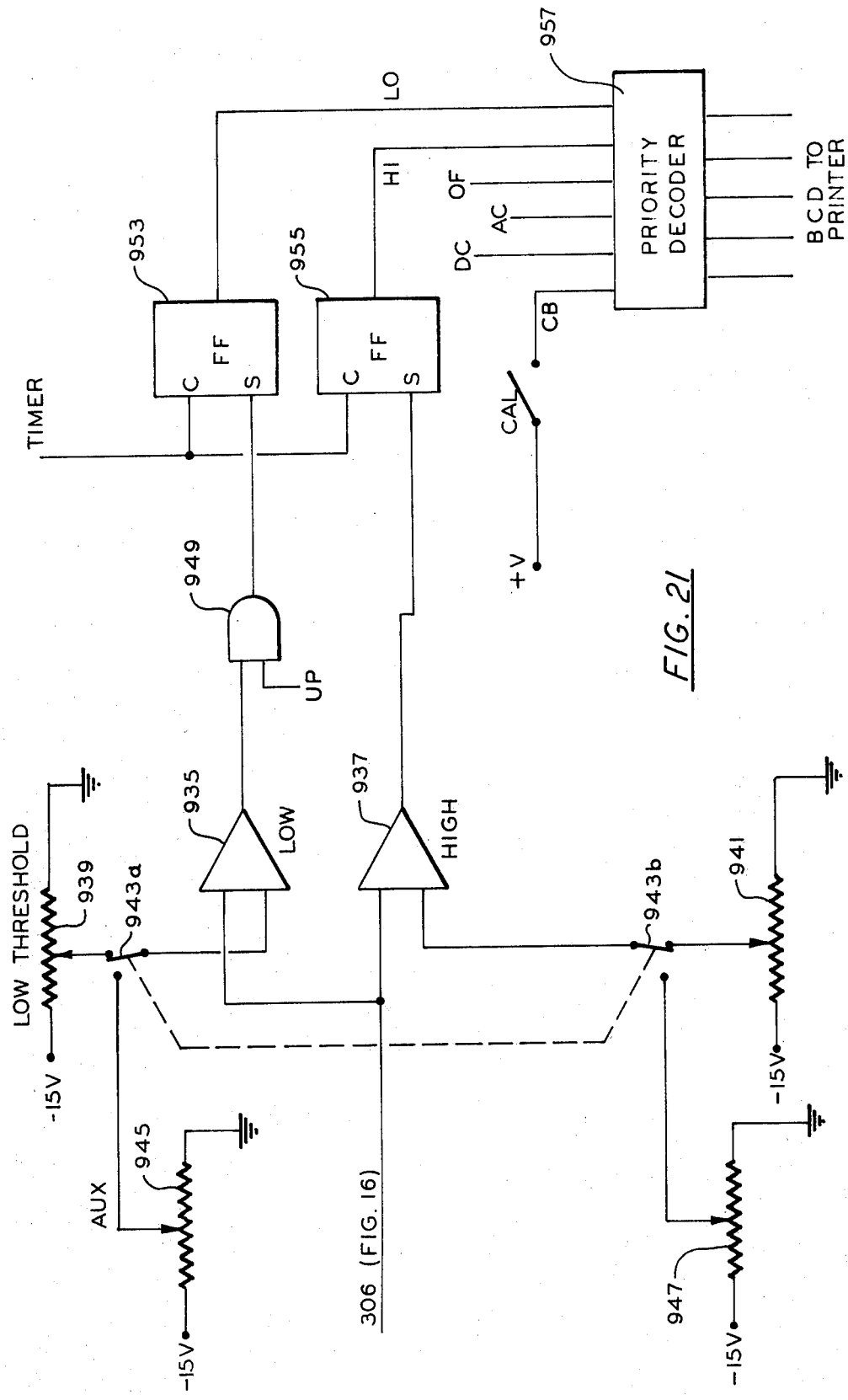
FIG. 21 is a logic diagram illustrating the detection of upper and lower and limits and operation of the priority decoder.

FIG. 21 shows the high and low threshold detector along with the error generation circuitry. Specific high and low thresholds are set in and cover all tests. If these thresholds are exceeded, it is an indication that the desired reaction has not properly taken place and the printed rate is not reliable. The output (ABS 1) on line 306 of the preamplifier stage shown on FIG. 16 is provided to two comparators 935 and 937. The second input of these comparators is respectively the output of a potentiometer 939 and of a potentiometer 941. Potentiometer 939 is coupled between −15V and ground and potentiometer 941 between −15V and ground. They are initially adjusted to provide a desired threshold level. Also shown is a switch having two poles designated 943a and 943b. As with all switches in the apparatus, these will preferably be electronic, such as FET switches, although shown for purposes of simplicity as mechanical switches. When operating from the auxiliary panel, these switches will couple the potentiometers 945 and 947, instead of 939 and 941, respectively, to the threshold comparators 935 and 937. Thus, when operating in the auxiliary mode, thresholds may be set up by the operator as desired. The output of comparator 935 is provided to an AND gate 949 which is enabled by an up signal indicating a down reaction in accordance with the test selection shown on Table IV. The output of gate 949 is provided to flipflop 953. Output from comparator 937 is provided to flipflop 955. These flipflops are clocked by an appropriate timer output. Thus, at the proper time for checking thresholds, a timer output appears at the flipflops and if an error is indicated by 949 or by comparator 937, the appropriate flipflop is set. The output of flipflop 953 thus indicates a low threshold and that of 955 a high threshold.

These two outputs are provided as inputs along with additional inputs to a priority decoder 957. The additional inputs include an overflow indication, "OF," from a flipflop 959 coupled to the last stage of the output register 359 of FIG. 19. If this flipflop is set, an overflow situation exists and indication thereof must be given. The next two additional inputs are AC, accelerating rate, and DC, decelerating rate, obtained from the gates 367 and 369 of FIG. 19. The final input is designated CB and is obtained from a switch which is closed when calibration is in progress. The priority decoder 957, which may be a Texas Instruments SN74148, will automatically select the error of highest priority when more than one error is present. The priority of the error signals is the order on the figure. Priority decoder 957 then provides a BCD output to the printer causing it to print an error message next to the rate printout obtained from register 395. In addition, presence of an error signal results in the line being printed in red.

AUXILIARY PANEL

Figure 22:
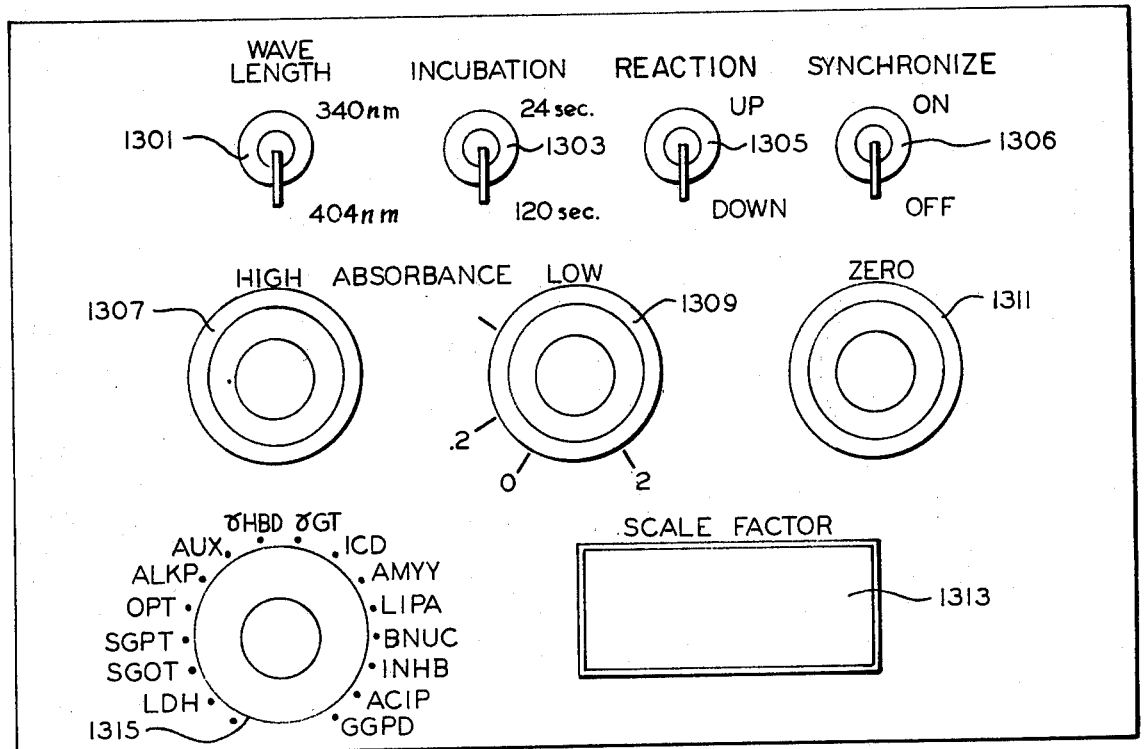
FIG. 22 is a front view of the auxiliary panel.

FIG. 22 illustrates a front view of the auxiliary panel. As noted above, it is possible to select the auxiliary mode in which the various parameters may be set to desired values. Thus, there is shown on the auxiliary panel a number of controls for setting up these parameters. First, a switch 1301 is provided for selecting either the 340mm or 404mm wavelength photometer source. Next, there is a switch 1303 for selecting either a 24-second or 120-second incubation period. This determines at which point in the analyzer section the reaction mixture is transferred into the photometer cell as described above. The next switch 1305 is used to select the type or reaction expected, either up or down. The fourth switch 1306 is for synchronizing the timing of the preparation unit and analyzer unit as described above. Two dials 1307 and 1309, provided for setting in the high and low limits of absorbence, enable control of potentiometers 945 and 947 shown on FIG. 21. Also provided is a calibration control 1311 which sets the potentiometer 325 (FIG. 18) for auxiliary operation. A push-button switch 1313 is provided for setting in the scale factor and a multi-position switch 1315 to provide an appropriate command to the printer to print out the type of test being run.

DILUTER PUMP

Figure 23:
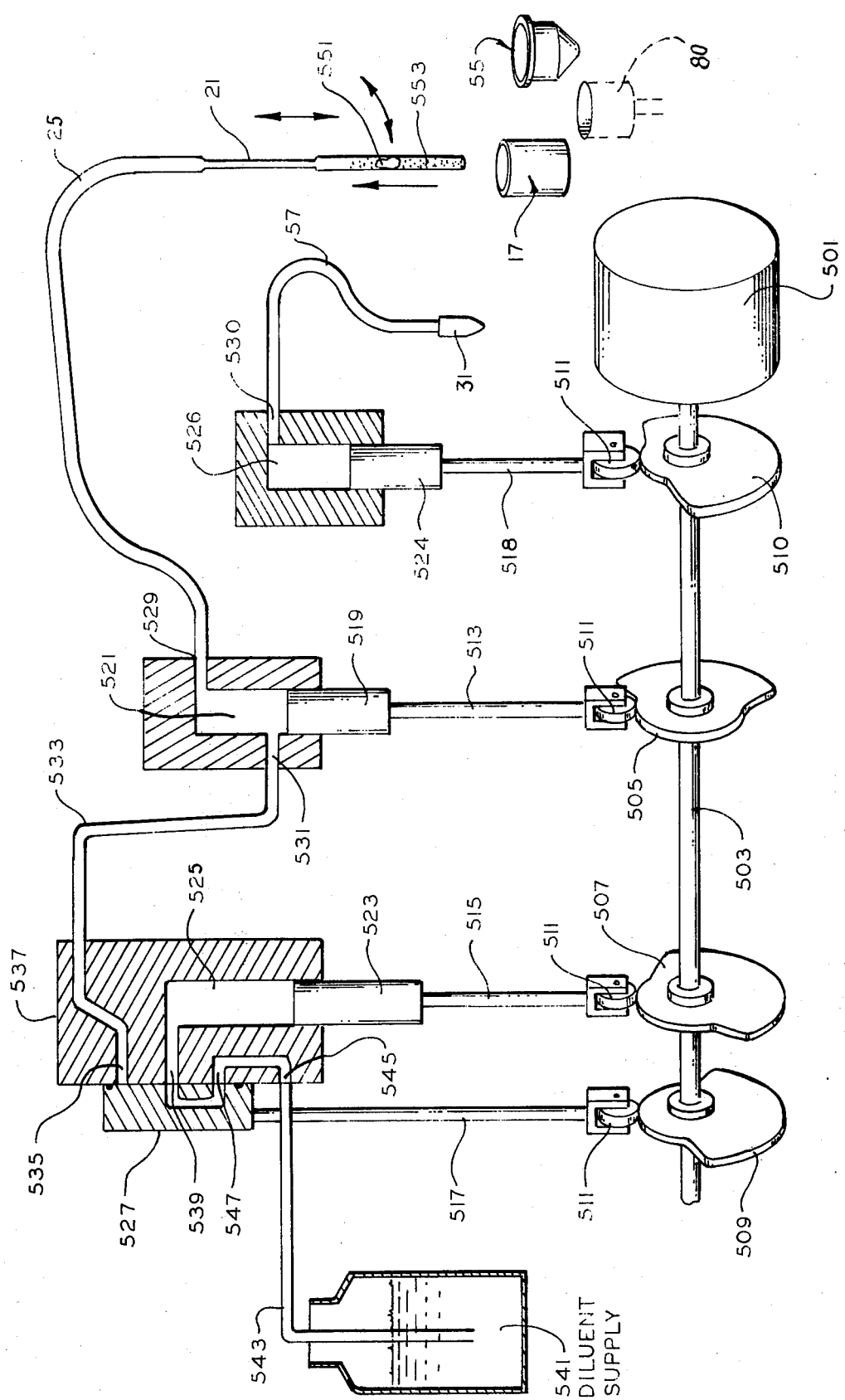
FIG. 23 is a schematic illustration of the diluter pump and pipetter pump of the present invention.

FIG. 23 is a schematic perspective view illustrating the manner in which the diluter system operates. It includes a motor 501 energized and controlled by a circuit such as that shown on FIGS. 6 and 7 and herein before described. (Reference should also be had to Table I, above, which indicates the cycles of operation.) On the shaft 503 of motor 501 are four cams 505, 507, 509 and 510, respectively. Engaging the profile of each of the cams are respective cam followers 511 attached to push rods 513, 515, 517 and 518. On the ends of rods 513, 515 and 518 are respective pistons 519, 523, 524, operating within the cylinder bores 521, 525 and 526. Rod 517 has on its end a slide valve 527. (Cylinder bore 521 has an outlet 529 which is coupled by the tube 25, also shown on FIG. 1, to the sample probe 21.) Another inlet to the cylinder 521, designated 531, is coupled by a tube or hose 533 to a port 535 in the block 537 containing cylinder bore 525. This is a port which can be coupled through the slide valve 527 to a further port 539 which opens into cylinder bore 525. A bottle 541 filled with diluent is coupled through an appropriate tube 543 to a further passage or port 545 which has an opening 547 which can also communicate with the slide valve 527.

A port, 530 connects the bore 526 via tube 57 to the pipetter 31. Piston 523 and cylinder bore 525 constitute the diluter pump and piston 519 and cylinder bore 521 the pump for drawing in the sample of serum. Piston 524 and cylinder bore 526 form the pump for the first pipetter.

As shown in Table I, at time 0.1, the pipetter drive is started to move the pipetter into position in the reagent bottle; at time 0.9, the pipetter motion is stopped and the diluter pump started. The motor 501 rotates cam 510 causing the piston 524 to move downward drawing reagent into the pipetter 31. The system contains only air with a partial vacuum being created by the piston motion to draw the reagent into the pipetter 31. Thus, reagent is present only within the interchangeable glass pipette 31. At time 1.5, the diluter probe is started with its drive moving it from the resting position over the flushing station (80, FIG. 1) to a position over the sample. At time 2.1, the pipetter is started again to move it from the reagent bottle to a position over the reaction cup in the magazine. At time 3.4, the diluter pump is stopped and at time 4.0, the diluter probe is stopped.

At the beginning of the cycle, the piston 519 was at the upper limit of travel. At time 2.1, when the pipetter drive starts to withdraw the pipetter from the reagent and move it to the reaction cup, a flat on its associated cam 510 is reached to stop downward travel of piston 524 to prevent further drawing in of reagent. Rotation of the shaft 503 continues, however, to drive the cam 505 associated with the piston 519 to cause a small air bubble 551 to be drawn into the probe 21 before it reaches the serum sample. At time 4.0, the dluter probe is stopped in the serum sample and at time 4.6, the diluter pump started again. At time 4.8, the pipetter is stopped, now in position over the reaction cup. Restarting of the diluter pump results in the piston 519 being moved farther down in the bore 521 to draw into the probe the required amount of serum 553. During operation of the diluter system including the sample takeup pump and diluter pump, all conduits are always filled with water except for the air bubble 551 described above. Thus, as the piston 519 is drawn farther down in cylinder 521, water in the tube 25 will be drawn into the cylinder. The remainder of the tube 25 will be filled with water except for the air bubble 551 and the serum sample 553. At a time after the time 4.8, when the pipetter is stopped, motion of the cam 510 will drive the piston 524 upward to discharge the reagent contained within the pipette 31. At time 6.1, the diluter probe motion is started again, the pipetter is started to return it to the reagent and the diluter pump is started. At this time, the full sample will be in the probe.

During this beginning portion of the cycle, the valve 527 was maintained in the position shown and the piston 523 moved from its uppermost to its lowermost position drawing diluent from the container 541 through the tube 543, and ports 545 and 539 into the cylinder 525. The diluter probe which started movement at time 6.1 is caused to raise and rotate to a position over the reaction cup. At time 7.9, the pipetter stops over its reagent. At time 10.1, the diluter pump motor is started again causing the valve 527 to move to the upper position coupling the ports 535 and 539 and closing off the port 547. Also at this time, a small amount of remaining reagent is discharged from pipette 31 to its associated sponge 39. At this point, the diluter probe is moving down into the reaction cup. The probe is stopped at 10.9 but the diluter pump is still running, cam 507 driving the piston 523 upward. The piston 519 is now in the position shown in FIG. 23 so that the diluent is pumped out of the cylinder 525, through the port 539 and valve 527 into the port 535, through the tube 533 and the cylinder 521 and out through the port 529 into the tube 25. This results in the serum sample being pumped into the reaction cup in the magazine. Because of the greater displacement of the piston 523, not only is the sample pumped out but a measured quantity of diluent along with it. However, the pumping stroke is not completed during this cycle but is stopped with piston 523 in a partially raised position. Note that at this time, the complete system contains water. At time 13.5, the diluter probe is started again and at time 13.9, the diluter pump is stopped. The probe rotates until it is over the flushing receptacle 80 which occurs at time 15.4 whereupon the diluter pump is started. The probe will have stopped because of a light sensing operation such as described above in connection with FIG. 6 and FIG. 7. The diluter pump starts again with the piston 523 moving the rest of the way up to rinse out the probe. It will be stopped when motor 501 is stopped by an angular sensor of the type described above. This will occur approximately at the time 16.8 which is the end of the cycle. The motor is then ready to start another cycle in response to a new timer output. Note also that at 15.4, an output indicated as move go is provided. This is the output which advances the magazine longitudinally to place the next reaction cup in position and advances the sample platter to place the next sample cup in position.

THE TRANSFER PUMP

Figure 24:
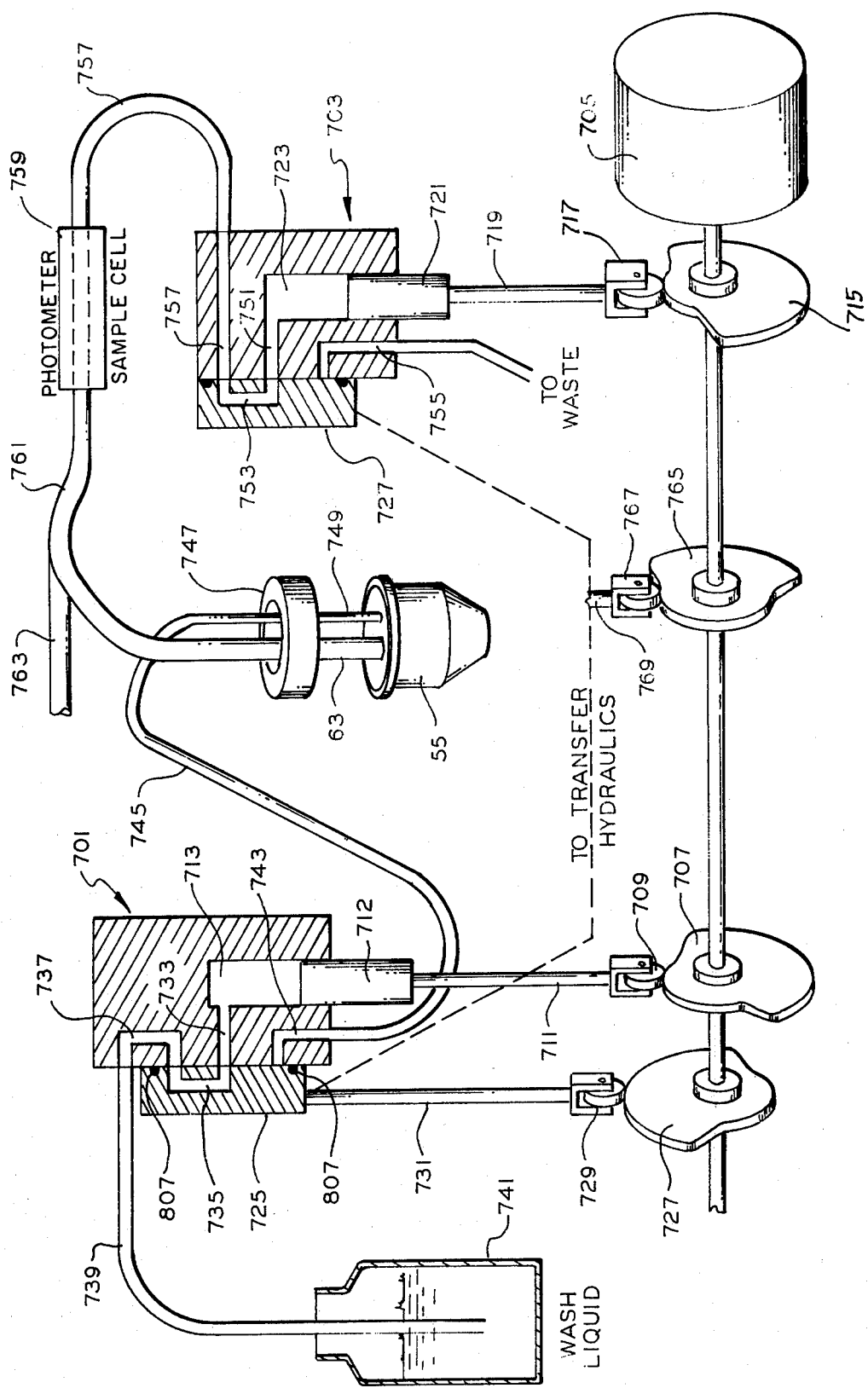
FIG. 24 is a similar illustration of the transfer pump.

FIG. 24 illustrates the construction of the transfer pump. Once the serum specimen has been mixed with the two reagents, stirred and allowed to incubate for the required period of time, the transfer mechanism must pick up the proper amount of the reaction mixture, transfer it to the photometer cell where it is analyzed, and then wash out the transfer system in preparation for the next sample. Thus, on FIG. 24, there are shown two pumps, one of which is a wash pump indicated generally as 701 and the other of which is the transfer pump designated 703. As with the pumps associated with the diluter and the first pipetter, these pumps are driven by a motor 705 having cams on its shaft. Pump 701 is driven by a cam 707 coupled through a cam follower 709 and push-rod 711 operating a piston 712 with a cylinder 713. The pump 703 is driven by a cam 715 engaged by a cam follower 717 on the end of a push-rod 719 which operates a piston 721 within cylinder bore 723. A slide valve member 725 associated with the pump 701 and a slide valve member 727 with pump 703 are jointly driven by a single cam operating through an appropriate cam follower 729 and push-rod 731.

Cylinder 713 has a port 733 which, depending on the position of valve member 725, can be coupled via passage 735 in the valve member either to a passageway 737, from which a tube 739 extends into a wash liquid container 741, or to a passage 743. Passage 743 is coupled by way of a conduit 745 to the sponge unit 747 through which the probe 63 extends. A tube 749, extending from conduit 745, is formed into the plastic sponge holder of unit 747 and terminates at a position above reaction cup 55. Transfer pump 703 has a port 751 which, depending on the position of valve member 727, can be coupled via valve member passage 753 either to an outlet passage 755 leading to a waste container or to a passage 757 which is coupled through appropriate tubing 757 to one end of photometer cell 759, the other end of which is coupled by appropriate tubing 761 to transfer probe 63 which is supported on an arm 763 to be described in more detail below.

At the beginning of the cycle, the valve 727 will be in its uppermost position (as shown in FIG. 24) coupling port 751 with passage 757, and piston 721 is near the top of its stroke in cylinder 723. At this point, the previous sample is within the cell 759 and a quantity of wash liquid in the probe 63 and tubing 761; the manner in which this occurs will become evident from the following description. The cam 715 is constructed so that it first causes piston 721 to move upward slightly displacing the liquid within the tubing 757, cell 759, tubing 761 and probe 63 a slight distance toward the cup 55. The purpose of this slight movement is to dislodge any solid material which may be lodged in the system. Piston 721 then begins its downward stroke creating suction at probe 63; simultaneously, the probe itself is caused to oscillate up and down, by apparatus to be described presently in connection with FIG. 25. (This apparatus is driven by motor 705 through a cam 765, cam follower 767, and pushrod 769 which appear in FIG. 24.) Probe 63 dips into the sample eight times, picking up a small volume of sample each time. Each oscillation carries the probe a littler farther down as the sample level falls and finally the probe goes all the way to the bottom of reaction cup 55 and remains for a longer period of time so as to draw a sufficient quantity of sample to fill the photometer cell. The result is eight small slugs of sample separated by air bubbles followed by the large sample slug for analysis. The large slug of the sample is approximately 25 microliters and more than fills the 18 to 19 microliter capacity of the photometer cell 759.

At this time, the valve member 725 is in a position to couple port 733 to the outlet passage 743 and piston 712 is driven upward in the cylinder 713 which was previously filled with wash liquid. The wash liquid is thus forced out through the conduit 745 and tube 749 into the cup 55. The transfer probe continues to oscillate and the piston 721 continues to retract drawing slugs of wash liquid separated by air bubbles into the probe 63 and tube 761. When the piston 721 reaches the bottom of its stroke, the new sample will be in the photometer cell 759 which will have been washed out previously by the wash liquid which was within the transfer probe 63 and tube 761 at the beginning of the cycle. Portions of previous wash liquid and samples will be within the cylinder 723. At this stage, the reaction mixture is properly positioned in the photometer cell and valve 727 is moved to its lowermost position sealing off passage 757 so that the reacting sample cannot move and analysis then takes place. During analysis, piston 721 is moved upwardly in cylinder 723 discharging the waste through the port 751, passage 753 in the valve member, and out through the passage 755 to waste. At the same time, valve member 725 is in the position shown in FIG. 24 and the piston 712 of wash pump 701 is caused to move downward to draw in new wash liquid through the tube 739, passage 737, valve member passage 735, and port 733 to the cylinder 713. The transfer pump is now ready for another cycle.

FIG. 25 illustrates the manner in which transfer probe oscillation is obtained. The probe arm 763 is mounted to a hydraulic piston 771 operating in a cylinder 773. An appropriate seal 775 is provided at the bottom of the cylinder in conventional fashion. The cylinder 773 has two ports designated 777 and 779. Piston 771 is spring loaded with a spring 781 which tends to push the piston upwardly withdrawing the probe 63 from the cup 55. Piston 771 is a sleeve piston driven by the displacement of a piston 783 operating in a master cylinder 785 having a port 787 connected with appropriate tubing 789 to the port 779. Cylinder 785 has a second port 791 which connects with a spindle valve 793. Other connections to the spindle valve 793 are two hydraulic lines 794 and 795 having free ends immersed in hydraulic fluid in a container 797 and a line 796 coupled to the port 777 of cylinder 773. The piston 783 is coupled through pushrod 769 to a cam follower 767 engaging cam 765 as shown on FIG. 24. The spindle valve comprises a bore 798 with two spindles 799 and 800 operating therein on a rod 801. The rod 801 is coupled to the valve cam 727 of FIG. 24.

At the portion of the cycle where the probe 63 must oscillate up and down in the sample, the valve 793 is in the position shown. In this position, the port 791 is closed off as is the connection through tube 796 with the ports 777 of the cylinder 773. The cam causes the master piston 783 to oscillate up and down with each movement bringing it closer to the top of its stroke. The slave piston, in well known fashion, follows this motion. Preferably, the diameter of the master cylinder 785 is much larger than that of the slave cylinder 773 so that a multiplication of distance will take place. In other words, a small motion at the cylinder 785 will cause a large oscillating motion at the probe 63. When all of the liquid (both sample and wash liquid) has been drawn into the probe, the valve stem 801 is moved upward by the cam coupling port 791 with a hydraulic line 794 and coupling lines 795 and 796 permitting the pressure of spring 781 to push piston 771 upward, forcing hydraulic fluid from cylinder 773 through port 777, tube 796, valve bore 798, and line 795 to the hydraulic fluid reservoir 797. During this upward travel of piston 771, fluid can flow through another path, i.e., port 779 and tube 789 to cylinder 785. However, the resistance to flow through this second path is much greater and the path of least resistance available through port 777 will be followed. Thus, the piston 771 will move fully upward under the force of spring 781 expelling essentially all the hydraulic fluid contained in cylinder 773. Note that at this time, the piston 783 is essentially at the top of its stroke and starts to move downward to draw in a new supply of hydraulic fluid through the line 794, the segment of valve bore 798 below spindle 800, and port 791 to the cylinder 785. Again, the other path through the spindle 799 and through the cylinder 773 exists. But this path will have the greater resistance so that the fluid will be drawn in through the line 794. This operation results in a circulating of the hydraulic fluid each cycle and causes any air entrapped in the system to be eliminated. It also gives the system a self-priming operation, so that after being shut down to the extent where the hydraulic fluid has drained out of the cylinders, it will still be able to start up quickly without priming.

In each case, the pumps above have been described as a piston/cylinder type of positive displacement pump. It should be noted that the basic requirement is that these pumps be positive displacement pumps and not pumps of uncontrolled displacement as were often used for carrying out similar functions in prior art applications. What is meant by a positive displacement pump is one which will draw in the same volume independent of whether that volume is drawn as liquid or gas. The necessity for such can be seen from the explanation of the various functions above. Note in particular the pipetters where the pumping system is filled with air except for the small amount of liquid in the pipetter tip and the transfer system which must accurately move alternating slugs of air and liquid. Thus, in addition to piston and cylinder type pumps, peristaltic pumps or other types of positive displacement pumps can be used in the apparatus of the present invention.

AUXILIARY SYSTEMS

Figure 26:
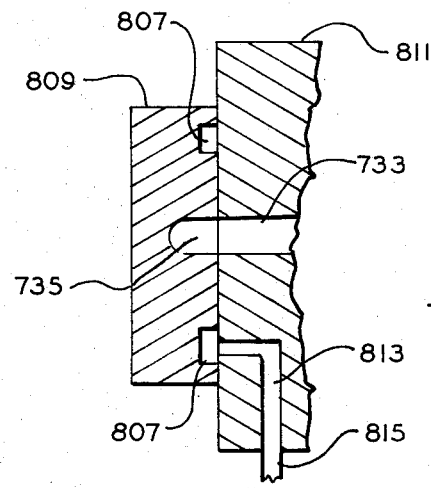
FIG. 26 is a partial cross-sectional view illustrating the manner in which the slide valves of FIGS. 23 and 24 are lubricated.

The slide valves described above in connection with FIGS. 23 and 24 contain a groove between their outside surfaces and their inside connecting passages for sealing purposes. These grooves 807, in evidence on FIG. 24, appear in greater clarity in a view of one of the valves constituting FIG. 26. Groove 807 extends all the way around the valve member and may be rectangular, circular and so on. It is only necessary that a groove be interposed between the edges 809 of the valve member and the internal connecting passage, such as the passage 735. Within the block 811, a passage 813 is formed terminating with a nipple 815. Sealant liquid under a slight pressure is supplied to the nipple 815 and fills the groove 807. This ensures a liquid seal and also results in lubrication for the valve.

Figure 27:
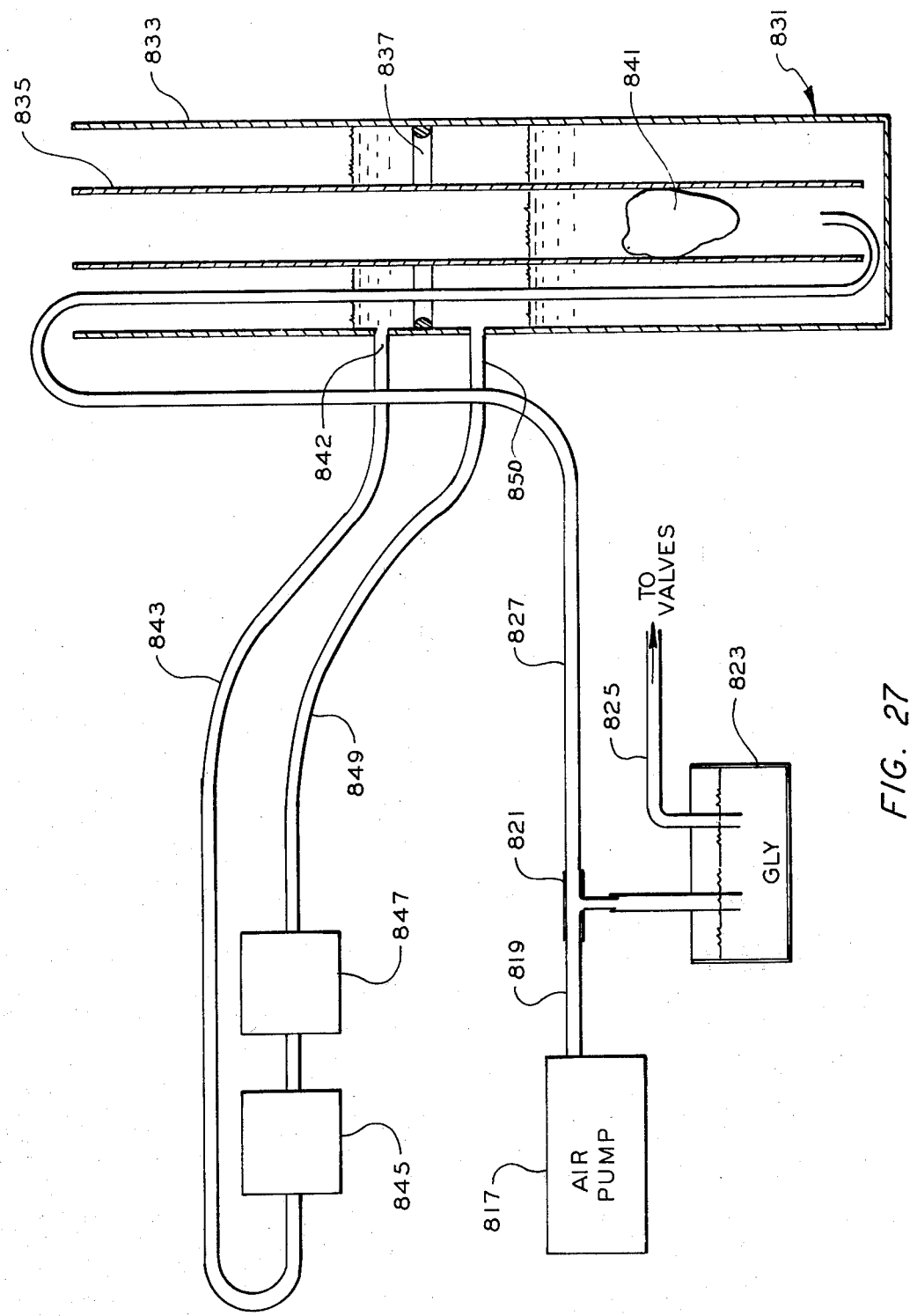
FIG. 27 is a schematic representation of the pressurizing system for the sealant liquid in the slide valve of FIG. 26 and shows how the same system is used to supply cooling water to heat pumps.

The manner in which this sealant liquid is supplied under pressure is shown on FIG. 27. A bellows type air pump 817 driven by an appropriate cam on a motor shaft provides an output of air under pressure. The output of air pump 817 is provided on a line 819 to one leg of a T connection 821, another leg of which is flow-coupled into a sealed container 823 containing sealant liquid. A line 825 is inserted into the sealant liquid and its output provided to the valve grooves. The remaining leg of the T is coupled by line 827 to a water column pressure regulator 831. Here the air from pump 817 is caused to bubble up through an appropriate column of water and thus maintains the pressure in the line 819 at the desired level to force the sealant liquid to the valve grooves.

Any number of different liquids may be used as the sealant. In cases where extremely small quantities will not interfere with the reactions and analyses being carried out, glycerine works well as a sealant liquid. However, for some of the reactions carried out by the instrument of the present invention, even the extremely small quantities of glycerine which leak from the seal into the system can cause difficulties. For that reason, water may be used as the sealant liquid. Surprisingly, it has been found that water when used for this purpose works almost as well as glycerine.

The pressure regulator 831 serves a second purpose. It is also used to supply coolant to the heat exchangers associated with the photometer cell and with the log amplifiers both previously described. The pressure regulator comprises an outer cylindrical container 833 and an inner cylindrical tube 835, the latter 835 containing cut-outs in the bottom so that the level of water inside it will be the same as the level of water in the outer container 833. A septum 837 is provided separating outer container 833 into two sections. Bubbles, represented at 841, forming within the tube 835, cause water to be forced out at the top and spill over into outer container 833 in the area above the septum 837. An outlet 842 at this point is connected with a tube 843 leading to heat exchangers 845 and 847. Thus, as water is forced into the top portion of the pressure regulator, it flows out under the force of gravity to heat exchangers 845 and 847 which are positioned to be at a level below the level of the outlet 842. The water, then returns through a tube 849 to an inlet 850 and back into the bottom portion of the container 833.

As described in connection with FIG. 1, at various places, pipetters or probes are passed through sponges 39 in plastic containers used for the purpose of wiping off any drops of liquid thereon to maintain accuracy in the system. To insure proper operation of this portion of the system, the water used in the sponges must be constantly circulated, i.e., the water which has become contaminated with reagent or sample must be removed and clean water provided. In principle, this is done by supplying water under pressure to the sponges and removing water therefrom with a vacuum. However, it will be recognized that an ideal system will not be obtained if the various sponges are all just connected together to a pressure source and vacuum source. If such is attempted, the sponge closest or the one having the least resistance will get all the circulation whereas no circulation will occur through the others. Thus, it is necessary that the sponges be individually irrigated in sequence in order to insure that each has adequate change of liquid. The general arrangement of this system is shown on FIG. 28. Each of the sponge holders 851 is a plastic case having two ports formed therein. Enclosed within the plastic case is a sponge 39. One line from each of the sponge holders 851, i.e., the lines designated 853$a$ through $d$ is provided to a water pump and distributor arrangement. The other lines, designated 855$a$ through 855$d$, are provided to a vacuum distributor 857, the outlet of which is coupled through a valve 859 to a vacuum pump 861. A motor 863 has on its shaft cams 865, 866 and 867. The cam 865 drives the air pump 817 (FIG. 27) described above. The cam 866 drives the vacuum pump and the cam 867 drives the valve 859. The motor shaft is coupled through a two to one reduction to the water pump and distributor 858 and through an additional four to one reduction to the vacuum distributor 857. In the preferred embodiment, this is done using belts and pulleys. The water pump and distributor to be described in more detail below sequentially pumps out water drawn from a water supply to the lines 853$a$, $b$, $c$ and $d$ to supply equal amounts of water to the sponge holders 85. Similarly, the vacuum pump sequentially, through rotation of the distributor 857, draws on each of the lines 855$a$ through $d$ to draw out contaminated water. During the cycle in which the vacuum pump is drawing the vacuum, the valve 859 couples the vacuum pump to the distributor 857. Water is drawn into the line between the valve and the vacuum pump. As the vacuum pump expels, the valve couples the vacuum pump to the line 869 connected to a waste discharge, thereby forcing out the water drawn in during the vacuum cycle.

Figure 28:
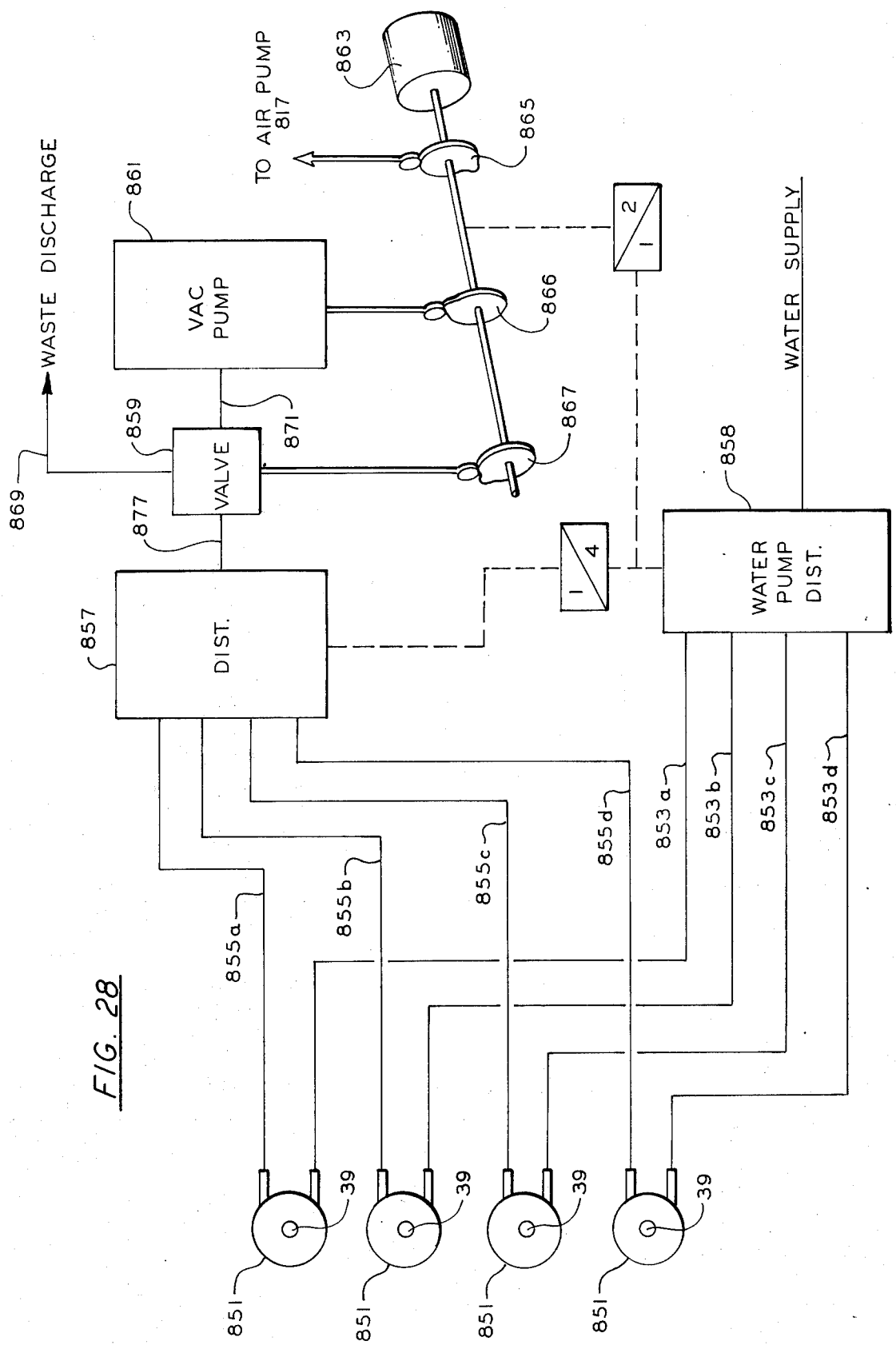
FIG. 28 is a block diagram illustrating sponge irrigation for the sponges of FIG. 1.
Figure 29:
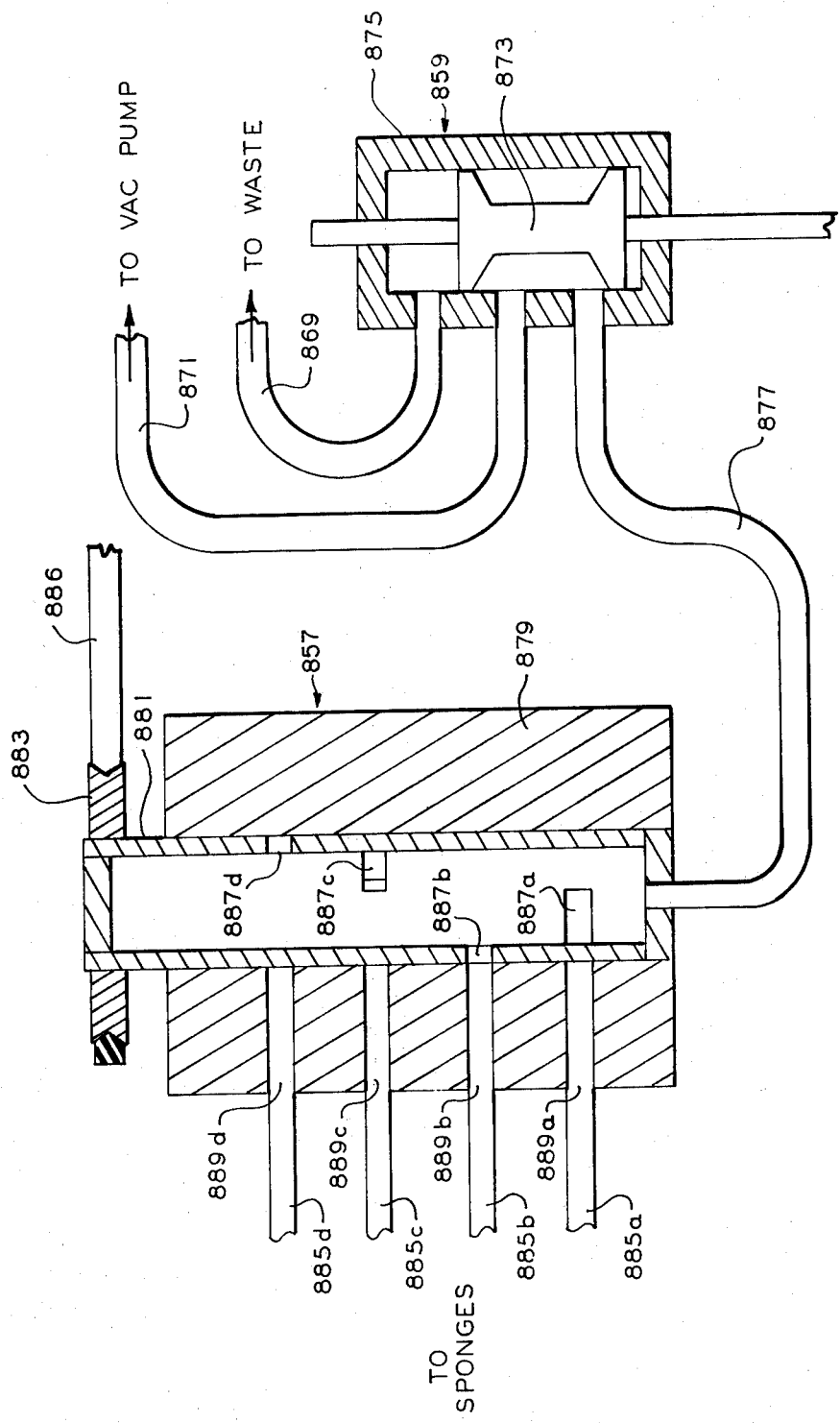
FIG. 29 is a sectional view illustrating the vacuum distributor of FIG. 28.

FIG. 29 illustrates the distributor (857) and the valve (859) arrangement in greater detail. In the position shown, the line 871 between the valve 859 and the vacuum pump is coupled by the position of valve spindle 873 to the outlet line 877 which is connected to the distributor 857. The distributor comprises an outer casing 879 with a cylindrical cavity therein in which a cylindrical valving member 881 can rotate. On top of member 881 is a pulley 883 driven by a belt 886 connected to the motor 863 or connected to the water pump and distributor 858 of FIG. 28. Valving member 881 contains a plurality of four openings designated 887a, b, c and d. When properly positioned, they register with corresponding ports 889a through d to sequentially connect the vacuum line 877 to each of the lines 855a through d so that each of the sponges is drawn on equally. After a suction stroke of the vacuum pump, the valve spindle 873 is moved upwardly to couple the lines 869 and 871. Now, as the vacuum pump expels, water drawn into the line 871 during the vacuum cycle is discharged through the lines 869 to waste.

Figure 30:
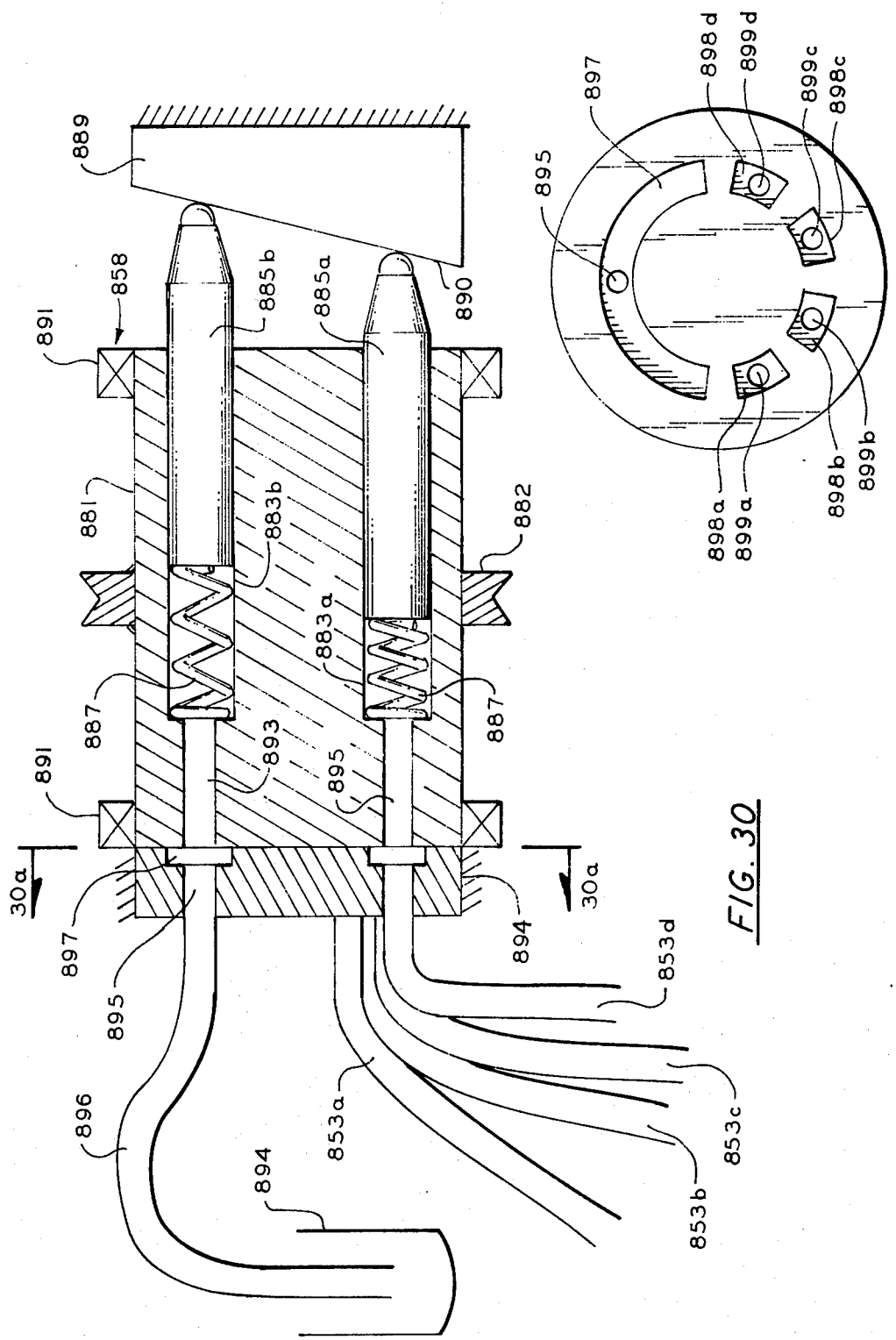
FIG. 30 is a sectional view illustrating the water pump of FIG. 28.

The water pump and distributor 858 of FIG. 28 is shown on FIG. 30. The pump comprises a cylindrical block 881 in which two cylinder bores 883a and 883b are formed. Generally, cylindrical piston members 885a and 885b are slidably fitted in the bores. Springs 887 in cylinders 883a and b urge pistons 885a and b out of the cylinders so that the outer ends of the pistons, carrying bearing balls for the purposes, abut an inclined surface 890 of a fixed "wobble" (or "swash") plate 889, the surface being a skew plane with respect to the axis of cylindrical block 881. The cylinder 881 is supported for rotation about its axis in conventional bearing means 891. Ports 893 and 895 in block 881 extend from the head end of cylinder bores 883a and 883b respectively to the proximal end face of the block on which is fixed distributor plate 894. A plan view of the inside of distributor plate 894 is shown on FIG. 30a. It includes an inlet port 895 which opens into an arcuate channel 897 extending approximately 180° of the plate. Disposed on an arc concentric and of equal radius to channel 897 are four additional channels 898a through d, equiangularly spaced and jointly defining an arc of approximately 180°. Opening into each arcuate channel 898a through 898d is a respective port 899 a–d. Reverting to FIG. 30, the port 895 is coupled to a line 896 leading to a water container 894. The ports 899a through d are coupled respectively to the lines 853a through 853d shown on FIG. 28. As the cylinder block 881 rotates, one of the pistons 885a,b, say 885b, during the portion of the cycle when the port 893 is in communication with the channel 897, will retract drawing water into the associated cylinder from the container 894. During the remainder of its cycle, it will then sequentially pump water out of each of the ports 899a through d by pumping water to their associated channels 898a through d as it travels over that sector of the distributor plate. While the piston 885b is drawing water in, the piston 885a will be pumping water out in the same manner.

MECHANICAL DRIVES

FIG. 31 is a fragmentary plan view of the instrument shown in FIG. 1 illustrating the physical location of various mechanical elements. At the input parking lot 53 a pair of belts 1001 are provided, contacting the bottom of the magazines 47 on each side so that when a magazine is placed in the input parking lot area, it will be driven (broadside) toward the preparation area. The belt drives and other drives will be described in more detail below with FIG. 31 being used primarily to give an overview of the location of the various mechanical elements. The motor drive for the belts 1001 is shown in dotted lines and designated 1003. Stepping of a magazine 47 (longitudinally) through the preparation area is carried out by a stepper drive, the motor 1005 of which is shown in dotted lines. Broadside movement through the pre-incubator area 61 after a cartridge has been moved into position therein is accomplished by a belt drive having belts 1007 similar to belt 1001. The drive motor 1009 for the belts 1007 is shown in dotted lines at the left-hand rear corner of area 61. Similarly, a first stepper 1011 for moving cartridges longitudinally through the analyzer area is shown at the right rear corner of area 61. The analyzer area contains a second stepper 1013 shown in dotted lines for stepping the cartridges longitudinally out of the analyzer area into a position where they can be moved (broadside) to the output parking lot 81 by a bailer 1015 driven by a motor 1017.

Also shown is the sample platter 15 which is rotated in a step-wise manner. The positioning of the diluter, the first and second pipetters and the stirrer is also illustrated on FIG. 31. The diluter probe 23 rotates about the axis 1019 so that it can be positioned either over a sample cup in platter 15 or a reaction cup in the magazine 47. The first pipetter arm 35 rotates about an axis 1021 from a position about first reagent bottle 27 situated in a well 1023 to a position over a reaction cup in the magazine 47. Similarly, the second pipetter arm 37 rotates about an axis 1025 from the position shown over second reagent bottle 29 to a position over a cup in the analyzer section. Reagent bottle 29 is also retained within a well 1027 similar to well 1023. The stirrer arm 45 rotates about an axis 1029 between a well 1031 containing a wash liquid and a position over a reaction cup in the magazine in the analyzer section where it stirs the reaction mixture as described above. FIG. 32 is a cross-sectional view taken along the lines 32, 32 of FIG. 31 illustrating the diluter mechanism. FIG. 33 is a partial sectional plan view of FIG. 32 and FIG. 34 a view of a portion of the mechanism inside the diluter of FIG. 32. The diluter probe 21 to which the tube 25, discussed above in connection with FIG. 1, is attached, is supported by the arm 23. Arm 23 is attached using a screw connection to a shaft 1031 extending from inside the apparatus. The shaft 1031 is supported in two bearings 1033 and 1035 which are free to rotate with respect to the shaft 1031. The other end of the shaft 1031 is secured with a set screw 1037 to a radially projecting boss on an otherwise generally cylindrical member 1039 having a central bore containing a bushing 1041 and rotably mounting member 1039 on a rod 1043. Concentrically surrounding the rod 1043 is a fixed outer cam member 1045 of cylindrical shape containing a slot 1047 therein forming its cam surfaces engaged by bearing 1035. A portion of slot 1047 is shown in FIG. 32; substantially the entire slot appears in FIG. 35. Located concentrically within the cam member 1045 is an inner cylindrical cam member 1049, having a cut-out portion 1051 which defines a camming surface, better shown in FIG. 35, for bearing 1039. The camming surfaces will be described in greater detail presently in connection with FIGS. 35 and 36.

Member 1039 is biased in an upward direction by a spring and pulley arrangement indicated generally as 1053 and including a bottom member 1055 mounted to the shaft 1043, a top member 1057 in contact with the bushing 1041 of member 1039 at the top of the shaft 1043 and side members 1059 and 1061 shown on FIG. 34. As illustrated on the figure, the side pieces and top and bottom pieces are assembled in a conventional manner using screws. Located between the sides 1061 and 1059 are two double pulleys 1063 and 1065. Pulley 1063 is mounted on an axle 1067 passing through the sides 1059 and 1061 and is thus fixed with respect thereto. Pulley 1065 is supported within a bracket 1069 having attached to it one end of a spring 1071 which has its other end affixed to the bottom member 1055. As best appears in FIG. 32, a cable 1073 is attached to the top member 1057, runs over bottom pulley 1065, then over one side of top pulley 1063, then over the other side of bottom pulley 1065 and the other side of top pulley 1063 and finally is attached to the member 1039 at a point 1975. Spring 1071 urges pulley 1065 downward which, in turn, causes a lengthening of the amount of cable 1073 between the two pulleys resulting in the member 1039 being urged upwardly. Thus, the member 1039 and, concomitantly, arm 23 and probe 21 are biased upwardly against the cam surfaces.

The inner cam member 1051 is rotatable and the outer cam member 1045 fixed. Shaft 1043 is mounted in suitable bearing means at the top and bottom of outer member cam 1045 and is free to rotate therein. A motor 1077, through a coupling 1079, drives gear 1081 meshing with a gear 1083 attached to the shaft 1043 causing rotation thereof. However, since the member 1039 is free to rotate on shaft 1043 as is the inner cam member 1049, no further rotation takes place due simply to rotation of shaft 1043. However, a spring 1083 is provided pressing the bottom of inner cam member 1049 downwardly against a fiber clutch member 1085, so that the rotation of the gear 1084 is transmitted to the inner cam member 1049 resulting in its rotation. The manner in which rotation of the inner cam with respect to the outer cam causes the desired probe movements will be explained below in connection with FIGS. 35 and 36. However, one additional item shown on FIG. 32 should be noted. Mounted within, and at the bottom of, inner cam member 1049 is a retro-reflector 1091 of the type already described. Reflector 1091 is aligned with an aperture 1093 in inner cam member which registers with an aperture 1095 in the outer cam member 1045 when the cam members are at the starting position. Thus, when the required sequence of events has taken place, light directed along a path 1097 by a dual-optical angle sensor 80 of the type already described can be used to stop the diluter sequence.

FIG. 35 is an exploded view showing cam members 1045 and 1049, probe 21, probe arm 23 and bearings 1033 and 1035. As noted above, outer cam member 1045 is fixed and inner cam member 1049 is rotatable by motor 1077 through gears 1081 and 1083 and the friction clutch 1085 as described above. FIG. 36 is a developed view of inner cam member 1049. In the position illustrated by FIG. 35, the bearing 1033 will be resting on cam surface 1051 at point 1101. The bearing 1035 will be riding in the horizonal portion 1103 of the cam slot 1047 in the fixed cam member 1045. The bottom horizontal surface prevents movement up and down and thus between the points 1105 and 1107 the probe 21 will rotate as the inner cam member 1049 is rotated. Consider first what would occur if the inner cam 1049 were rotated in the direction of arror 1109. The arm 23 and probe 21 with it will rotate over to point 1107. As rotation of the cam continues, the probe arm 23 will be pushed downward by the inner cam surface 1111 moving down in the verticle slot 1113 of the outer cam member until it reaches the bottom. At that point, bearing 1033 will be resting on the flat surface 1115 of the inner cam member. This corresponds to the position where the probe 21 is in the reaction cup in the magazine. Rotation of the inner cam member in the direction of arrow 1109 from the position just described will result in the bearing 1033 being guided by the surfaces 1115 and 1111 up to the cam surface to point 1101 whereupon the arm 23 will be caused to rotate to the point 1105 of the outer cam surface. At that point, the cam surface portion 1119 of the inner cam will press on bearing 1033 causing it to move downward in the slot 1121 of the outer cam member. It will move down in a linear fashion along the surface 1119 and then move slowly as it reaches the surface 1123 on inner cam member 1049 until finally it reaches the flat portion 1125 at which point, it will be at the bottom of the slot 1121 and positioned in a cup on the serum sample platter at the front of the machine. Inner cam surfaces 1123 and 1111 are both parabolic to minimize acceleration at the points where the probe tip is moved into and out of the liquid either in the platter cup or the magazine cup. Otherwise, large accelerations could cause inaccuracies in the metering of the material picked up and discharged by the probe.

Figure 37:
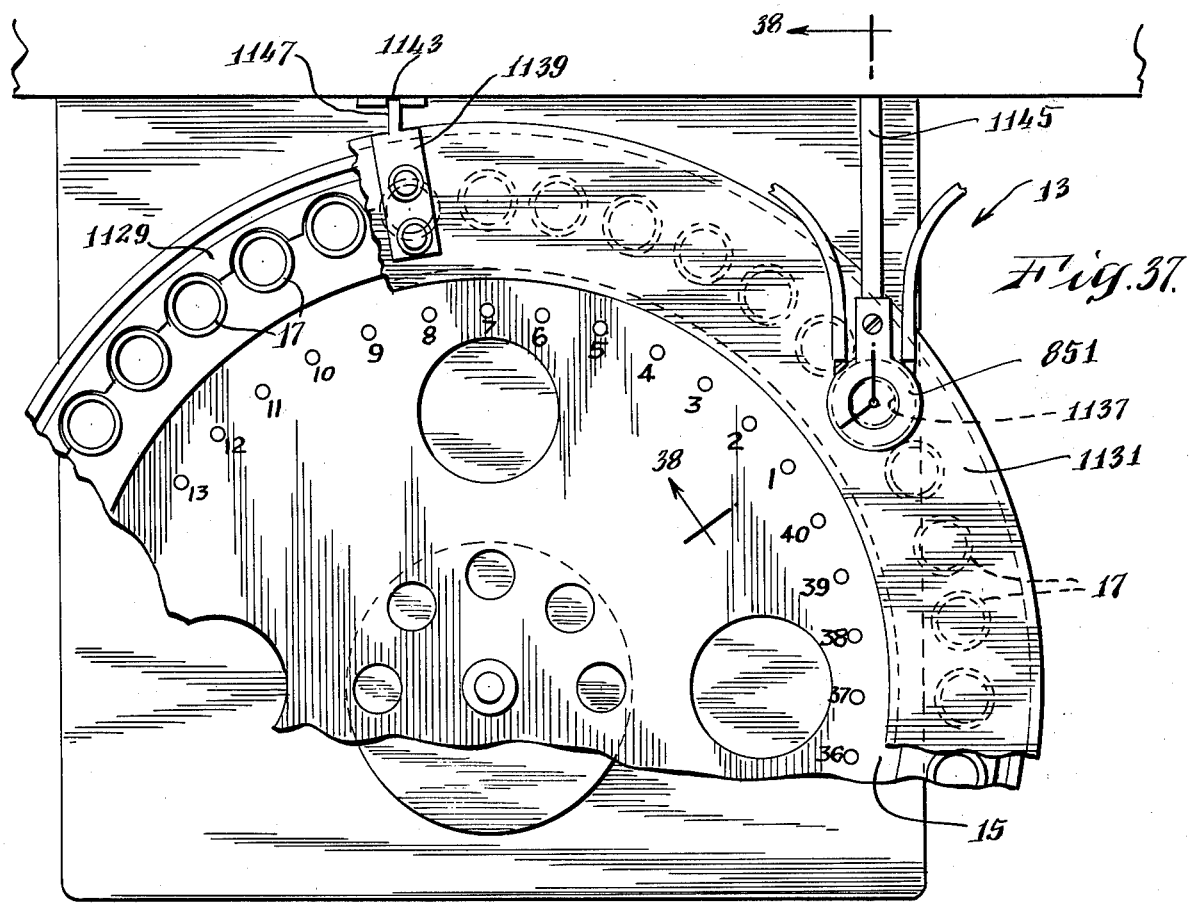
FIG. 37 is a plan view partially cut away of the sample platter of the analyzer of FIG. 1.
Figure 38:
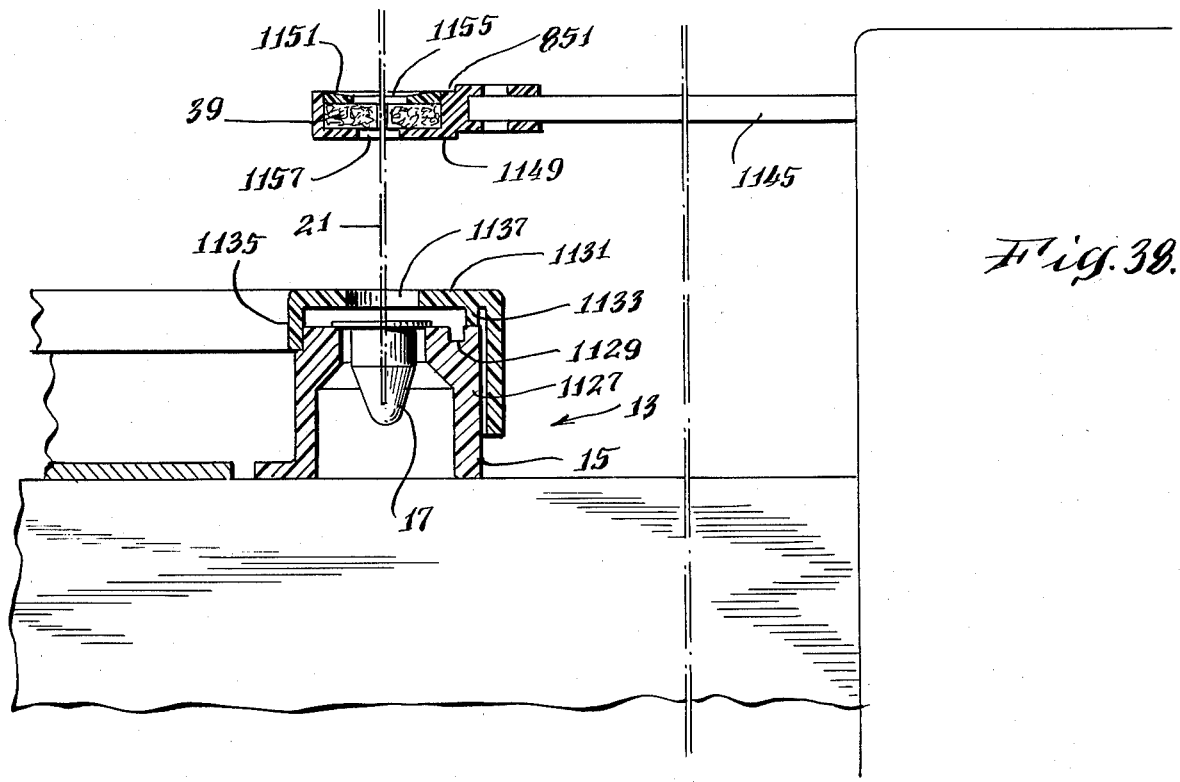
FIG. 38 is a section on line 38—38 of FIG. 37 illustrating the sample platter and a typical sponge wiper in cross section.

FIG. 37 is a plan view, partially cut away, of the sample platter and FIG. 38 is a cross-section through a portion thereof. The sample platter 15 is a circular member having an annular lip 1127 at its outside in which are formed a plurality of equiangularly spaced holes capable of receiving sample cups 17. The annular lip 1127 has in its upper surface a circumferential channel 1129 which may be filled with water. An annular cover 1131 is placed over the lip portion 1127 of platter 15. Cover 1131 has inner and outer circumferential projections 1133 and 1135 extending downward and resting on appropriate portions of the platter 15. Only a single opening 1137, aligned with the sponge 39, is provided in the cover 1131. The cover remains stationary while the platter 15 is rotated below it. To prevent the rotation of the cover 1131 with platter 15, a stop comprising a member 1139, having a projection 1147 engaging a slot 1143 formed on the front of the apparatus, is attached to the cover. By filling the channel 1129 with water and using the cover 1131 with only the single opening, a high level of humidity is maintained above the samples in the cups 15 and as a result, evaporation does not take place to cause changes in the sample concentration.

Also shown on FIGS. 37 and 38 is the sponge arrangement. As illustrated, an appropriate bracket 1145 supports a plastic sponge holder 851 which is preferably made of a base member 1149 and a snap-in cover 1151. The sponge holder is essentially cylindrical and has a space inside in which the sponge 39 is inserted. Aligned central apertures 1155 and 1157 in base 1149 and cover 1151 enable penetration by probe 21. The sponge 39 is arranged within the casing so that it is in contact with the probe on all sides as the probe passes through the sponge on its way to and from the cup 17. Wiping by the sponge in this manner both here and in the pipetters ensures a predictable type of drop on the end of the probe tip thereby insuring the accuracy and repeatability of the apparatus. Without good sponge wiping, drops of different sizes can form on the tip end and result in different quantities of serum sample or reagent being deposited in the magazine cup. This, in turn, can cause inaccurate results. Because of the extremely small quantities being used in the apparatus of the present invention even the slight difference in the size of the drop at the end of the tip can cause inaccurate results if this measure is not taken. The sponge holder 851 is also provided with inlet and outlet passages as described above in connection with FIG. 28 which allows constant irrigation of the sponge to be carried out to avoid contamination of the probe.

FIGS. 39-42 illustrate the mechanisms used for moving the magazine through the apparatus. FIG. 39 is a sectional view taken along the section 39—39 of FIG. 31. It illustrates the belt drive in the preincubator area 61 as well as the steppers for moving magazines through the analyzer section of the apparatus and out to the output parking lot 81. The belt drive at the input parking lot 53 is essentially the same. FIG. 40 shows the belt drive in a fragmentary elevational view partially in section taken at the input parking lot. As shown on FIG. 39, the motor 1009 of FIG. 31 is coupled to a shaft 1161 having thereon cylindrical members for engaging the belts 1007 and 1101. As can be seen from FIG. 40, the shaft 1161 is located below the input parking area, or preincubator area as the case may be, and the belt 1007 or 1101 taken over to idlers 1163 and 1165. Between the idlers 1163 and 1165, the belts travel horizontally carrying with them the magazines 47. The belts 1107 are effective to drive the magazines only to the point 1167. Shown on FIG. 39 is the gate 1169 referred to above. When it is not desired to move a magazine into the analyzer area, this gate is moved upward to act as a stop. In addition, there is provided both at the input parking lot, for moving the magazine into the preparation position, and at the preincubator, for moving the magazine into the analyzer area, a mechanism for moving magazines into those respective positions. Motor 1009 is constantly rotating when the apparatus is in operation to move the magazines up to the position where they are ready to be moved into the preparation or analyzer area. Once magazines back up as shown on FIG. 40, the belt will slip beneath them. Horizontal step-wise movement through the preparation unit and analyzer is accomplished through the use of steppers. The first stepper in the analyzer area is driven by the motor 1011. As illustrated by FIG. 39 and also by FIGS. 41 and 42, the stepper comprises a cylindrical member 1171 having three equally spaced projections 1173 on its top. Cylindrical member 1171 is supported for rotation in the frame of the apparatus with the projections 1173 projecting above the surface on which the magazine 47 rests to engage appropriate parts thereof. When it is desired to step a magazine ahead one cup space, the member 1171 is rotated by its associated motor and a projection 1173 engages a cut-out 1175 in the base of the magazine moving it one step ahead. Three projections 1173 are provided on the member 1171 so that a step of one cup spacing requires only ⅓ revolution of the motor and member 1171. As noted above, three reflectors are installed on the motor to control these partial revolutions. A second set of steppers comprising the steppers 1177 and 1013 are also provided in the analyzer area. These steppers are driven by motor 1179 having an output shaft 1181 coupled directly to the stepper 1177. Stepper 1177 includes a pulley 1183 coupled to a similar pulley 1185 on the stepper 1013 through a belt 1187. A tension arm (obscured by belt 1187) carries pulley 1189 and is pivoted on a member 1191. The tensions pulley 1189 maintains tension on the belt 1187 so that the steppers 1177 and 1013 rotate together.

When the magazine 47 has been stepped all the way through the analyzer area, it comes to rest aligned with the output parking lot 81 of FIG. 31. Motor 1017 is then operated to cause the bailer 1015 to push the magazine broadside out into the output parking lot. A similar mechanism is provided to push the magazine from the preparation area into the preincubator area. As shown, the bailer 1015 simply comprises an appropriately shaped bracket which is coupled to the motor 1017 through a linkage 1093. The drives for moving the magazines into the preparation and analyzer area are slightly different having, instead of a bailer mechanism, a pair of fingers which rotate and engage the magazine.

FIG. 41 also shows some details of the magazine construction. The reaction cups 55 are held within appropriate cylindrical cavities in the magazine 47 by a plurality of spring fingers 1195 arranged around the circumference of the opening at the top on a diameter slightly smaller than the outer diameter of the reaction cup. Typically, three such fingers 1195 with spaces therebetween are provided and the magazine is of molded plastic so that the fingers will be molded to have a intrinsic springiness. Insertion of the cup 55 into the cylindrical cavity will result in the fingers 1195 pressing against it holding it tightly in place.

Figure 43:
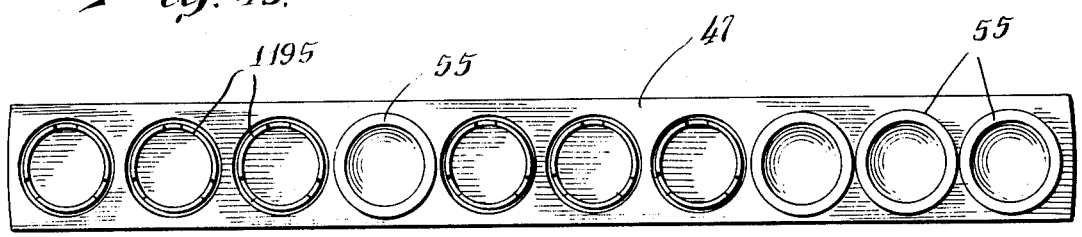
FIG. 43 is a top plan view of a magazine used in the analyzer of FIG. 1.
Figure 44:
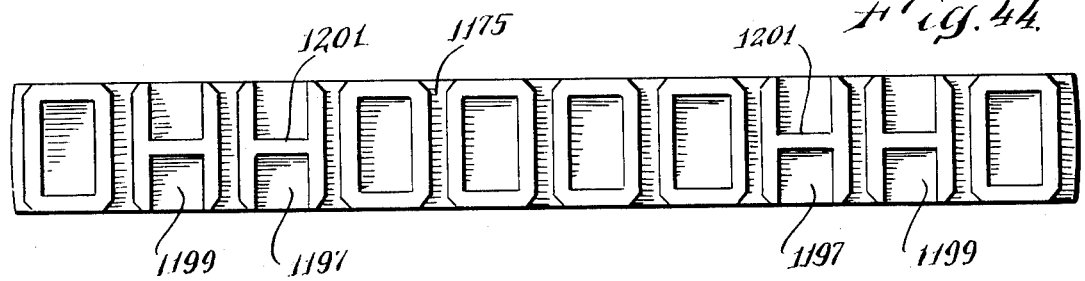
FIG. 44 is a bottom plan view of the magazine shown in FIG. 43.
Figure 45:
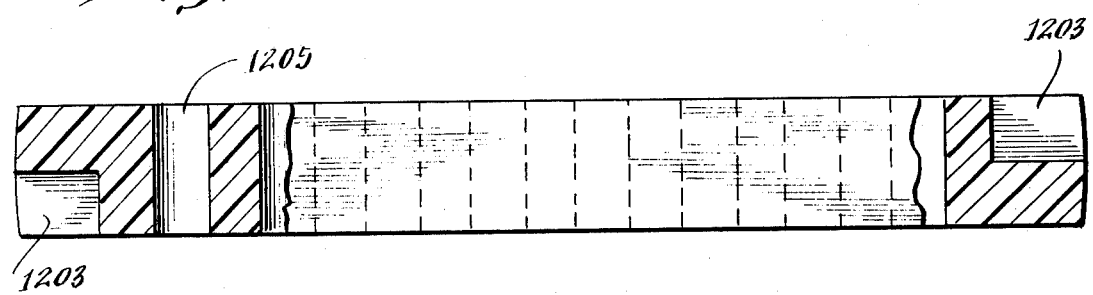
FIG. 45 is a plan view of a spacer magazine used for separating different tests in the analyzer of FIG. 1.

Further details of magazine construction are shown on FIGS. 43-47. FIG. 43 shows a tip plan view of the magazine 47 and, with the applied reference numerals, is self-explanatory. FIG. 44 shows a bottom plan view of the magazine. Shown are the cut-outs 1175 which are engaged by the stepper projecions 1173 as described above. Also shown are cut-outs 1197 and 1199. The cut-outs 1199 engage the gate 1169 described above in connection with FIG. 39 to prevent movement of the magazine into the analyzer area when the gate is closed. The cut-outs 1199 are placed so that the means for moving the magazine into the analyzer area and preparation area will engage the surfaces 1201 to push the magazines into place. FIG. 45 is a top plan view of a spacer magazine. As explained above, spacer magazines may be used between tests to suspend operations while the operator changes reagents. As also noted above, functional decisions are made by sensing the presence or absence of a magazine or cup. With reference to FIG. 9, it can be seen that the magazine sensor at sensor position SS 36 looks across the corner of the magazine to determine its presence. In order to provide an indication of "no magazine" at that point but an indication of a magazine at the sensing position SS 7 which looks across another corner of the magazine, the spacer magazine is shaped as shown on FIGS. 45, 46 and 47, that is, a cut-out 1203 is made on each end of the magazine. If this magazine is now in the preparation position on FIG. 9, it can be seen that the sensor SS 36 will indicate the presence of a magazine but the sensor SS 7 will indicate that no magazine is present. This condition can be used to stop the preparation unit until the reagent is changed. In the analyzer area, sensing of cups is carried out by sensors such as the sensors SS 1 and SS 3. To sense the presence of a spacer magazine in the analyzer area, an indication of the absence of a cup is used. Thus, the spacer magazine has a horizontal through bore 1205 at each cup position. When the analyzer unit encounters such a magazine, it will stop its processing and close the gate as described above.

FIGS. 48-51 illustrate the apparatus used for obtaining the required pipetter motion. As was described above, the pipetter must have the capability of moving up and down at both ends of its rotation between the reagent bottle and the reaction cups in the magazine. This combined rotation and up and down movement is accomplished through the use of a butterfly cam. Both the "first" and "second" pipetters are identical except for direction of rotation and thus the following discussion applies to both. FIG. 48 is an elevational view partially in cross-section of the first pipetter arrangement. The reagent bottle 27 is contained within a well 1023. A sponge arrangement 39 identical to that described above in connection with FIG. 38 is provided. In the manner described above, the pipette 31 is wiped as it passes through this sponge. The pipette 31 is supported on arm 35 shown in more detail on FIG. 49. The arm 35 contains a flat recess 1213 adjacent its free end and at the very end has a slotted portion 1215 to permit insertion of the removable pipette 31. The pipette is held in place by a spring-loaded rubber grommet 1217. The grommet 1217 has a portion passing through a suitably apertured lever 1219. The bottom port 1221 of the grommet rests against the top of the pipette 31 sealing it in place. The flexible tube 57 is inserted into the top part 1223 of the grommet 1217 down to the level shown in dotted lines. A spring 1225 is provided to bias the lever 1219 upward at its righthand side. This causes the member 1219 which rotates about a pivot point 1227 to exert a downward pressure on the grommet 1217 pushing its bottom 1221 against the pipette 31 holding it in place and sealing it.

The arm 1211 is bolted, using bolts 1229, to a member 1231 essentially cylindrical in shape. Member 1231 has a cylindrical recess 1233 therein into which is inserted a hollow cylindrical member 1235. These two members 1235 and 1231 are in a press fit with each other acting as a single unit. Inside the cylindrical member 1235 is a rod 1237 which is fixed to the base of the apparatus. The member 1235 and with it the member 1231 are free to rotate about the rod 1237. The member 1235 terminates at its base with a larger cylindrical portion having a slanted cut thereon mating with a cylindrical projection 1239 on the butterfly cam 1241 as shown on FIG. 50. The butterfly cam is also free to rotate about and move up and down on the rod 1237. It can be seen that motion of the butterfly cam 1241 up and down and rotationally about the rod 1237 will result in corresponding motion of the arm 1211 and pipette 31. The slanted coupling between the members 1235 and 1239 permits manually raising and rotating the arm 1211 without engagement with the butterfly cam 1241 for maintenance purposes. It also eases the positioning of the arm 1211 for changing pipette tips 31.

Figure 51:
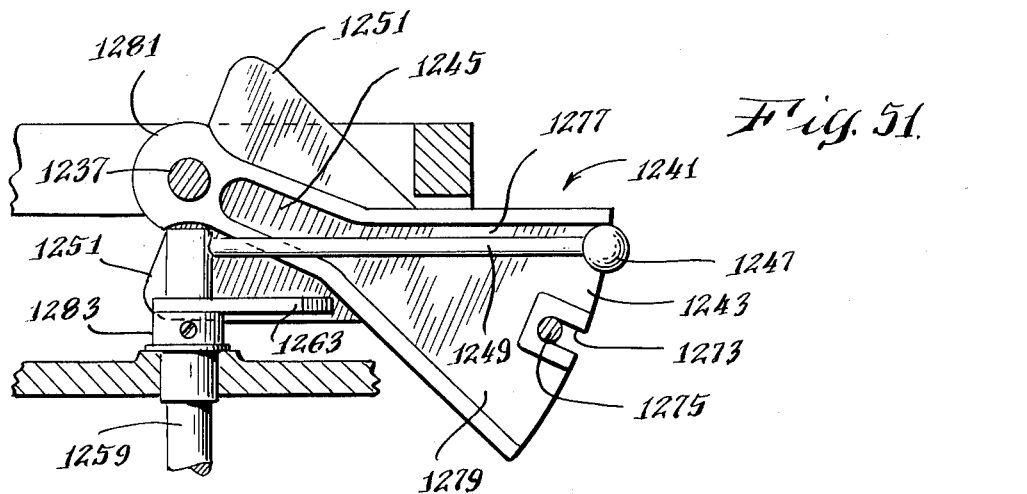
FIG. 51 is a view of the butterfly cam of FIG. 48 and 50 looking in the direction of the arrows at line 51—51 of FIG. 50.

Details of construction of butterfly cam 1241 are shown on FIG. 51, a plan view of its underside. As can be seen from that figure and also with reference to FIG. 48, cam 1241 contains in its underside a recess 1243. This recess includes a divergent portion narrowing to a channel portion 1245. Motion of the butterfly cam 1241 is obtained by movement of a ball 1247 on the end of a rod 1249. The butterfly 1241 also contains projections 1251 on each side the purpose of which will become evident below. The rod 1249 with the ball 1247 on the end is driven by a motor 1253, shown on FIG. 48, through gears 1255 and 1257. The rod 1249 is affixed to a shaft 1259 which which is attached to the gear 1257. Shaft 1259 is supported in conventional bearing means for rotation about the axis 1261 shown on FIG. 50. Also attached to the shaft 1259 is a cam 1263. This cam 1263 engages the projections 1251 in a manner to be described below. Further mounted on the shaft 125 is a retro-reflector 1265 which is used for stopping the cycle in the manner described above. Appropriate holes 1267 are made through the base 1269 of the apparatus so that a lens 1271 such as that described above can be directed at the reflector 1265. the butterfly 1241 also contains cut-out 1273 in its end which in a lower position engages a pin 1275 used for smoothly guiding the butterfly as it is lowered.

The manner in which the apparatus operates may best be understood by going through a cycle of operations. In the positions shown on the figures, the ball 1247 is just starting to move the butterfly 1241. As the rod 1249 is rotated counterclockwise, it will ride within the recess 1243 against the edge 1277 of the butterfly raising the butterfly upward and with it the arm 1211 and pipette 31. When the rod 1249 gets to the position 1245, it will cause rotation of the butterfly 1241 about the rod 1237 resulting in rotation of the arm 1211 and pipette 31. Rotation will continue over an angle determined by the length of the channel 1245 with the ball, at a point half way through the angle beginning motion down the side 1279 of the butterfly. As it gets to the angled portion of that side, the butterfly will begin to be lowered. The ball will move along the edge 1279 lowering the butterfly and with it the arm 1211 and pipette 31. As it gets down to the position shown on FIG. 50, (it will be in this position but on the other side having been rotated), it will engage the pin 1275 for guidance purposes. At some point, the ball will lose contact with the butterfly, the base 1281 of the butterfly then resting on the cam 1263. The cam 1263 will then control the lowering of the pipette the rest of the way down into contact with the liquid in the reagent bottle or into the cup. The cam surface of cam 1263, in particular the surface 1283, causes this final lowering into the desired position by riding on the projections 1251 on one side or the other. For rotation back to the position shown, the opposite chain of events takes place. The arm 1249 and cam 1273 rotate clockwise, the cam 1273 first pushing the butterfly 1241 upward until the ball 1247 engages the butterfly with the ball then pushing it upward to the position shown in dotted lines after which it rotates the butterfly and then lowers it back onto the cam 1263.

Figure 53:
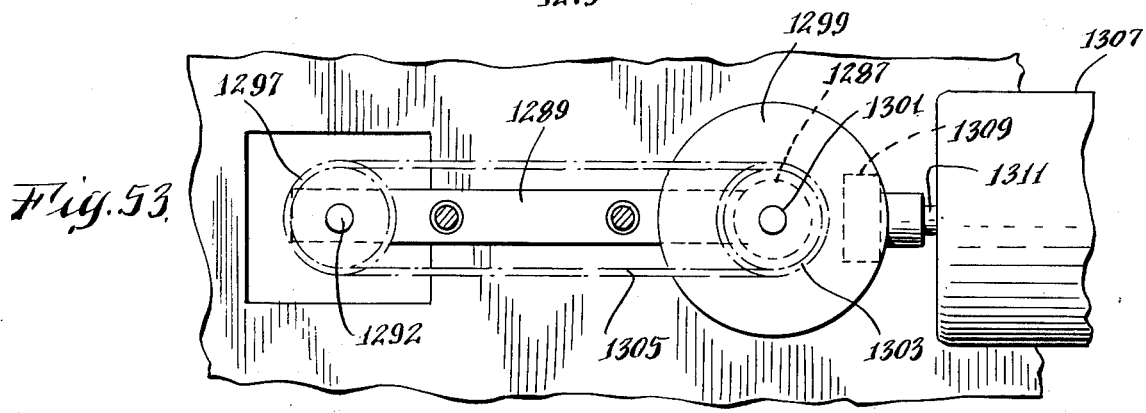
FIG. 53 is a sectional view taken along the line 53—53 of the stirrer of FIG. 52 looking in the direction of the arrows.
Figure 52:
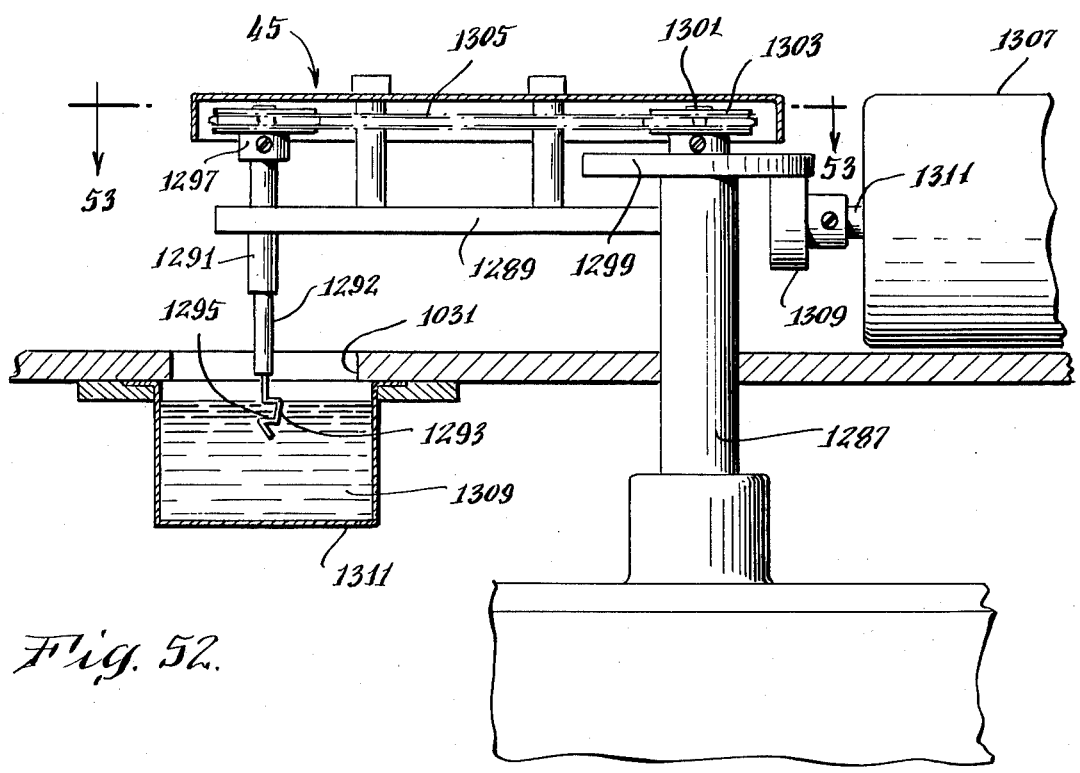
FIG. 52 is a sectional view taken along line 52—52 of FIG. 31 illustrating the stirrer of the apparatus of FIG. 1.

FIGS. 52 and 53 illustrate the stirrer. The mechanism which raises and lowers and rotates the stirrer between one position and the other is identical to that described above in connection with the pipetters and thus will not be shown in detail. The up and down and rotational movement of the shaft 1287 of FIG. 52 takes place in the same mamner described in connection with these previous figures. Extending from the shaft and solidly affixed thereto, is a bracket 1289. At its end, the bracket 1289 has a bushing 1291 inserted therein through which a shaft 1292 is inserted on the end of which is the stirrer 1293. As illustrated, the shape of the stirrer is such that it has cut-out areas such as the area 1295. This results in different velocities of the liquid being stirred and better mixing thereof. Attached to the top of the stirrer shaft 1292 is a pulley 1297. A flat cylindrical member 1299 is supported for rotation atop the shaft 1287. It rotates on a shaft 1301 shown in FIG. 53 inside the shaft 1287 in suitable bearing means. The shaft extends beyond the member 1299 and has attached to it a second pulley 1303. A chain 1305 extends between the pulleys 1297 and 1303. A motor 1307 which constantly runs when the machine is in operation has a metal disc 1309 attached to the end of its shaft 1311. The disc 1309 engages the member 1299, which has a resilient friction face on its bottom, when the shaft 1287 is in a downward position. This causes rotation of the member 1299 and with it the pulley 1303 which drives the pulley 1306 thereby driving the shaft 1297 on the end of which the stirrer 1293 is located. In the position shown, the stirrer is within a wash liquid 1309 in a well 1311 provided for that purpose. When a stirring operation is to be carried out, the shaft 1287 is raised by the type of apparatus described above in connection with the pipetter. As soon as the disc 1309 loses contact with the member 1299, rotation of the stirrer ceases. However, as the shaft 1287 is lowered after being rotated to a position over the cup, the disc 1309 again engages the rubber face of the member 1299 to cause a stirring action in the cup.

The instrument of the present invention has been described as a kinetic analyzer. It will be recognized by those skilled in the art that in more general terms, it is an automatic photometric analysis apparatus. That is to say that the arrangement of the analyzer lends itself to use not only as a kinetic analyzer, but as a photometric analyzer in which absorbence readings per se rather than a rate of absorbence is being determined. Furthermore, the various subsystems of the present invention are applicable to various types of analysis apparatus. It should further be noted that the inventors herein are the inventors of the overall system described and claimed herein. Various subsystems are the inventions of different inventive entities and separate applications were filed on August 22, 1974 covering those inventions.

Thus, an improved kinetic analyzer which permits automatically performing classical kinetic chemistries on an ultra micro scale handling samples at the rate of 150 per hour at low cost has been shown. Although a specific embodiment has been illustrated and described, it will be obvious to those skilled in the art that various modifications may be made without departing from the spirit of the invention which is intended to be limited solely to the appended claims.

What is claimed is:

1. A method of performing a kinetic analysis in automatic analyzer apparatus comprising automatically carrying out steps comprising in the order stated:
    a. pipetting a first reagent into a reaction cup;
    b. diluting a sample to be analyzed into the cup;
    c. preincubating the sample and first reagent together;
    d. pipetting a second reagent into the cup;
    e. stirring the mixture to start a desired reaction;
    f. transferring the reaction mixture to a photometer system;
    g. continuously observing the absorbance of the reaction mixture for a predetermined observation period during continuance of the reaction;
    h. computing the rate of change of absorbance over the full observation period; and
    i. providing an output indication of the computed rate of change.

2. A method according to claim 1 further including transferring said reaction mixture to said photometer through a thermostated heat exchanger to bring its temperature to a desired value.

3. A method according to claim 1 wherein a plurality of samples are to be analyzed wherein said steps a) and b) of claim 1 are first carried out seriatim for a plurality of samples, after which said plurality of samples are transferred as a group through a preincubation area whereupon said steps c) through h) are carried out seriatim for each of said samples.

4. A method according to claim 1 wherein each of said steps of pipetting comprises:
    a. moving a pipette to a position over a reagent bottle, wiping the tip of the pipette and lowering it into the bottle;
    b. creating a partial vacuum in the pipette to draw in reagent;
    c. raising the pipette out of the reagent, wiping the tip of the pipette, and moving it to a position over said reaction cup;
    d. lowering the pipette into said reaction cup so that the tip of the pipette will be below the surface of the contents of said cup after discharge of a predetermined amount of reagent; and
    e. discharging a predetermined amount of the reagent into said reaction cup.

5. A method according to claim 4 wherein the amount of reagent drawn into the pipette is greater than said predetermined amount which is discharged into the reaction cup and further including the step of discharging the remaining reagent liquid at a position where it will be taken to waste.

6. A method according to claim 5 wherein the step of wiping is accomplished using an irrigated sponge and wherein the discharge of excess liquid is into said sponge.

7. A method according to claim 1 wherein said step of diluting the sample into the reaction cup comprises the steps of:
    a. positioning a probe filled with diluent over a container containing said sample;
    b. wiping the tip of said probe;
    c. drawing a small bubble of air into said probe;
    d. lowering said probe into said container;
    e. drawing in a predetermined quantity of sample;
    f. withdrawing said probe from said sample, wiping the tip of said probe and moving to a position over said reaction cup;
    g. lowering said probe into said reaction cup so that its tip is below the liquid level its contents will attain; and
    h. discharging said sample along with a measured quantity of diluent into said reaction cup.

8. A method according to claim 7 and further including the step of discharging an additional quantity of diluent through said probe after discharge of said sample and diluent, with said probe over a waste receptacle, to thereby cleanse said probe in preparation for the next sample.

9. A method according to claim 1 wherein said steps of transferring comprise:

a. locating a transfer probe above a cup containing said reaction mixture, said probe flow-coupled in series with a photometer system;
b. applying suction to said photometer system to create a partial vacuum in said probe using positive displacement means;
c. oscillating said probe up and down whereby said probe will alternately draw in slugs of air and slugs of said reaction mixture; and
d. continuing to apply suction to said photometer system until a slug of said reaction mixture is located in the photometer cell.

10. A method according to claim 9 further including:
a. discharging a wash liquid into said reaction cup after said reaction mixture has been withdrawn therefrom; and
b. continuing to apply suction to said system while continuing oscillation of said probe to draw into said probe a plurality of slugs of wash liquid separated by bubbles of air.

11. A method according to claim 9 further including the step of applying a fluid pressure to said photometer system momentarily, prior to applying suction, to dislodge any material within the photometer system.

12. A method according to claim 9 and further including the step of bringing said reaction mixture precisely to a predetermined temperature during transfer.

13. A method according to claim 1 wherein said photometer system includes means for providing an analog output proportional to absorbance and further including the step of automatically offsetting the output of the photometer at the beginning of said observation period to place it approximately at zero.

14. A method according to claim 1 wherein said step of computing comprises:
a. integrating the output of said photometer in a first direction for the first half of the observation period to obtain a first value;
b. integrating said output in the opposite direction for the second half of the observation period to obtain a second value; and
c. differencing said first and second values to obtain a value proportional to the average rate of change of the absorbance signal over the measuring period.

15. A method according to claim 14 further including the step of carrying out a curvature computation to determine the degree of linearity of the rate of change.

16. A method according to claim 15 wherein said curvature computation is accomplished by the steps of:
a. integrating the output of said photometer in a first direction for the first quarter of the observation period;
b. integrating the output of said photometer in the opposite direction for the second and third quarters of the observation period;
c. integrating the output of said photometer in said first direction for the fourth quarter of said observation period; and
d. finding the net value of said integrations, said value being the curvature value.

17. A method according to claim 16 further including the step of comparing said curvature value with a predetermined percentage of said rate of change output and providing an output if said curvature value is greater than said predetermined value.

18. A method according to claim 17 further including checking the sign of said curvature value and providing a first output signal if said value is positive and greater than said predetermined percentage and a second output signal if said value is greater than said predetermined value and negative.

19. A method according to claim 16 further including the step of controlling the scale factor during each of said quarters to permit checking a non-linear curve.

20. An instrument for photometric kinetic analysis comprising:
a. a reaction cup;
b. means for pipetting a measured amount of a first liquid reagent into said cup;
c. means for picking up a metered amount of a sample and diluting it with diluent into said cup;
d. means for preincubating said first reagent sample and diluent;
e. means for pipetting a measured amount of a second liquid reagent into said cup to initiate a reaction;
f. means for stirring the contents of said cup immediately after pipetting of said second reagent;
g. a photometer system including a light source, sensor means, a photometer cell through which the light from said light source passes to impinge on said sensor means;
h. amplifying means for providing an output proportional to the absorbance of the material in said cell;
i. means for transferring, during said reaction, the liquid contents of said cup to the sample cell of said photometer through a thermostatted block; and
j. control means for controlling the operation of each of the above described a) through i).

21. Apparatus according to claim 20 further including:
a. means to compute the rate of change of absorbance over a predetermined observation period; and
b. means to provide an output indication of said rate of change.

22. Apparatus according to claim 20 wherein said first reagent is pipetted at a first location and said second reagent at a second location, said preincubating means being operative between said first and second locations and further including means to transfer said cup from said first to said second location.

23. Apparatus as in claim 22 for analyzing a plurality of samples further including:
a. means for holding a plurality of samples to be analyzed; and
b. means for successively moving each of said plurality of samples into a position where they can be picked up for analysis.

24. Apparatus according to claim 23 wherein samples are processed in batches and futher including:
a. means holding said cup along with a plurality of similar cups;
b. means to step said cup holding means through said first location, said control means being operative to cause said first means for pipetting and said means for picking up and diluting to successively pipet reagent and dilute sample and diluent into each of said cups in sequence;
c. means to transfer said holding means to said second location;
d. means to step said cup holding means through said second location, said control means being adapted to cause the pipetting of said second reagent, stirring and transfer of said mixture as said holder is stepped through said second location.

25. Apparatus according to claim 20 wherein each of said means to pipette comprises:

a. a pipette probe;
b. a supply vial containing said first liquid reagent;
c. wiping means over said supply vial;
d. positive displacement means;
e. a flexible tube filled with air coupling said pipette probe to said positive displacement means; and
f. means to mechanically move said pipette probe vertically and horizontally between a position above said reagent vial and a position above said cup.

26. Apparatus according to claim 25 wherein said positive displacement means comprises a positive displacement pump including a piston and cylinder, said flexible tube coupling said pipette probe and said cylinder.

27. Apparatus according to claim 25 wherein said wiping means comprise a sponge wiper and wherein said control means operate said pump to draw in reagent in excess of the required reagent volume to be deposited in the cup, are operable to cause said pump to discharge only the required amount of reagent and are further operable to cause said pump to expel the excess volume when positioned over said sponge after rotation to a position over said vial whereby upon withdrawal from said reagent, the tip of said pipette will be wiped and will be wiped again when descending to a position above said reagent.

28. Apparatus according to claim 25 wherein said pipette probe is detachable for replacement.

29. Apparatus according to claim 20 wherein said means to dilute comprise:
a. a diluter probe;
b. means to move said probe vertically and horizontally;
c. wiping means situated so that said probe passes through it on entering and leaving the sample to be diluted;
d. a positive displacement diluent pump;
e. a positive displacement sample pump coupled through flexible tubing to said probe;
f. a diluent supply;
g. a valve alternatively coupling said diluent supply to said diluent pump and said diluent pump to said sample pump; and
h. means for driving said diluent pump, said sample pump and said valve.

30. Apparatus according to claim 29 wherein said diluent pump and sample pump each comprise a cylinder and piston and said means for driving comprise a motor and a plurality of cams.

31. Apparatus according to claim 29 wherein said means to move said probe comprise a motor and a cam arrangement to move said probe between a position where it is lowered into said sample holding means and a position where it is lowered above said reaction cup, movement between said sample holding means and cup being accomplished by raising and horizontally moving said probe.

32. Apparatus according to claim 29 wherein said valve is a slide valve comprising a body and a sliding valve member.

33. Apparatus according to claim 20 wherein said means to transfer comprise:
a. a transfer probe;
b. conduit means coupling said transfer probe to one end of said photometer cell;
c. further conduit means extending from the other end of the photometer cell to an outlet;
d. controlled positive displacement means to supply suction to said outlet and concomittantly to said probe; and
e. means to oscillate said transfer probe up and down, into and out of the cup to draw in a plurality of slugs of reaction mixture separated by air slugs.

34. Apparatus according to claim 33 further including means to discharge a wash liquid into said cup after said reaction mixture has been drawn in.

35. Apparatus according to claim 33 wherein said positive displacement means comprises:
a. a transfer pump including a cylinder and a piston, said cylinder having a combined inlet-outlet port;
b. a slide valve including a valve body having a first passage means coupled to a waste outlet and a second passage means coupled to said photometer cell, and a slidable valve member containing channel means therein for coupling said port and said first passage means when in a first position and said port and said second passage means when in a second position; and
c. means for driving said piston and said valve member.

36. Apparatus according to claim 35 wherein said means for oscillation comprise:
a. a master piston and cylinder containing hydraulic fluid;
b. a slave piston and cylinder coupled to said master cylinder, said slave piston being mechanically coupled to said probe; and
c. means to oscillate the piston in said master cylinder.

37. Apparatus according to claim 36 wherein said means to oscillate the master piston comprise a cam driving the piston of said master cylinder, said apparatus further comprising a rotary shaft mounting said cam, and two additional cams, also mounted on said rotary shaft and respectively constituting said means for driving said transfer pump and slidable valve member.

38. Apparatus according to claim 20 wherein said photometer system comprises:
a. a light source emitting predetermined wave lengths;
b. means for forming the light from said source into a beam;
c. means for defining the etendu of said beam including a field stop and aperture stop;
d. means for splitting said beams into first and second beams while preserving the uniformity of illumination over both beams, said first beam being directed through said photometer cell;
e. means to image said field stop near the entrance of said cell and said aperture stop near the exit of said cell such that when passing through said cell said first beam does not touch the sides thereof;
f. a first detector;
g. means forming an image of said aperture stop wholly on the sensitive area of said first detector;
h. a second detector in the path of said second beam; and
i. means forming an image of one of said field and aperture stops wholly on the sensitive area of said second detector.

39. Apparatus according to claim 38 wherein operation at two different wave lengths is desired and further including:
a. another light sourve emitting different wave lengths;

b. a movable mirror directing light from either said one or other light source to said sample cell;

c. a second filter adapted to pass light in another band of wave lengths; and d. means to selectively position one and the other of said filters in the light path.

40. Apparatus according to claim 20 further including means for maintaining said photometer cell at a predetermined temperature and means for bringing the reaction mixture to that temperature before it reaches said photmeter cell.

41. Apparatus according to claim 21 wherein said means to compute the rate of change of absorbance comprise:

a. means to establish an observation period; and b. means to (1) integrate the output signal of said photometer system in a first direction for the first half of said observation period, (2) integrate the output signal in the opposite direction for the second half of said observation period and (3) determine the difference between the two integrations, said difference being proportional to the rate of change of absorbance.

42. Apparatus according to claim 41 and further including means to offset the output of said photometer system to a value near zero immediately before the beginning of said observation period.

43. Apparatus according to claim 41 further including means to simultaneously compute the curvature of said photometer system output.

44. Apparatus according to claim 43 wherein said means to compute curvature comprise means to integrate the output of said photometer system in a first direction for the first quarter of said observation period, to integrate said output in a second direction for the second and third quarters of said observation period and in said first direction for the fourth quarter of said observation period, whereby the net result of said integrations will represent the curvature of said signal over the observation period.

45. Apparatus according to claim 43 further including means to control the scale factor during each of said quarters.

46. Apparatus according to claim 41 further including means to compare the output of said photometer system with pre-established maximum and minimum levels and to provide respective error indications if said levels are exceeded.

47. Apparatus according to claim 46 further comprising:

a. an output register for receiving the difference output of said means to compute rate of range of absorbance;

b. an output printer; and c. means to provide the contents of said output register and said error indications to said output printer.

48. Apparatus according to claim 20 wherein said first means for pipetting and said means for diluting comprise a preparation unit and said second means for pipetting, means for stirring, means for transferring, and said photometer system comprise and analyzer unit and wherein said control means comprise:

a. a first level control means for control of both of said preparation and analyzer unit;

b. a first timing means for controlling said preparation unit; and c. a second timing means for controlling said analyzer unit.

49. A method of performing kinetic analysis in automatic analyzer apparatus comprising automatically carrying out steps comprising, in the stated order:

a. pipetting a first reagent into a cup;

b. diluting a sample to be analyzed into the cup;

c. preincubating the sample and first reagent together;

d. pipetting a second reagent into said cup;

e. stirring the mixture to start a desired reaction;

f. transferring the reaction mixture to a photometer system;

g. measuring the absorbance of the reaction mixture in said photometer during continuation of the reaction; and h. providing an output indication of the measured absorbance.

* * * * *

UNITED STATES PATENT OFFICE
CERTIFICATE OF CORRECTION

Patent No. 4,052,161                 Dated October 4, 1977

Inventor(s) John G. Atwood, Hamilton W. Marshall, Jr., and Peter H. Heinz

It is certified that error appears in the above-identified patent and that said Letters Patent are hereby corrected as shown below:

Column 1, line 35 change "quanties" to -- quantities --.

Column 1, line 68, change "absorbence" to -- absorbance --.

Column 2, line 35, change "absorbence" to --absorbance --.

Column 3, line 20, change "examle," to -- example, --.

Column 4, line 3, change "thought" to -- through --.

Column 6, line 40, change "conditon" to -- condition --.

Column 8, line 48, change "fusing" to -- using --.

UNITED STATES PATENT OFFICE
CERTIFICATE OF CORRECTION

Patent No. 4,052,161　　　　　　　Dated October 4, 1977

Inventor(s) John G. ATwood, Hamilton W. Marshall, Jr., and Peter H. Heinz

It is certified that error appears in the above-identified patent and that said Letters Patent are hereby corrected as shown below:

Column 8, line 62, change "ete.," to -- etc., --.

Column 9, line 67-68 change "photom-eter" to -- photo-meter --.

Column 11, line 38, change "absorbance" to -- absorption --.

Column 15, line 1, change "change" to -- chance --.

Column 15, line 27, change "serun" to -- serum --.

Column 17, line 10, change 6.16" to -- 60.16 --.

Column 19, line 9, change "152" to -- 151 --.

Column 19, line 11, change "1" to -- 10 --.

Column 19, line 31, change "80' to -- 80 --.

UNITED STATES PATENT OFFICE
CERTIFICATE OF CORRECTION

Patent No. 4,052,161  Dated October 4, 1977

Inventor(s) John G. Atwood, Hamilton W. Marshall, Jr., and Peter H. Heinz

It is certified that error appears in the above-identified patent and that said Letters Patent are hereby corrected as shown below:

Column 19, line 32, change "6" to -- $\bar{6}$ --.

Column 19, line 55, change "SM" to -- $\overline{SM}$ --.

Column 19, line 50, change "SM" first occurrence to $\overline{SM}$ --.

Column 20, line 25, change "80" to -- $\overline{80}$ --.

Column 20, line 25, change "6' to -- $\bar{6}$ --.

Column 20, line 56, change "would" to -- could --.

Column 23, line 64, change "illusrated" to -- illustrated --.

Column 24, line 14, change "8a" to -- 8b --.

UNITED STATES PATENT OFFICE
CERTIFICATE OF CORRECTION

Patent No. 4,052,161  Dated October 4, 1977

Inventor(s) John G. Atwood, Hamilton W. Marshall, Jr., and Peter H. Heinz

It is certified that error appears in the above-identified patent and that said Letters Patent are hereby corrected as shown below:

Column 27, line 60, change ""GOC" to -- "$\overline{GOC}$" --.

Column 34, line 51, change "are" to -- and --.

Column 39, line 52, change "dluter" to -- diluter --.

Column 43, line 64, before "well" insert -- quite --.

Column 46, line 49, change "32" second occurrence to $\overline{32}$ --.

Column 49, line 22, change "magazine" to -- magazines --.

Column 50, line 11, change "tensions" to -- tension --.

Column 50, line 59, change "36" to -- $\underline{36}$ --.

UNITED STATES PATENT OFFICE

CERTIFICATE OF CORRECTION

Patent No. 4,052,161          Dated October 4, 1977

Inventor(s) John G. Atwood, Hamilton W. Marshall, Jr., and Peter H. Heinz

It is certified that error appears in the above-identified patent and that said Letters Patent are hereby corrected as shown below:

Column 50, line 62, change "7" to -- $\underline{7}$ --.

Column 50, line 67, change "36" to -- $\underline{36}$ --.

Column 50, line 68, change "7" to -- $\underline{7}$ --.

Column 52, line 9, before "is" omit -- which --.

Column 51, line 4, change "1" to -- $\underline{1}$ --.

Column 51, line 4, change "3" to -- $\underline{3}$ --.

Column 57, line 32, before "a" insert -- a. --.

Column 58, line 1, change "supply" to -- apply --.

Column 59, line 12, change "photmeter" to -- photometer --.

Signed and Sealed this

Nineteenth Day of December 1978

[SEAL]

Attest:

RUTH C. MASON
Attesting Officer

DONALD W. BANNER
Commissioner of Patents and Trademarks